(12) United States Patent
Bernardon et al.

(10) Patent No.: US 7,148,245 B2
(45) Date of Patent: Dec. 12, 2006

(54) BIPHENYL DERIVATIVES SUBSTITUTED WITH AN AROMATIC OR HETEROAROMATIC RADICAL, AND PHARMACEUTICAL AND COSMETIC COMPOSITIONS CONTAINING THEM

(75) Inventors: Jean-Michel Bernardon, Le Rouret (FR); Philippe Nedoncelle, Grasse (FR)

(73) Assignee: Galderma Research & Development, Biot (FR)

( * ) Notice: Subject to any disclaimer, the term of this patent is extended or adjusted under 35 U.S.C. 154(b) by 374 days.

(21) Appl. No.: 10/613,320

(22) Filed: Jul. 7, 2003

(65) Prior Publication Data

US 2004/0030141 A1 Feb. 12, 2004

Related U.S. Application Data

(62) Division of application No. 09/932,938, filed on Aug. 21, 2001, now Pat. No. 6,649,612, which is a division of application No. 09/284,026, filed as application No. PCT/FR98/01834 on Aug. 21, 1998, now Pat. No. 6,316,009.

(30) Foreign Application Priority Data

Aug. 21, 1997 (FR) .................................. 97 10552

(51) Int. Cl.
*A61K 8/49* (2006.01)
*A61K 31/4418* (2006.01)
*C07D 213/06* (2006.01)

(52) U.S. Cl. ....................... 514/354; 514/356; 514/569; 424/401; 546/322; 546/324; 562/466; 562/492

(58) Field of Classification Search ................ 546/322, 546/342; 562/466, 492; 514/569, 354, 356; 424/401

See application file for complete search history.

(56) References Cited

U.S. PATENT DOCUMENTS 6,316,009 B1 11/2001 Bernardon et al.
6,649,612 B1 11/2003 Bernardon et al.

FOREIGN PATENT DOCUMENTS

| EP | 0382077 A | 8/1990 |
|----|-----------|--------|
| GB | 2150563 A | 7/1985 |
| JP | 2-124859 | 5/1990 |

OTHER PUBLICATIONS 1977-1981 Chem. Substance Index, [79691-46-6], 95: 203660z.
1977-1981 Chem. Substance Index, [50446-43-0] 88: 191416q.
1977-1981 Chem. Substance Index, [50446-43-0] 87: 201500h.
1977-1981 Chem. Substance Index, [78923-62-3], 95:114925x.
1977-1981 Chem. Substance Index, [71128-90-0], 92:198377u.
1977-1981 Chem. Substance Index, [71128-90-0], 95:150260k.
1977-1981 Chem. Substance Index, [71128-90-0], 91:107964y.
1977-1981 Chem. Substance Index, [55255-72-6], 114: 14275s.
1977-1981 Chem. Substance Index, [50446-43-0], 114: 142751s; 115: 182705g.
1977-1981 Chem. Substance Index, [50446-43-0], 110: 73465d.
1977-1981 Chem. Substance Index, [50446-43-0], 115: 182318h.
1977-1981 Chem. Substance Index, [50446-43-0], 110: 192791t.
1977-1981 Chem. Substance Index, [78923-62-3], 109: 169929g.
1977-1981 Chem. Substance Index, [78923-62-3], 111:P57264d.
1977-1981 Chem. Substance Index, [136612-90-3], 115: 182318h.
1977-1981 Chem. Substance Index, [104581-20-6], 105:152602x.
1977-1981 Chem. Substance Index, [19399-68-9], 98: 16214g.
1977-1981 Chem. Substance Index, [83909-17-5], 98:16214g.
1977-1981 Chem. Substance Index, [50446-43-0], 97:197960v.
1977-1981 Chem. Substance Index, [50446-43-0] 99: 223881h.
1987-1991 Chem. Substance Index, [115424-59-4], 113: 40021r.
1987-1991 Chem. Substance Index, [115424-59-4], 112: P 28162j.
1987-1991 Chem. Substance Index, [115424-59-4], 109: P 55877r.
1987-1991 Chem. Substance Index, [115424-59-4], 109: P 180438z.
1987-1991 Chem. Substance Index, [115424-59-4], 111: p 164248yn.
1992-1996 Chem. Substance Index, [154488-08-1] 121: pr 9370v.
1992-1996 Chem. Substance Index, [154488-08-1] 125: pr 58484b.
1992-1996 Chem. Substance Index, [154488-08-1] 120: 270343w.
1992-1996 Chem. Substance Index, [154488-08-1] 123: pr 169590m.

(Continued)

*Primary Examiner*—Laura L. Stockton
(74) *Attorney, Agent, or Firm*—Nixon & Vanderhye P.C.

(57) ABSTRACT

Compounds of formula (I):

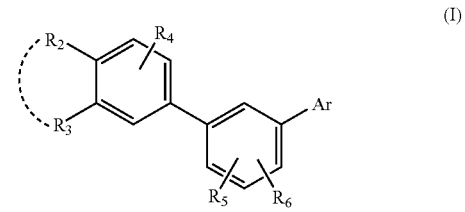

in which:
Ar represents an aromatic or a heteroaromatic radical optionally substituted, in particular, with an alkyl or a carboxyl group,
$R_2$ and $R_3$ represent, in particular, H or alkyl, or
$R_2$ and $R_3$, taken together, form a 5- or 6-membered ring,
$R_4$ and $R_5$ represent, in particular, H or halogen,
$R_6$ represents, in particular, H or lower alkyl,
and the salts of the compounds of formula (I).

These compounds can be used in particular in the treatment of dermatological complaints associated with a keratinization disorder, and for combating ageing of the skin.

40 Claims, No Drawings

OTHER PUBLICATIONS 1992-1996 Chem. Substance Index, [19399-68-9] 120: 270343w.
1992-1996 Chem. Substance Index, [19399-68-9] 123: pr 169590m.
1992-1996 Chem. Substance Index, [19399-68-9] 125: pr 58484b.
1992-1996 Chem. Substance Index, [155186-06-4] 121: pr 9370v.
1992-1996 Chem. Substance Index, [155186-07-5] 123: pr 169590m.
1992-1996 Chem. Substance Index, [155186-07-5] 125: pr 58484b.
1992-1996 Chem. Substance Index, [22421-03-0] 122: pr 290227f.
1992-1996 Chem. Substance Index, [81979-63-7] 119: 117949h.
1987-1991 Chem. Substance Index, [135449-17-1], 120:106487a.
1992-1996 Chem. Substance Index, [50446-43-0] 123: pr 157220q.
1992-1996 Chem. Substance Index, [115424-59-4],250937.
1992-1996 Chem. Substance Index, [17798-71-9], 68: 114196c.
1992-1996 Chem. Substance Index, [22421-03-0], 70: 96341f.
1992-1996 Chem. Substance Index, [17798-72-0], 68: 114196c; 69: 67145u.
1982-1986 Chem. Substance Index, [[86581-39-7], 99:70123k.
1982-1986 Chem. Substance Index, [81979-63-7], 97:5891d.
1982-1986 Chem. Substance Index, [82854-06-6] 97: P 111442t.
1982-1986 Chem. Substance Index, [67564-84-5] 103: 53645r.
1987-1991 Chem. Substance Index, [128565-92-4] 114: P 96801h.
1987-1991 Chem. Substance Index, [128565-90-2]113: P 78409m.
1987-1991 Chem. Substance Index, [128565-90-2]114: P 96801h.
1987-1991 Chem. Substance Index, [128565-91-3] 113: P 78409m.
1987-1991 Chem. Substance Index, [128565-91-3] 114: P 96801h.
1987-1991 Chem. Substance Index, [128566-26-7] 113: P 78409m.
1987-1991 Chem. Substance Index, [128566-27-8] 113: P 78409m.
1987-1991 Chem. Substance Index, [120841-89-6] 110: 232184f.
1987-1991 Chem. Substance Index, [120841-92-1] 110: 232184f.
1987-1991 Chem. Substance Index, [67564-84-5] 108: 211418d.
1987-1991 Chem. Substance Index, [67564-84-5] 109: 99627p.
1987-1991 Chem. Substance Index, [110006-99-0] 107: P 219893e.
1987-1991 Chem. Substance Index, [135449-17-1], 115: 91751c.
1987-1991 Chem. Substance Index, [50446-43-0], 114: 142751s; 115: 182705g.
1987-1991 Chem. Substance Index, [50446-43-0] 110: 75465d.
1987-1991 Chem. Substance Index, [50446-43-0] 115: 182318h.
1987-1991 Chem. Substance Index, [50446-43-0] 110: 192791t.
1987-1991 Chem. Substance Index, [78923-62-3], 109: 169929q.
1987-1991 Chem. Substance Index, [78923-62-3] 111: P 57264d.
1987-1991 Chem. Substance Index, [136612-90-3] 115: 182318h.
1992-1996 Chem. Substance Index, [81979-63-7] 120: 106487a.
1992-1996 Chem. Substance Index, [50446-43-0] 120: pr P 19195q.
1992-1996 Chem. Substance Index, [50446-43-0] 120:192767w.
1992-1996 Chem. Substance Index, [50446-43-0] 120:322873r.
1992-1996 Chem. Substance Index, [50446-43-0] 125:195162j.
1992-1996 Chem. Substance Index, [167500-04-1]123: pr 213852z.
1992-1996 Chem. Substance Index, [167500-04-1] 123: pr 169590m.
1992-1996 Chem. Substance Index, [115424-59-4]123: pr 213852z.
1982-1986 Chem. Substance Index, [81979-63-7] 103: 53645t.
1992-1996 Chem. Substance Index, [50446-43-0] 123: pr P 10195q.
1992-1996 Chem. Substance Index, [50446-43-0] 120: 192767w.
1992-1996 Chem. Substance Index, [50446-43-0] 120: 322873r.
1992-1996 Chem. Substance Index, [50446-43-0] 125: 195162j.
1992-1996 Chem. Substance Index, [ 167500-04-1] 123: pr 213852z.
1992-1996 Chem. Substance Index, [ 167500-04-1] 123: pr 169590m.
1992-1996 Chem. Substance Index, [155186-06-4] 121: 56907k.
1992-1996 Chem. Substance Index, [155186-06-4] 123: pr 213852z.
1992-1996 Chem. Substance Index, [155186-06-4] 123: pr 169590m.
Pepin et al, English Abstract of EP 0 360 701 A1, Antifungal compounds containing amides and phenyl groups, Mar. 28, 1990.
Vymetal et al, Sbornik Vedeckych Prai Vysoke Skoly Banske v Ostrave, Rada, Hutnicka, 28(1), p. 97-108 (1982) (English Abstract).
Office Action from JPO dated Nov. 16, 2004 in JP 11514010 and English translation.

BIPHENYL DERIVATIVES SUBSTITUTED WITH AN AROMATIC OR HETEROAROMATIC RADICAL, AND PHARMACEUTICAL AND COSMETIC COMPOSITIONS CONTAINING THEM

This application is a division of application Ser. No. 09/932,938, filed Aug. 21, 2001 (now U.S. Pat. No. 6,649,612), which is a divisional of application Ser. No. 09/284,026, filed Apr. 6,1999 (now U.S. Pat. No. 6,316,009), which is a 371 National Phase of PCT/FR98/01834, filed 21 Aug. 1998, the entire content of each of which is hereby incorporated by reference in this application.

The invention relates to, as novel and useful industrial products, biphenyl derivatives substituted with an aromatic or heteroaromatic radical. The invention also relates to the use of these novel compounds in pharmaceutical compositions intended for use in human or veterinary medicine, or alternatively in cosmetic compositions.

The compounds according to the invention have pronounced activity in the fields of cell differentiation and proliferation and find applications more particularly in the topical and systemic treatment of dermatological complaints associated with a keratinization disorder, dermatological (or other) complaints with an inflammatory and/or immunoallergic component, and dermal or epidermal proliferations, whether they are benign or malignant. These compounds can also be used in the treatment of connective tissue degenerative diseases, for controlling ageing of the skin, whether this is light-induced or chronological ageing, and for treating cicatrization disorders. They moreover find an application in the opthalmological field, in particular in the treatment of corneopathy.

The compounds according to the invention can also be used in cosmetic compositions for body and hair hygiene.

Triaromatic derivatives whose structure consists essentially of two substituted aromatic rings linked together by a 5- or 6-membered heteroaryl divalent radical containing, as hetero atom, an oxygen atom, a sulphur atom and/or at least one nitrogen atom, have already been described in EP-382,077.

The compounds according to the present invention, which are also triaromatic derivatives, differ from those of EP-382,077 essentially in that if they have a heteroaryl radical, in particular a substituted pyridyl, furyl or thienyl radical, this radical is located at the end of the chain, thus giving these compounds a chemical structure which is totally different from that of the compounds of EP-382,077.

Although the compounds according to the invention are not limited to those containing a heteroaryl radical, it has nevertheless been found, surprisingly and unexpectedly, that the compounds containing such a radical have excellent pharmaceutical and cosmetic properties which are entirely similar to those of the compounds according to the invention containing a substituted phenyl radical at the end of the chain.

It has moreover been possible to demonstrate that the compounds according to the invention are devoid of side effects, while at the same time having excellent activity.

The subject of the present invention is thus novel compounds which can be represented by the following general formula:

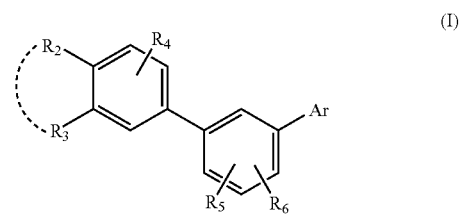

in which:

Ar represents an aromatic or heteroaromatic radical chosen from:

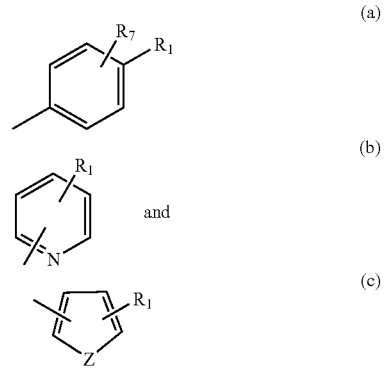

Z being O or S, $R_1$ represents —$CH_3$, —$CH_2$—OH, —$OR_8$ or —$COR_9$, $R_2$ and $R_3$, which may be identical or different, represent H, linear or branched $C_1$–$C_{15}$ alkyl, cycloalkyl, —$ZR_{10}$ or a polyether radical, at least one from among $R_2$ and $R_3$ representing a linear or branched $C_1$–$C_{15}$ alkyl, or $R_2$ and $R_3$, taken together, form a 5- or 6-membered ring, optionally sutbstituted with at least one methyl and/or optionally interrupted by an oxygen or sulphur atom or by an SO or $SO_2$ radical, $R_4$ represents H, a halogen atom, linear or branched $C_1$–$C_{20}$ alkyl, —$OR_{10}$, —$OCOR_{11}$ or a polyether radical, $R_5$ represents H, a halogen atom, linear or branched $C_1$–$C_{20}$ alkyl, —$OCOR_{11}$, —$OR_{12}$, mono- or polyhydroxyalkyl, —$NO_2$,

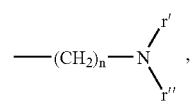

—$(CH_2)_n$—$NHCOCH_3$, —$CH$=$CH$—$COR_{13}$, —$(CH_2)_nCOR_{13}$, n being 0 to 6, —O—$(CH_2)_mCOR_{13}$, —O—$(CH_2)_mOH$, m being 1 to 12, optionally substituted aryl, optionally substituted aralkyl, optionally substituted heteroaryl, a polyether radical or a —$CH_2$-polyether radical, $R_6$ represents H, lower alkyl or —$OR_{10}$, $R_7$ represents H, a halogen atom, linear or branched $C_1$–$C_{20}$ alkyl, —$OR_{10}$ or —$OCOR_{11}$ or a polyether radical, $R_8$ represents H, lower alkyl or $—COR_{11}$,
$R_9$ represents H, lower alkyl, $—OR_{14}$ or

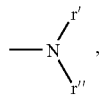

$R_{10}$ represents H or lower alkyl,
$R_{11}$ represents lower alkyl,
$R_{12}$ represents H, linear or branched $C_1–C_{20}$ alkyl, mono- or polyhydroxyalkyl, or optionally substituted aryl or aralkyl,
$R_{13}$ represents H, lower alkyl, $—OR_{10}$, aryl or

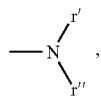

$R_{14}$ represents H, alkyl, linear or branched $C_1–C_{20}$ alkyl, alkenyl, mono- or polyhydroxyalkyl, optionally substituted aryl or aralkyl, or a sugar residue,
r' and r", which may be identical or different, represent H, OH, lower alkyl, mono- or polyhydroxyalkyl, optionally substituted aryl, an amino acid residue or a peptide residue, or r' and r", taken together, form a heterocycle, and the salts of the compounds of formula (I) when $R_1$ represents a carboxylic acid function, as well as the optical and geometrical isomers of the said compounds of formula (I).

When the compounds according to the invention are in the form of a salt, this is preferably a salt of an alkali metal or alkaline-earth metal, or alternatively of zinc or of an organic amine.

According to the present invention, the expression "lower alkyl" refers to a $C_1–C_6$ radical, preferably the methyl, ethyl, isopropyl, butyl, tert-butyl and hexyl radicals.

The term "linear or branched $C_1–C_{15}$ alkyl" refers in particular to the methyl, ethyl, propyl, 2-ethylhexyl, octyl and dodecyl radicals. When the alkyl radical is $C_1–C_{20}$, the hexadecyl and octadecyl radicals are also intended.

The term "cycloalkyl" refers to an optionally substituted mono- or polycyclic radical containing from 5 to 10 carbon atoms, in particular a cyclopentyl, cyclohexyl, 1-methylcyclohexyl or 1-adamantyl radical.

The term "monohydroxyalkyl" refers to a radical preferably containing 1 to 6 carbon atoms, in particular a hydroxymethyl, 2-hydroxyethyl, 2-hydroxypropyl or 3-hydroxypropyl radical.

The term "polyhydroxyalkyl" refers to a radical preferably containing 3 to 6 carbon atoms and from 2 to 5 hydroxyl groups, such as the 2,3-dihydroxypropyl, 2,3,4-trihydroxybutyl and 2,3,4,5-tetrahydroxypentyl radicals or a pentaerythritol residue.

The term "polyether radical" refers to a radical containing from 2 to 6 carbon atoms which is interrupted by at least two oxygen atoms, such as the methoxymethoxy, methoxyethoxy and methoxyethoxymethoxy radicals.

The term "$—CH_2$-polyether radical" refers to a radical preferably chosen from the methoxymethoxymethyl, ethoxymethoxymethyl and methoxyethaxymethoxymethyl radicals.

The term "aryl" preferably refers to a phenyl radical optionally substituted with at least one halogen, a lower alkyl, a hydroxyl, a $C_1–C_3$ alkoxy, a nitro function, a polyether radical or an amino function optionally protected with an acetyl group or optionally substituted with at least one $C_1–C_6$ lower alkyl or alkoxy.

The term "aralkyl" preferably refers to a benzyl or phenethyl radical optionally substituted with at least one halogen, a lower alkyl, a hydroxyl, a $C_1–C_3$ alkoxy, a nitro function, a polyether radical or an amino function optionally protected with an acetyl group or optionally substituted with at least one $C_1–C_6$ lower alkyl or alkoxy.

The term "heteroaryl radical" preferably refers to a pyridyl, furyl or thienyl radical, optionally substituted with at least one halogen, a lower alkyl, a hydroxyl, a $C_1–C_3$ alkoxy, a nitro function, a polyether radical or an amino function optionally protected with an acetyl group or optionally substituted with at least one $C_1–C_6$ lower alkyl or alkoxy.

The term "alkenyl" refers to a radical preferably containing 2 to 5 carbon atoms and containing one or more ethylenic unsaturations, such as, more particularly, an allyl radical.

The term "sugar residue" refers to a residue derived in particular from glucose, from galactose or from mannose, or alternatively from glucuronic acid.

The term "amino acid residue" refers in particular to a residue derived from lysine, from glycine or from aspartic acid, and the term "peptide residue" refers more particularly to a dipeptide or tripeptide residue resulting from the combination of amino acids.

The term "heterocycle" preferably refers to a piperidino, morpholino, pyrrolidono or piperazino radical, optionally substituted in position 4 with a $C_1–C_6$ lower alkyl or a mono- or polyhydroxyalkyl as defined above.

When $R_4$, $R_5$ and/or $R_7$ represent a halogen atom, this is preferably a fluorine, chlorine or bromine atom.

According to a preferred embodiment, the compounds according to the invention correspond to the general formulae (II) and (III) below:

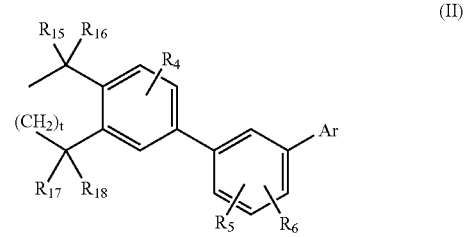

(II)

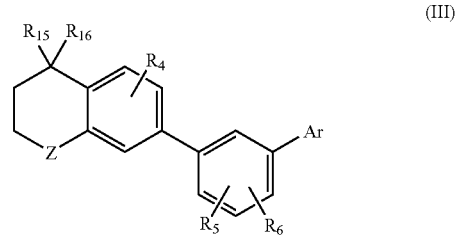

(III)

in which:

Ar represents a radical of formula (a) or (b) below:

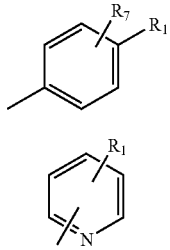

R$_1$, R$_4$, R$_5$, R$_6$, R$_7$ and Z having the same meanings as those given above for formula (I), R$_{15}$, R$_{16}$, R$_{17}$ and R$_{18}$, which may be identical or different, represent H or —CH$_3$, and t is 1 or 2.

Among the compounds of formulae (I) to (III) above, according to the present invention, mention may be made in particular of the following:

4-[4-hydroxy-3-(5,6,7,8-tetrahydro-5,5,8,8-tetramethyl-2-naphthyl)phenyl]benzoic acid, and its methyl ester, 4-[4-(5-hydroxypentyloxy)-3-(5,6,7,8-tetrahydro-5,5,8,8-tetramethyl-2-naphthyl)phenyl]benzoic acid, and its methyl ester, 4-[4-(6-hydroxyhexyloxy)-3-(5,6,7,8-tetrahydro-5,5,8,8-tetramethyl-2-naphthyl)phenyl]benzoic acid and its methyl ester, 4-[4-(7-hydroxyheptyloxy)-3-(5,6,7,8-tetrahydro-5,5,8,8-tetramethyl-2-naphthyl)phenyl]benzoic acid, 4-[4-(8-hydroxyoctyloxy)-3-(5,6,7,8-tetrahydro-5,5,8,8-tetramethyl-2-naphthyl)phenyl]benzoic acid, 4-[4-(9-hydroxynonyloxy)-3-(5,6,7,8-tetrahydro-5,5,8,8-tetramethyl-2-naphthyl)phenyl]benzoic acid, 4-[4-methoxy-3-(5,6,7,8-tetrahydro-5,5,8,8-tetramethyl-2-naphthyl)phenyl]benzoic acid, 4-[4-methoxyethoxymethoxy-3-(5,6,7,8-tetrahydro-5,5,8,8-tetramethyl-2-naphthyl)phenyl]benzoic acid, 4-[4-benzyloxy-3-(5,6,7,8-tetrahydro-5,5,8,8-tetramethyl-2-naphthyl)phenyl]benzoic acid, 4'-(2,3-dihydroxypropoxy)-3'-(5,5,8,8-tetramethyl-5,6,7,8-tetrahydro-2-naphthyl)biphenyl-4-carboxylic acid (racemic), 4'-(2,2-dimethyl-[1,3]dioxolan-4-ylmethoxy)-3'-(5,5,8,8-tetramethyl-5,6,7,8-tetrahydro-2-naphthyl)-biphenyl-4-carboxylic acid (racemic), 4'-(2-morpholin-4-yl-ethoxy)-3'-(5,5,8,8-tetramethyl-5,6,7,8-tetrahydro-2-naphthyl)biphenyl-4-carboxylic acid, methyl 2'-(5,5,8,8-tetramethyl-5,6,7,8-tetrahydro-2-naphthyl)-[1,1';4',1"]terphenyl-4"-carboxylate, 2'-(5,5,8,8-tetramethyl-5,6,7,8-tetrahydro-2-naphthyl)-[1,1';4',1"]terphenyl-4"-carboxylic acid, 4-methoxymethoxy-2'-(5,5,8,8-tetramethyl-5,6,7,8-tetrahydro-2-naphthyl)-[1,1';4',1"]terphenyl-4"-carboxylic acid, 4-hydroxy-2'-(5,5,8,8-tetramethyl-5,6,7,8-tetrahydro-2-naphthyl)-[1,1';4',1"]terphenyl-4"-carboxylic acid, 4-methoxy-2'-(5,5,8,8-tetramethyl-5,6,7,8-tetrahydro-2-naphthyl)-[1,1';4',1"]terphenyl-4"-carboxylic acid, 3-methoxymethoxy-2'-(5,5,8,8-tetramethyl-5,6,7,8-tetrahydro-2-naphthyl)-[1,1';4',1"]terphenyl-4"-carboxylic acid, 3-hydroxy-2'-(5,5,8,8-tetramethyl-5,6,7,8-tetrahydro-2-naphthyl)-[1,1';4',1"]terphenyl-4"-carboxylic acid, 3-methoxy-2'-(5,5,8,8-tetramethyl-5,6,7,8-tetrahydro-2-naphthyl)-[1,1';4',1"]terphenyl-4"-carboxylic acid, 2-methoxymethoxy-2'-(5,5,8,8-tetramethyl-5,6,7,8-tetrahydro-2-naphthyl)-[1,1';4',1"]terphenyl-4"-carboxylic acid, 2-hydroxy-2'-(5,5,8,8-tetramethyl-5,6,7,8-tetrahydro-2-naphthyl)-[1,1';4',1"]terphenyl-4"-carboxylic acid, 2-methoxy-2'-(5,5,8,8-tetramethyl-5,6,7,8-tetrahydro-2-naphthyl)-[1,1';4',1"]terphenyl-4"-carboxylic acid, 2'-methoxymethoxy-5'-(5,5,8,8-tetramethyl-5,6,7,8-tetrahydro-2-naphthyl)biphenyl-4-carboxylic acid, 2'-methoxy-5'-(5,5,8,8-tetramethyl-5,6,7,8-tetrahydro-2-naphthyl)biphenyl-4-carboxylic acid, 2'-propyloxy-5'-(5,5,8,8-tetramethyl-5,6,7,8-tetrahydro-2-naphthyl)biphenyl-4-carboxylic acid, 2'-hydroxy-5'-(5,5,8,8-tetramethyl-5,6,7,8-tetrahydro-2-naphthyl)biphenyl-4-carboxylic acid, 4'-(5,5,8,8-tetramethyl-5,6,7,8-tetrahydro-2-naphthyl)-[1,1';2',1"]terphenyl-4"-carboxylic acid, 2'-methoxymethoxy-3'-(5,5,8,8-tetramethyl-5,6,7,8-tetrahydro-2-naphthyl)biphenyl-4-carboxylic acid, 2'-hydroxy-3'-(5,5,8,8-tetramethyl-5,6,7,8-tetrahydro-2-naphthyl)biphenyl-4-carboxylic acid, 2'-methoxy-3'-(5,5,8,8-tetramethyl-5,6,7,8-tetrahydro-2-naphthyl)biphenyl-4-carboxylic acid, 3'-methoxymethoxymethyl-5'-(5,5,8,8-tetramethyl-5,6,7,8-tetrahydro-2-naphthyl)biphenyl-4-carboxylic acid, 3'-hydroxymethyl-5'-(5,5,8,8-tetramethyl-5,6,7,8-tetrahydro-2-naphthyl)biphenyl-4-carboxylic acid, 2'-(4,4-dimethylthiochroman-7-yl)-[1,1';4',1"]terphenyl-4"-carboxylic acid, 2'-(4,4-dimethylthiochroman-6-yl)-[1,1';4',1"]terphenyl-41-carboxylic acid, 2'-(3,5,5,8,8-pentamethyl-5,6,7,8-tetrahydro-2-naphthyl)-[1,1';4',1"]terphenyl-4"-carboxylic acid, 2'-(3-methoxymethoxy-5,5,8,8-tetramethyl-5,6,7,8-tetrahydro-2-naphthyl)-[1,1';4',1"]terphenyl-4"-carboxylic acid, 2'-(3-hydroxy-5,5,8,8-tetramethyl-5,6,7,8-tetrahydro-2-naphthyl)-[1,1';4',1"]terphenyl-4"-carboxylic acid, 2'-(3-methoxy-5,5,8,8-tetramethyl-5,6,7,8-tetrahydro-2-naphthyl)-[1,1';4',1"]terphenyl-4"-carboxylic acid, 2'-(3-propyloxy-5,5,8,8-tetramethyl-5,6,7,8-tetrahydro-2-naphthyl)-[1,1';4',1"]terphenyl-4"-carboxylic acid, 3"-methyl-2'-(5,5,8,8-tetramethyl-5,6,7,8-tetrahydro-2-naphthyl)-[1,1';4',1"]terphenyl-4"-carboxylic acid, 2"-hydroxy-2'-(5,5,8,8-tetramethyl-5,6,7,8-tetrahydro-2-naphthyl)-[1,1';4',1"]terphenyl-4"-carboxylic acid, 2'-methoxymethoxy-2'-(5,5,8,8-tetramethyl-5,6,7,8-tetrahydro-2-naphthyl)-[1,1';4',1"]terphenyl-4"-carboxylic acid, 2"-methoxy-2'-(5,5,8,8-tetramethyl-5,6,7,8-tetrahydro-2-naphthyl)-[1,1';4',1"]terphenyl-4"-carboxylic acid, 2"-propyloxy-2'-(5,5,8,8-tetramethyl-5,6,7,8-tetrahydro-2-naphthyl)-[1,1';4',1"]terphenyl-4"-carboxylic acid, 3"-hydroxy-2'-(5,5,8,8-tetramethyl-5,6,7,8-tetrahydro-2-naphthyl)-[1,1';4',1"]terphenyl-4"-carboxylic acid, 6-[2-(5,5,8,8-tetramethyl-5,6,7,8-tetrahydro-2-naphthyl)biphenyl-4-yl]nicotinic acid, 5-[2-(5,5,8,8-tetramethyl-5,6,7,8-tetrahydro-2-naphthyl)biphenyl-4-yl]-2-pyridinecarboxylic acid, 2'-(5,5,8,8-tetramethyl-5,6,7,8-tetrahydro-2-naphthyl)-[1,1';4',1"]terphenyl-4"-hydroxamic acid, 2'-(5,5,8,8-tetramethyl-5,6,7,8-tetrahydro-2-naphthyl)-[1,1';4',1"]terphenyl-4"-ol,

[2'-(5,5,8,8-tetramethyl-5,6,7,8-tetrahydro-2-naphthyl)-[1,1';4',1"]terphenyl-4"-yl]methanol, 2'-(5,5,8,8-tetramethyl-5,6,7,8-tetrahydro-2-naphthyl)-[1,1';4',1"]terphenyl-4"-carbaldehyde, 4'-methoxycarbonylmethoxy-3'-(5,5,8,8-tetramethyl-5,6,7,8-tetrahydro-2-naphthyl)biphenyl-4-carboxylic acid, 4'-carboxymethoxy-3'-(5,5,8,8-tetramethyl-5,6,7,8-tetrahydro-2-naphthyl)biphenyl-4-carboxylic acid, 4'-(5-ethoxycarbonylpentyloxy)-3'-(5,5,8,8-tetramethyl-5,6,7,8-tetrahydro-2-naphthyl)biphenyl-4-carboxylic acid, 4'-(5-carboxypentyloxy)-3'-(5,5,8,8-tetramethyl-5,6,7,8-tetrahydro-2-naphthyl)biphenyl-4-carboxylic acid, 2'-(5,5,8,8-tetramethyl-5,6,7,8-tetrahydro-2-naphthyl)-[1,1';4',1"]terphenyl-4"-carboxamide, N-ethyl-2'-(5,5,8,8-tetramethyl-5,6,7,8-tetrahydro-2-naphthyl)-[1,1';4',1"]terphenyl-4"-carboxamide, N,N-diethyl-2'-(5,5,8,8-tetramethyl-5,6,7,8-tetrahydro-2-naphthyl)-[1,1';4',1"]terphenyl-4"-carboxamide, morpholin-4-yl-[2'-(5,5,8,8-tetramethyl-5,6,7,8-tetrahydro-2-naphthyl)-[1,1';4',1"]]terphenyl-4"-yl]methanone, (4-hydroxyphenyl)-2'-(5,5,8,8-tetramethyl-5,6,7,8-tetrahydro-2-naphthyl)-[1,1';4',1"]terphenyl-40-carboxamide, 3-(5,5,8,8-tetramethyl-5,6,7,8-tetrahydro-2-naphthyl)biphenyl-4-carboxymethyl-4'-carboxylic acid, 3-(5,5,8,8-tetramethyl-5,6,7,8-tetrahydro-2-naphthyl)biphenyl-4,4'-dicarboxylic acid, 3'-methoxymethoxy-51-(5,5,8,8-tetramethyl-5,6,7,8-tetrahydro-2-naphthyl)biphenyl-4-carboxylic acid, 3'-methoxy-5'-(5,5,8,8-tetramethyl-5,6,7,8-tetrahydro-2-naphthyl)biphenyl-4-carboxylic acid, 3'-propyloxy-5'-(5,5,8,8-tetramethyl-5,6,7,8-tetrahydro-2-naphthyl)biphenyl-4-carboxylic acid, 3'-hydroxy-5'-(5,5,8,8-tetramethyl-5,6,7,8-tetrahydro-2-naphthyl)biphenyl-4-carboxylic acid, 4'-(5,5,8,8-tetramethyl-5,6,7,8-tetrahydro-2-naphthyl)-[1,1';3',1"]terphenyl-4"-carboxylic acid, 4'-(5-carboxamidopentyloxy)-3'-(5,5,8,8-tetramethyl-5,6,7,8-tetrahydro-2-naphthyl)biphenyl-4-carboxylic acid, 3'-methoxycarbonyl-5'-(5,5,8,8-tetramethyl-5,6,7,8-tetrahydro-2-naphthyl)biphenyl-4-carboxylic acid, 3'-carboxyl-5'-(5,5,8,8-tetramethyl-5,6,7,8-tetrahydro-2-naphthyl)biphenyl-4-carboxylic acid, 2'-(4-hydroxy-5,5,8,8-tetramethyl-5,6,7,8-tetrahydro-2-naphthyl)-[1,1';4',1"]terphenyl-4"-carboxylic acid, 2'-(4-methoxy-5,5,8,8-tetramethyl-5,6,7,8-tetrahydro-2-naphthyl)-[1,1';4',1"]terphenyl-4"-carboxylic acid, 2'-(4-propyloxy-5,5,8,8-tetramethyl-5,6,7,8-tetrahydro-2-naphthyl)-[1,1';4',1"]terphenyl-4"-carboxylic acid, 2'-(4-methoxymethoxy-5,5,8,8-tetramethyl-5,6,7,8-tetrahydro-2-naphthyl)-[1,1';4',1"]terphenyl-4"-carboxylic acid, 2-[2-(5,5,8,8-tetramethyl-5,6,7,8-tetrahydro-2-naphthyl)biphenyl-4-yl]-4-thiophenecarboxylic acid.

A subject of the present invention is also the processes for preparing the compounds of formula (I) above according to the reaction schemes given in Tables A and B.

With reference to Table A, the compounds of formula (Ia) can be obtained by a Suzuki-type coupling reaction between a boronic derivative of formula (6) and a biaromatic bromo derivative of formula (7). The boronic derivative of formula (6) is obtained from the halo derivative of formula (5), preferably the bromo or iodo derivative. The biaromatic bromo derivative of formula (7) can be obtained by two different routes involving a Suzuki-type coupling reaction. The first consists in reacting a haloaromatic compound of formula (1) with a bromoboronic derivative of formula (2) and the second consists in reacting an aromatic boronic derivative of formula (3) with an idobromoaromatic derivative of formula (4).

The reaction conditions for these various steps are essentially described in:

N. Miyaura, Synthetic Communications 1981, 11(7), 513–9,

A. Suzuki, Synlett 1990, 221,

A. R. Martin, Acta Chemica Scandinavia 1993, 47, 221–30,

G. Marck, Tetrahedron Letters 1994, vol. 35, No. 20, 3277–80,

T. Wallow, J. Org. Chem. 1994, 59, 5034–7,

H. Zhang, Tetrahedron Letters 1996, vol. 37, No. 7, 1043–4.

The boronic derivatives of formulae (2), (3) and (6) can be prepared according to the following two methods:

(a) either by reaction with butyllithium and then with an alkyl borate, preferably triisopropyl borate or trimethyl borate, followed by hydrolysis with hydrochloric acid, (b) or by reaction with the pinacol ester of the diboronic acid according to the method described by T. Ishiyama, J. Org. Chem. 1995, 60, 7508–10.

Starting with the compound of formula (Ia), it is possible to gain access to the compounds of formulae (Ib) and (Ic).

The compounds of formula (Ib) can be obtained from the compounds of formula (Ia) ($R_5$=OH) by reaction of a halo derivative (9) in the presence of a solvent such as acetone, methyl ketone [sic] or DMF and a base such as potassium carbonate or sodium hydride.

The compounds of formula (Ic) can be obtained from the compounds of formula (Ia) ($R_5$=OH) by standard acylation reaction starting with an acid (10).

The compounds of formula (Id) can be obtained from compounds of formula (Ia) ($R_5$=OH) which are converted, in a first step, into triflate derivatives of formula (8) and then, in a second step, are reacted either under Suzuki-type reaction conditions with an aromatic boronic derivative (12), or under Stille-type reaction conditions with an aromatic stannic derivative (11) according to the method described by A. M. Echavarren, J. Am. Chem. Soc. 1987, 109, 5478–86.

Referring now to Table B, the compounds of formulae (Ie), (If) and (Ig) can be obtained directly from triflate derivatives of formula (8) by carbonylation in the presence of a palladium catalyst and using, respectively, an alcoholic derivative, an amine or a trialkylsilane, according to the methods described by J. K. Stille, Angew Chem. Int., Ed. Engl. 1996, 508–524 and H. Kotsuki, Synthesis 1996, 470–2.

The compounds of formula (Ih) can also be obtained from triflate derivatives of formula (8) by reaction with an acrylic ester (13) in the presence of a palladium catalyst, according to the method described in J. Med. Chem. 1990, vol. 33, No. 7, 1919–24. Starting with the unsaturated compound of formula (Ih), it is possible to gain access directly, by catalytic hydrogenation, to the compound of formula (Ii).

The compounds of formula (Ij) can again be obtained from triflate derivatives of formula (8) by reaction with stannic derivatives such as vinyltributyltin or allyltributyltin (14) in the presence of a palladium catalyst. The intermediate compound obtained of formula (15) is then subjected to an oxidation reaction with osmium tetroxide, under the conditions described in J. Org. Chem. 1990, vol. 55, No. 3, 906–9 and J. Med. Chem. 1991, vol. 34, No. 5, 1614–23.

When, in the compounds of formula (I) according to the invention, $R_1$ represents a —COOH radical, these are prepared according to two different synthetic routes:

(a) The first consists in protecting the carboxylic acid function with a protecting group of alkyl, allyl, benzyl or tert-butyl type.

When the protecting group is an alkyl, the deprotection is obtained using sodium hydroxide or lithium hydroxide in an alcoholic solvent such as methanol, or THF.

When the protecting group is an allyl radical, the deprotection is carried out using a catalyst such as certain transition metal complexes, in the presence of a secondary amine such as morpholine.

When the protecting group is a benzyl radical, the deprotection is carried out in the presence of hydrogen using a catalyst such as palladium on charcoal.

Lastly, when the protecting group is a tert-butyl radical, the deprotection is carried out using trimethylsilane [sic] iodide.

(b) The second consists in starting with the corresponding phenolic compound, which is converted into the triflate, and is then subjected to a carbonylation in the presence of a palladium catalyst.

When, in the compounds of formula (I) according to the invention, $R_1$ represents an alcohol function, these can be obtained:

(a) either from the corresponding aldehyde derivatives by the action of an alkali metal hydride such as sodium borohydride, in an alcoholic solvent such as methanol, (b) or starting with the acid derivatives of formula (Ie) ($R_{10}$=H) by reduction with lithium aluminium hydride.

When, in the compounds of formula (I) according to the invention, $R_1$ represents an aldehyde function, these can be obtained by oxidation of the corresponding alcohols in the presence of manganese oxide, pyridinium dichromate or the Swern reagent.

Lastly, when, in the compounds of formula (I) according to the invention, $R_1$ represents an amide function, these can be obtained by reaction of the acid chlorides, obtained from the corresponding carboxylic acids, with aliphatic, aromatic or heterocyclic amines in the presence of dicyclohexylcarbodiimide or carbonyldiimidazole.

A subject of the present invention is also the compounds of formula (I) as defined above, as medicinal products.

These compounds have agonist or antagonist activity with respect to the expression of one or more biological markers in the test of differentiation of mouse embryonic teratocarcinoma cells (F9) (Skin Pharmacol. 3, p. 256–267, 1990) and/or on the in vitro differentiation of human keratinocytes (Skin Pharmacol. 3, p. 70–85, 1990). These abovementioned tests show the activities of the compounds in the fields of differentiation and proliferation. The activities can also be measured in cellular transactivation tests using RAR recombinant receptors according to the method by B. A. Bernard et al., Biochemical and Biophysical Research Communication, 1992, vol. 186, 977–983.

The compounds according to the invention are particularly suitable in the following fields of treatment:

1) for treating dermatological complaints associated with a keratinization disorder which has a bearing on differentiation and on proliferation, in particular for treating common acne, comedones, polymorphonuclear leukocytes, rosacea, nodulocystic acne, acne conglobata, senile acne and secondary acne such as solar, medication-related or occupational acne, 2) for treating other types of keratinization disorder, in particular ichthyosis, ichthyosiform states, Darier's disease, palmoplantar keratoderma, leucoplasias and leucoplasiform states, and cutaneous or mucous (buccal) lichen, 3) for treating other dermatological complaints associated with a keratinization disorder with an inflammatory and/or immunoallergic component and, in particular, all forms of psoriasis, whether it is cutaneous, mucous or ungual psoriasis and even psoriatic rheumatism, or alternatively cutaneous atopy, such as eczema or respiratory atopy or alternatively gingival hypertrophy; the compounds can also be used in certain inflammatory complaints which have no keratinization disorder;

4) for treating all dermal or epidermal proliferations, whether benign or malignant and whether they are of viral origin or otherwise, such as common warts, flat warts and verruciform epidermodysplasia, it being also possible for the oral or florid papillomatoses and the proliferations to be induced by ultraviolet radiation, in particular in the case of basocellular and spinocellular epithelioma, 5) for treating other dermatological disorders such as bullosis and collagen diseases, 6) for treating certain ophthalmological disorders, in particular corneopathies, 7) for repairing or combating ageing of the skin, whether this is light-induced or chronological ageing, or for reducing actinic keratoses and pigmentations, or any pathologies associated with chronological or actinic ageing, 8) for preventing or curing the stigmata of epidermal and/or dermal atrophy induced by local or systemic corticosteroids, or any other form of cutaneous atrophy, 9) for preventing or treating cicatrization disorders or for preventing or repairing stretch marks, 10) for combating disorders of sebaceous functioning such as the hyperseborrhoea of acne or simple seborrhoea, 11) in the treatment or prevention of cancerous or precancerous states, 12) in the treatment of inflammatory complaints such as arthritis, 13) in the treatment of any general or skin complaint of viral origin, 14) in the prevention or treatment of alopecia, 15) in the treatment of dermatological or general complaints having an immunological component, 16) in the treatment of complaints of the cardiovascular system such as arteriosclerosis.

In the therapeutic fields mentioned above, the compounds according to the invention may be employed advantageously in combination with other compounds of retinoid-type activity, with D vitamins or derivatives thereof, with corticosteroids, with anti-free-radical agents, α-hydroxy or α-keto acids or derivatives thereof, or alternatively with ion-channel blockers. The expression "D vitamins or derivatives thereof" means, for example, vitamin $D_2$ or $D_3$ derivatives and in particular 1,25-dihydroxyvitamin $D_3$. The expression "anti-free-radical agents" means, for example, α-tocopherol, superoxide dismutase or SOD, ubiquinol or certain metal-chelating agents. The expression "α-hydroxy or α-keto acids or derivatives thereof" means, for example, lactic, malic, citric, glycolic, mandelic, tartaric, glyceric or ascorbic acid or the salts, amides or esters thereof. Lastly, the term "ion-channel blockers" means, for example, Minoxidil (2,4-diamino-6-piperidinopyrimidine-3-oxide) and derivatives thereof.

A subject of the present invention is also pharmaceutical compositions containing at least one compound of formula (I) as defined above, one of the optical or geometrical isomers thereof or one of the salts thereof.

The pharmaceutical compositions intended in particular for treating the abovementioned complaints, and are characterized in that they comprise a pharmaceutically acceptable support which is compatible with the mode of administration selected, at least one compound of formula (I), one of the optical or geometrical isomers thereof or one of the salts thereof.

The compounds according to the invention may be administered enterally, parenterally, topically or ocularly.

Via the enteral route, the compositions may be in the form of tablets, gelatin capsules, sugar-coated tablets, syrups, suspensions, solutions, powders, granules, emulsions, microspheres or nanospheres or polymeric or lipid vesicles which enable controlled release. Via the parenteral route, the compositions may be in the form of solutions or suspensions for infusion or for injection.

The compounds according to the invention are generally administered at a daily dose of about 0.01 mg/kg to 100 mg/kg of body weight taken in 1 to 3 doses.

Via the topical route, the pharmaceutical compositions based on compounds according to the invention are more particularly intended for the treatment of the skin and the mucosae and may be in the form of ointments, creams, milks, salves, powders, impregnated pads, solutions, gels, sprays, lotions or suspensions. They may also be in the form of microspheres or nanospheres or polymeric or lipid vesicles or polymeric patches and hydrogels which enable controlled release of the active principle. Furthermore, these topical-route compositions may either be in anhydrous form or in aqueous form, depending on the clinical indication.

Via the ocular route, they are mainly eyedrops.

These compositions for topical or ocular use contain at least one compound of formula (I) as defined above, or one of the optical or geometrical isomers thereof or alternatively one of the salts thereof, at a concentration preferably of between 0.001% and 5% by weight relative to the total weight of the composition.

The compounds of formula (I) according to the invention also find an application in the cosmetic field, in particular in body and hair hygiene and especially for treating skin types with a tendency towards acne, for promoting the regrowth of the hair, for combating hair loss, for combating the greasy appearance of the skin or the hair, in protection against the harmful effects of the sun or in the treatment of physiologically dry skin types, and for preventing and/or combating light-induced or chronological ageing.

In the cosmetic field, the compounds according to the invention can moreover be employed advantageously in combination with other compounds of retinoid-type activity, with D vitamins or derivatives thereof, with corticosteroids, with anti-free-radical agents, α-hydroxy or α-keto acids or derivatives thereof, or alternatively with ion-channel blockers, all of these various products being as defined above.

The present invention is thus also directed towards a cosmetic composition which is characterized in that it comprises, in a cosmetically acceptable support, at least one compound of formula (I) as defined above or one of the optical or geometrical isomers thereof or one of the salts thereof, it being possible for the said cosmetic composition to be, in particular, in the form of a cream, a milk, a lotion, a gel, microspheres or nanospheres or polymeric or lipid vesicles, a soap or a shampoo.

The concentration of compound of formula (I) in the cosmetic compositions according to the invention is advantageously between 0.001% and 3% by weight relative to the entire composition.

The pharmaceutical and cosmetic compositions according to the invention can also contain inert additives or even pharmacodynamically or cosmetically active additives or combinations of these additives and, in particular: wetting agents; depigmenting agents such as hydroquinone, azelaic acid, caffeic acid or kojic acid; emollients; moisturizing agents such as glycerol, PEG-400, thiamorpholinone and derivatives thereof, or urea; anti-seborrhoea or anti-acne agents such as S-carboxymethylcysteine, S-benzylcysteamine, the salts or derivatives thereof, or benzoyl peroxide; antibiotics such as erythromycin and esters thereof, neomycin, clindamycin and esters thereof, and tetra-cyclines; antifungal agents such as ketoconazole or 4,5-polymethylene-3-isothiazolidones; agents for promoting the regrowth of the hair, such as Minoxidil (2,4-diamino-6-piperidinopyrimidine-3-oxide) and derivatives thereof, Diazoxide (7-chloro-3-methyl-1,2,4-benzo-thiadiazine 1,1-dioxide) and Phenytoin (5,4-diphenyl-imidazolidine-2,4-dione); non-steroidal anti-inflammatory agents; carotenoids and, in particular, β-carotene; anti-psoriatic agents such as anthraline and derivatives thereof and, lastly, eicosa-5,8,11,14-tetraynoic acid and eicosa-5,8,11-triynoic acid, the esters and amides thereof.

The compositions according to the invention may also contain flavour-enhancing agents, preserving agents such as para-hydroxybenzoic acid esters, stabilizing agents, moisture regulators, pH regulators, osmotic pressure modifiers, emulsifying agents, UV-A and UV-B screening agents, and antioxidants such as α-tocopherol, butylated hydroxyanisole or butylated hydroxytoluene.

Several examples for obtaining the active compounds of formula (I) according to the invention, as well as various cosmetic and pharmaceutical formulations based on such compounds, will now be given for illustrative purposes and with no limiting nature.

EXAMPLES

Example 1

4-[4-Hydroxy-3-(5,6,7,8-tetrahydro-5,5,8,8-tetramethyl-2-naphthyl)phenyl]benzoic acid (a) 5,6,7,8-Tetrahydro-5,5,8,8-tetramethyl-2-naphthylboronic acid 21.38 g (80.0 mmol) of 5,6,7,8-tetrahydro-5,5,8,8-tetramethyl-2-bromonaphthalene and 50 ml of THF are introduced into a three-necked flask under a stream of nitrogen. 38.4 ml (96.0 mmol) of n-butyllithium (2.5 M in hexane) are added dropwise, at −78° C., and the mixture is stirred for one hour. 27.7 ml (120.0 mmol) of triisopropyl borate are added dropwise at this same temperature and the mixture is stirred for 2 hours. 350 ml of hydrochloric acid (1 N) are added at −50° C. and the mixture is allowed to warm to room temperature. The reaction medium is extracted with dichloromethane and the organic phase is separated out after settling has taken place, dried over magnesium sulphate and evaporated. 18.60 g (100%) of the expected boronic acid are collected in the form of an oil which crystallizes slowly. Melting point 190–192° C.

$^1$H NMR (CDCl$_3$) δ 1.34 (s, 6H), 1.39 (s, 6H), 1.75 (s, 4H), 4.88 (s, 2H), 7.47 (d, 1H, J=7.9 Hz), 7.97 (d, 1H, J=7.9 Hz), 8.21 (s, 1H).

(b) Methyl (or ethyl) 4-(4-hydroxyphenyl)benzoate 10.10 g (47.3 mmol) of 4-(4-hydroxyphenyl)-benzoic acid and 150 ml of methanol (or of ethanol) are introduced into a round-bottomed flask and 2.5 ml of concentrated sulphuric acid are added dropwise. The reaction medium is refluxed for twelve hours and evaporated to dryness. The residue obtained is taken up in a mixture of water and ethyl ether and the organic phase is separated out after settling has taken place, washed with water, dried over magnesium sulphate and evaporated. 10.60 g (98%) of the expected ester are obtained in the form of a colourless oil.

$^1$H NMR (methyl ester) (CDCl$_3$) δ 3.87 (s, 3H), 6.90 (d, 2H, J=8.5 Hz), 7.59 (d, 2H, J=8.6 Hz), 7.74 (d, 2H, J=8.4 Hz), 7.99 (d, 2H, J=8.4 Hz), 9.77 (s, 1H).

(c) Methyl (or Ethyl) 4-(3-bromo-4-hydroxyphenyl)-benzoate 9.35 g (41.0 mmol) of methyl (or ethyl) 4-(4-hydroxyphenyl)benzoate, 125 ml of dioxane and 40 ml of THF are introduced into a round-bottomed flask. 12.19 g (49.1 mmol) of Br$_2$/dioxane complex are added and the mixture is stirred for 24 hours at room temperature. The reaction medium is evaporated to dryness, the residue is taken up in water and ethyl acetate and the organic phase is separated out after settling has taken place, dried over magnesium sulphate and evaporated. The residue obtained is purified by chromatography on a column of silica, eluted with a mixture of ethyl acetate and heptane (20/80). After evaporation of the solvents, 10.80 g (86%) of the expected product are collected in the form of white crystals with a melting point of 145–146° C. (methyl ester).

$^1$H NMR (methyl ester) (CDCl$_3$) δ 3.94 (s, 3H), 5.74 (s, 1H), 7.11 (d, 1H, J=8.5 Hz), 7.49 (dd, 1H, J=8.5/2.1 Hz), 7.58 (d, 2H, J=8.5 Hz), 7.74 (d, 1H, J=2.1 Hz), 8.08 (d, 2H, J=8.5 Hz).

(d) Methyl (or Ethyl) 4-[4-hydroxy-3-(5,6,7,8-tetrahydro-5,5,8,8-tetramethyl-2-naphthyl)phenyl]benzoate 11.41 g (49.1 mmol) of 5,6,7,8-tetrahydro-5,5,8,8-tetramethyl-2-naphthyl boronic acid, 0.06 g (32.7 mmol) of methyl (or ethyl) 4-(3-bromo-4-hydroxyphenyl)benzoate, 640 ml of toluene and 39.3 ml (78.6 mmol) of potassium carbonate solution (2M) are introduced into a three-necked flask. The reaction medium is degassed by bubbling nitrogen through, 69 mg (0.06 mmol) of tetrakistriphenylphosphinepalladium (0) are added and the mixture is heated at 90° C. for twenty hours. The reaction medium is evaporated to dryness and the residue is taken up in water and ethyl ether and acidified. The organic phase is separated out after settling has taken place, dried over magnesium sulphate and evaporated. The residue obtained is purified by chromatography on a column of silica eluted with dichloromethane. 11.57 g (85%) of the expected product are collected in the form of a very pale yellow solid with a melting point of 178–181° C. (methyl ester).

$^1$H NMR (methyl ester) (CDCl$_3$) δ 1.32 (s, 6H), 1.33 (s, 6H), 1.73 (s, 4H), 3.93 (s, 3H), 5.52 (s, 1H), 7.09 (d, 1H, J=9.1 Hz), 7.26 (dd, 1H, J=7.1/1.9 Hz), 7.42 to 7.44 (m, 2H), 7.47 to 7.55 (m, 2H), 7.64 (d, 2H, J=8.4 Hz), 8.08 (d, 2H, J=8.4 Hz).

(e) 4-[4-Hydroxy-3-(5,6,7,8-tetrahydro-5,5,8,8-tetramethyl-2-naphthyl)phenyl]benzoic acid 1.24 g (3.0 mmol) of the methyl (or ethyl) ester obtained in Example 1(d) and 7.5 ml of methanolic sodium hydroxide (4N) are introduced into a round-bottomed flask. The reaction medium is refluxed for four hours, poured into water, acidified and extracted with ethyl ether, and the organic phase is separated out after settling has taken place, dried over magnesium sulphate and evaporated. The residue obtained is chromatographed on a short column of silica, eluted with ethyl ether. 1.00 g (83%) of 4-[4-hydroxy-3-(5,6,7,8-tetrahydro-5,5,8,8-tetramethyl-2-naphthyl)-phenyl] benzoic acid is obtained in the form of white crystals with a melting point of 240–241° C.

$^1$H NMR (CDCl$_3$) δ 1.33 (s, 6H), 1.34 (s, 6H), 1.74 (s, 4H), 7.10 (d, 1H, J=8.7 Hz), 7.26 (dd, 1H, J=7.2/1.8 Hz), 7.42 to 7.48 (m, 2H), 7.54 to 7.58 (m, 2H), 7.69 (d, 2H, J=8.4 Hz), 8.16 (d, 2H, J=8.4 Hz).

Example 2

4-[4-(5-Hydroxypentyloxy)-3-(5,6,7,8-tetrahydro-5,5,8,8-tetramethyl-2-naphthyl)phenyl]benzoic acid (a) Methyl 4-[4-(5-acetoxypentyloxy)-3-(5,6,7,8-tetrahydro-5,5,8,8-tetramethyl-2-naphthyl)phenyl]benzoate 1.66 g (4.0 mmol) of the methyl ester obtained in Example 1(d), 150 ml of acetone and 2.21 g (16.0 mmol) of potassium carbonate are introduced into a round-bottomed flask. 2.67 ml (16.0 mmol) of 5-bromo-pentyl acetate are added and the mixture is refluxed for eight hours. The reaction medium is evaporated to dryness, the residue is taken up in ethyl acetate and water and the organic phase is separated out after settling has taken place, dried over magnesium sulphate and evaporated. 2.20 g (100%) of the expected product are collected in the form of a colourless oil.

$^1$H NMR (CDCl$_3$) δ 1.32 (s, 12H), 1.66 (s, 4H), 1.45 to 2.05 (m, 6H), 3.41 (t, 2H, J=6.7 Hz), 3.93 (s, 3H), 4.04 (t, 2H, J=6.7 Hz), 7.04 (d, 1H, J=8.5 Hz), 7.29 to 7.38 (m, 2H), 7.52 to 7.58 (m, 2H), 7.62 (d, 1H, J=2.4 Hz), 7.66 (d, 2H, J=8.4 Hz), 7.87 (d, 2H, J=8.3 Hz).

(b) 4-[4-(5-Hydroxypentyloxy)-3-(5,6,7,8-tetrahydro-5,5,8,8-tetramethyl-2-naphthyl)phenyl]benzoic acid In a manner similar to that of Example 1(e), starting with 2.20 g (4.0 mmol) of the methyl ester obtained in Example 2(a), and after taking up in an ethyl ether/hexane mixture (10/90) and filtration, 1.45 g (74%) of 4-[4-(5-hydroxypentyloxy)-3-(5,6,7,8-tetrahydro-5,5,8,8-tetramethyl-2-naphthyl)phenyl]-benzoic acid are obtained in the form of a white solid with a melting point of 195–196° C.

$^1$H NMR (CDCl$_3$) δ 1.32 (s, 12H), 1.49 to 1.61 (m, 3H), 1.72 (s, 4H), 1.77 to 1.85 (m, 3H), 3.59 (t, 2H, J=6.1 Hz), 4.03 (t, 2H, J=6.4 Hz), 7.04 (d, 1H, J=8.6 Hz), 7.30 to 7.38 (m, 2H), 7.54 (dd, 1H, J=8.5/2.2 Hz), 7.58 to 7.62 (m, 2H), 7.65 (d, 2H, J=8.4 Hz), 8.10 (d, 2H, J=8.3 Hz).

Example 3

4-[4-(6-Hydroxyhexyloxy)-3-(5,6,7,8-tetrahydro-5,5,8,8-tetramethyl-2-naphthyl)phenyl]benzoic acid (a) Methyl 4-[4-(6-hydroxyhexyloxy)-3-(5,6,7,8-tetrahydro-5,5,8,8-tetramethyl-2-naphthyl)phenyl]benzoate In a manner similar to that of Example 2(a), by reaction of 1.66 g of the methyl ester obtained in Example 1(d) with 2.1 ml (16.0 mmol) of 6-bromohexanol, 2.10 g (100%) of the expected product are obtained in the form of a colourless oil.

$^1$H NMR (CDCl$_3$) δ 1.33 (s, 12H), 1.41 to 1.93 (m, 8H), 1.72 (s, 4H), 3.65 (t, 2H, J=6.3 Hz), 3.93 (s, 3H), 4.02 (t, 2H,

J=6.4 Hz), 7.04 (d, 1H, J=8.5 Hz), 7.30 to 7.38 (m, 2H), 7.54 (dd, 1H, J=8.5/2.3 Hz), 7.59 to 7.62 (m, 2H), 7.66 (d, 2H, J=8.4 Hz), 8.08 (d, 2H, J=8.3 Hz).

(b) 4-[4-(6-Hydroxyhexyloxy)-3-(5,6,7,8-tetrahydro-5,5,8,8-tetramethyl-2-naphthyl)phenyl]benzoic acid In a manner similar to that of Example 1(e), starting with 2.10 g (4.0 mmol) of the methyl ester obtained in Example 3(a), 1.70 g (86%) of 4-[4-(6-hydroxyhexyloxy)-3-(5,6,7,8-tetrahydro-5,5,8,8-tetramethyl-2-naphthyl)phenyl]benzoic acid are obtained in the form of a white solid With a melting point of 200–201° C.

$^1$H NMR (CDCl$_3$) δ 1.33 (s, 12H), 1.38 to 1.83 (m, 8H), 1.72 (s, 4H), 3.59 (t, 2H, J=6.4 Hz), 4.03 (t, 2H, J=6.5 Hz), 7.04 (d, 1H, J=8.6 Hz), 7.30 to 7.38 (m, 2H), 7.54 (dd, 1H, J=8.5/2.3 Hz), 7.60 to 7.62 (m, 2H), 7.65 (d, 2H, J=8.4 Hz), 8.10 (d, 2H, J=8.4 Hz).

Example 4

4-[4-(7-Hydroxyheptyloxy)-3-(5,6,7,8-tetrahydro-5,5,8,8-tetramethyl-2-naphthyl)phenyl]benzoic acid (a) Ethyl 4-[4-(7-hydroxyheptyloxy)-3-(5,6,7,8-tetrahydro-5,5,8,8-tetramethyl-2-naphthyl)phenyl]benzoate In a manner similar to that of Example 2(a), by reaction of 1.50 g (3.5 mmol) of the ethyl ester obtained in Example 1(d) with 1.06 g (5.4 mmol) of 7-bromoheptanol, 1.43 g (75%) of the expected product are obtained in the form of a colourless oil.

$^1$H NMR (CDCl$_3$) δ 1.18 to 1.24 (m, 2H), 1.33 (s, 12H), 1.41 (t, 3H, J=7.1 Hz), 1.52 to 1.58 (m, 4H), 1.72 (s, 4H), 1.72 to 1.82 (m, 4H), 3.60 to 3.64 (m, 2H), 4.02 (t, 2H, J=6.5 Hz), 4.39 (q, 2H, J=7.1 Hz), 7.04 (d, 1H, J=8.5 Hz), 7.32 to 7.38 (m, 2H), 7.54 (dd, 1H, J=8.4/2.4 Hz), 7.59 to 7.63 (m, 2H), 7.65 (d, 2H, J=8.5 Hz), 8.09 (d, 2H, J=8.4 Hz).

(b) 4-[4-(7-Hydroxyheptyloxy)-3-(5,6,7,8-tetrahydro-5,5,8,8-tetramethyl-2-naphthyl)phenyl]benzoic acid In a manner similar to that of Example 1(e), starting with 1.40 g (2.6 mmol) of the ethyl ester obtained in Example 4(a), 1.15 g (87%) of 4-[4-(7-hydroxyheptyloxy)-3-(5,6,7,8-tetrahydro-5,5,8,8-tetramethyl-2-naphthyl)phenyl]benzoic acid are obtained in the form of a white solid with a melting point of 168–172° C.

$^1$H NMR (CDCl$_3$) δ 1.21 to 1.43 (m, 6H), 1.33 (s, 12H), 1.53 to 1.56 (m, 2H), 1.73 (s, 4H), 1.77 to 1.82 (m, 2H), 3.64 (t, 2H, J=6.5 Hz), 4.02 (t, 2H, J=6.5 Hz), 7.05 (d, 1H, J=8.6 Hz), 7.31 to 7.38 (m, 2H), 7.55 (dd, 1H, J=8.5/2.4 Hz), 7.59 (s, 1H), 7.64 (d, 1H, J=2.4 Hz), 7.69 (d, 2H, J=8.4 Hz), 8.16 (d, 2H, J=8.4 Hz)

Example 5

4-[4-(8-Hydroxyoctyloxy)-3-(5,6,7,8-tetrahydro-5,5,8,8-tetramethyl-2-naphthyl)phenyl]benzoic acid (a) Methyl 4-[4-(8-hydroxyoctyloxy)-3-(5,6,7,8-tetrahydro-5,5,8,8-tetramethyl-2-naphthyl)phenyl]benzoate In a manner similar to that of Example 2(a), by reaction of 700 mg (1.7 mmol) of the methyl ester obtained in Example 1(d) with 1.15 ml (6.7 mmol) of 8-bromooctanol, 920 mg (100%) of the expected product are obtained in the form of a colourless oil.

$^1$H NMR (CDCl$_3$) δ 1.33 (s, 12H), 1.38 to 1.83 (m, 12H), 1.72 (s, 4H), 3.64 (t, 2H, J=6.5 Hz), 3.93 (s, 3H), 4.02 (t, 2H, J=6.5 Hz), 7.05 (d, 1H, J=8.6 Hz), 7.52 to 7.67 (m, 4H), 7.69 (d, 2H, J=8.3 Hz), 8.15 (d, 2H, J=8.3 Hz).

(b) 4-[4-(8-Hydroxyoctyloxy)-3-(5,6,7,8-tetrahydro-5,5,8,8-tetramethyl-2-naphthyl)phenyl]benzoic acid In a manner similar to that of Example 1(e), starting with 920 mg (1.7 mmol) of the methyl ester obtained in Example 5(a), 740 mg (83%) of 4-[4-(8-hydroxyoctyloxy)-3-(5,6,7,8-tetrahydro-5,5,8,8-tetramethyl-2-naphthyl)phenyl]benzoic acid are obtained in in the form of pale yellow crystals with a melting point of 155–160° C.

$^1$H NMR (CDCl$_3$) δ 1.33 (s, 12H), 1.38 to 1.83 (m, 12H), 1.72 (s, 4H), 3.64 (t, 2H, J=6.5 Hz), 4.03 (t, 2H, J=6.5 Hz), 7.05 (d, 1H, J=8.6 Hz), 7.52 to 7.67 (m, 4H), 7.69 (d, 2H, J=8.3 Hz), 8.15 (d, 2H, J=8.3 Hz).

Example 6

4-[4-(9-Hydroxynonyloxy)-3-(5,6,7,8-tetrahydro-5,5,8,8-tetramethyl-2-naphthyl)phenyl]benzoic acid (a) Methyl 4-[4-(9-hydroxynonyloxy)-3-(5,6,7,8-tetrahydro-5,5,8,8-tetramethyl-2-naphthyl)phenyl]benzoate In a manner similar to that of Example 2(a), by reaction of 680 mg (1.6 mmol) of the methyl ester obtained in Example 1(d) with 1.47 g (6.6 mmol) of 9-bromononanol, 920 mg (100%) of the expected product are obtained in the form of a brown oil.

$^1$H NMR (CDCl$_3$) δ 1.33 (s, 12H), 1.38 to 1.83 (m, 14H), 1.72 (s, 4H), 3.64 (t, 2H, J=6.5 Hz), 3.93 (s, 3H), 4.02 (t, 2H, J=6.5 Hz), 7.05 (d, 1H, J=8.6 Hz), 7.52 to 7.67 (m, 4H), 7.69 (d, 2H, J=8.3 Hz), 8.15 (d, 2H, J=8.3 Hz).

(b) 4-[4-(9-Hydroxynonyloxy)-3-(5,6,7,8-tetrahydro-5,5,8,8-tetramethyl-2-naphthyl)phenyl]benzoic acid In a manner similar to that of Example 1(e), starting with 920 mg (1.6 mmol) of the methyl ester obtained in Example 6(a), 720 mg (81%) of 4-[4-(9-hydroxynonyloxy)-3-(5,6,7,8-tetrahydro-5,5,8,8-tetramethyl-2-naphthyl)phenyl]benzoic acid are obtained in the form of pale yellow crystals with a melting point of 147–150° C.

$^1$H NMR (CDCl$_3$) δ 1.33 (s, 12H), 1.38 to 1.83 (m, 14H), 1.72 (s, 4H), 3.64 (t, 2H, J=6.5 Hz), 4.03 (t, 2H, J=6.5 Hz), 7.05 (d, 1H, J=8.6 Hz), 7.52 to 7.67 (m, 4H), 7.69 (d, 2H, J=8.3 Hz), 8.15 (d, 2H, J=8.3 Hz).

Example 7

4-[4-Methoxy-3-(5,6,7,8-tetrahydro-5,5,8,8-tetramethyl-2-naphthyl)phenyl]benzoic acid (a) Methyl 4-[4-methoxy-3-(5,6,7,8-tetrahydro-5,5,8,8-tetramethyl-2-naphthyl)phenyl]benzoate 1.66 g (4.0 mmol) of the methyl ester obtained in Example 1(d) and 25 ml of DMF are introduced into a reactor under a stream of nitrogen. 144 mg (4.8 mmol) of sodium hydride (80% in oil) are introduced portionwise and the mixture is stirred until the evolution of gas has ceased. 311 μl (5.0 mmol) of iodomethane are then added and the mixture is stirred for two hours. The reaction medium is poured into water and extracted with ethyl ether, and the organic phase is separated out after settling has taken place, dried over magnesium sulphate and evaporated. The residue obtained is purified by chromatography on a column of silica eluted with dichloromethane. After evaporation of the solvents, 1.70 g (100%) of the expected product are collected in the form of a white crystalline solid.

$^1$H NMR (CDCl$_3$) δ 1.33 (s, 12H), 1.72 (s, 4H), 3.87 (s, 3H), 3.93 (s, 3H), 7.06 (d, 1H, J=8.4 Hz), 7.36 (s, 2H), 7.52 to 7.61 (m, 3H), 7.66 (d, 2H, J=8.3 Hz), 8.09 (d, 2H, J=8.3 Hz).

(b) 4-[4-Methoxy-3-(5,6,7,8-tetrahydro-5,5,8,8-tetramethyl-2-naphthyl)phenyl]benzoic acid In a manner similar to that of Example 1(e), starting with 1.70 g (4.0 mmol) of the methyl ester obtained in Example 7(a), 1.35 g (81%) of 4-[4-methoxy-3-(5,6,7,8-tetrahydro-5,5,8,8-tetramethyl-2-naphthyl)-phenyl]benzoic acid with a melting point of 251–255° C. are obtained.

$^1$H NMR (CDCl$_3$) δ 1.33 (s, 12H), 1.72 (s, 4H), 3.88 (s, 3H), 7.08 (d, 1H, J=8.4 Hz), 7.37 (s, 2H), 7.53 to 7.62 (m, 3H), 7.70 (d, 2H, J=8.2 Hz), 8.17 (d, 2H, J=8.2 Hz).

Example 8

4-[4-Methoxyethoxymethoxy-3-(5,6,7,8-tetrahydro-5,5,8,8-tetramethyl-2-naphthyl)phenyl]benzoic acid (a) Methyl 4-[4-methoxyethoxymethoxy-3-(5,6,7,8-tetrahydro-5,5,8,8-tetramethyl-2-naphthyl)phenyl]benzoate In a manner similar to that of Example 2(a), by reaction of 1.66 g (4.0 mmol) of the methyl ester obtained in Example 1(d) with 571 µl (5.0 mmol) of methoxyethoxymethyl chloride, 1.99 g (99%) of the expected product are obtained in the form of a white crystalline solid.

$^1$H NMR (CDCl$_3$) δ 1.32 (s, 12H), 1.72 (s, 4H), 3.37 (d, 3H, J=0.5 Hz), 3.52 (t, 2H, J=3.9 Hz), 3.77 (t, 2H, J=3.9 Hz), 3.93 (s, 3H), 5.26 (s, 2H), 7.30 to 7.37 (m, 3H), 7.51 to 7.60 (m, 3H), 7.65 (d, 2H, J=8.2 Hz), 8.09 (d, 2H, J=8.1 Hz).

(b) 4-[4-Methoxyethoxymethoxy-3-(5,6,7,8-tetrahydro-5,5,8,8-tetramethyl-2-naphthyl)phenyl]benzoic acid In a manner similar to that of Example 1(e), starting with 1.99 g (4.0 mmol) of the methyl ester obtained in Example 8(a), 1.62 g (84%) of 4-[4-methoxyethoxymethoxy-3-(5,6,7,8-tetrahydro-5,5,8,8-tetramethyl-2-naphthyl)phenyl]benzoic acid are obtained in the form of a white crystalline solid with a melting point of 218–219° C.

$^1$H NMR (CDCl$_3$) δ 1.32 (s, 12H), 1.72 (s, 4H), 3.37 (s, 3H), 3.52 (t, 2H, J=3.9 Hz), 3.76 (t, 2H, J=3.9 Hz), 5.26 (s, 2H), 7.30 to 7.37 (m, 3H), 7.50 to 7.61 (m, 3H), 7.65 (d, 2H, J=8.3 Hz), 8.11 (d, 2H, J=8.3 Hz).

Example 9

4-[4-Benzyloxy-3-(5,6,7,8-tetrahydro-5, 5, 8, 8-tetramethyl-2-naphthyl)phenyl]benzoic acid (a) Ethyl 4-[4-benzyloxy-3-(5,6,7,8-tetrahydro-5,5,8,8-tetramethyl-2-naphthyl)phenyl]benzoate In a manner similar to that of Example 2(a), by reaction of 1.20 g (2.8 mmol) of the ethyl ester obtained in Example 1(d) with 400 µl (3.2 mmol) of benzyl bromide, 1.23 g (85%) of the expected product are obtained in the form of a colourless oil.

$^1$H NMR (CDCl$_3$) δ 1.23 (s, 6H), 1.32 (s, 6H), 1.41 (t, 3H, J=7.1 Hz), 1.70 (s, 4H), 4.39 (q, 2H, J=7.1 Hz), 5.38 (s, 2H), 7.11 (d, 1H, J=8.5 Hz), 7.28 to 7.36 (m, 6H), 7.53 (dd, 1H, J=8.5/2.4 Hz), 7.58 to 7.64 (m, 2H), 7.65 (d, 2H, J=8.4 Hz), 8.09 (d, 2H, J=8.4 Hz).

(b) 4-[4-Benzyloxy-3-(5,6,7,8-tetrahydro-5,5,8,8-tetramethyl-2-naphthyl)phenyl]benzoic acid In a manner similar to that of Example 1(e), starting with 1.20 g (2.3 mmol) of the ethyl ester obtained in Example 9(a), 970 mg (86%) of 4-[4-benzyloxy-3-(5,6,7,8-tetrahydro-5,5,8,8-tetramethyl-2-naphthyl)phenyl]benzoic acid are obtained in the form of a white crystalline solid with a melting point of 241–244° C.

$^1$H NMR (CDCl$_3$) δ 1.23 (s, 6H), 1.32 (s, 6H), 1.70 (s, 4H), 5.13 (s, 2H), 7.12 (d, 1H, J=8.6 Hz), 7.28 to 7.36 (m, 6H), 7.54 (dd, 1H, J=8.5/2.4 Hz), 7.58 (s, 1H), 7.64 (s, 1H), 7.66 (d, 2H, J=8.4 Hz), 8.11 (d, 2H, J=8.4 Hz).

Example 10

4'-(2,3-Dihydroxypropoxy)-3'-(5,5,8,8-tetramethyl-5,6,7,8-tetrahydro-2-naphthyl)biphenyl-4-carboxylic acid (racemic)

(a) 2,2-Dimethyl-[1,3]dioxolan-4-ylmethyl 4-toluene-sulphonate (racemic)

5.29 g (40.0 mmol) of (2,2-dimethyl-[1,3]dioxolan-4-yl) methanol (Solketal®) and 10 ml of pyridine are introduced into a round-bottomed flask under an argon atmosphere. The mixture is cooled to 0° C., 8.39 g (44.0 mmol) of para-toluenesulphonic acid are added and the mixture is stirred for sixteen hours at room temperature. The reaction medium is poured into a 1N HCl/ethyl ether mixture, extracted with ethyl ether, washed with water, dried over magnesium sulphate and evaporated. The residue obtained is purified by chromatography on a column of silica eluted with dichloromethane. After evaporation of the solvents, 9.70 g (85%) of the expected product are collected in the form of yellow crystals with a melting point of 45–47° C.

$^1$H NMR (CDCl$_3$) δ 1.31 (s, 3H), 1.34 (s, 3H), 2.45 (s, 3H), 3.74 to 3.80 (m, 1H), 3.93 to 4.07 (m, 3H), 4.23 to 4.32 (m, 1H), 7.35 (d, 2H, J=8.1 Hz), 7.80 (d, 2H, J=8.2 Hz).

(b) Ethyl 4'-(2,2-dimethyl-[1,3]dioxolan-4-yl-methoxy)-3'-(5,5,8,8-tetramethyl-5,6,7,8-tetrahydro-2-naphthyl)biphenyl-4-carboxylate (racemic)

3.00 g (7.0 mmol) of the ethyl ester obtained in Example 1(d), 2.41 g (8.4 mmol) of the tosylate obtained in Example 10(a), 1.10 g (7.7 mmol) of potassium carbonate and 35 ml of DMF are introduced into a round-bottomed flask under an argon atmosphere. The reaction medium is heated for one hour at 100° C., cooled, poured into a water/ethyl ether mixture, extracted with ethyl ether, washed with water, dried over magnesium sulphate and evaporated. The residue obtained is purified by chromatography on a column of silica eluted with a mixture composed of 50% dichloromethane and 50% heptane. After evaporation of the solvents, 2.66 g (70%) of the expected product are collected in the form of a colourless oil.

¹H NMR (CDCl₃) δ 1.32 (s, 6H), 1.33 (s, 6H), 1.36 (s, 6H), 1.41 (t, 3H, J=7.1 Hz), 1.72 (s, 4H), 3.83 (dd, 1H, J=8.4/6.0 Hz), 3.94 to 4.07 (m, 2H), 4.14 (dd, 1H, J=9.5/4.9 Hz), 4.39 (q, 2H, J=7.1 Hz), 4.40 (q, 1H, J=5.1 Hz), 7.06 (d, 1H, J=8.5 Hz), 7.28 (dd, 1H, J=8.1/1.8 Hz), 7.36 (d, 1H, J=8.2 Hz), 7.53 (d, 1H, J=1.8 Hz), 7.55 (dd, 1H, J=8.5/2.3 Hz), 7.61 (d, 1H, J=2.4 Hz), 7.65 (d, 2H, J=8.4 Hz), 8.09 (d, 2H, J=8.4 Hz).

(c) Ethyl 4'-(2,3-dihydroxypropoxy)-3'-(5,5,8,8-tetramethyl-5,6,7,8-tetrahydro-2-naphthyl)biphenyl-4-carboxylate (racemic)

1.66 g (3.2 mmol) of the ester obtained in Example 10(b), 6.12 g (32.2 mmol) of para-toluene-sulphonic acid, 60 ml of dichloromethane and 5 ml of THF are introduced into a round-bottomed flask under an argon atmosphere. The reaction medium is stirred for sixteen hours at room temperature, poured into a water/ethyl ether mixture, extracted with ethyl ether, washed with water, dried over magnesium sulphate and evaporated. The residue obtained is purified by chromatography on a cake of silica eluted with a mixture composed of 40% ethyl acetate and 60% heptane. After evaporation of the solvents, 1.16 g (72%) of the expected product are collected in the form of a white powder with a melting point of 56° C.

¹H NMR (CDCl₃) δ 1.33 (s, 12H), 1.41 (t, 3H, J=7.1 Hz), 1.73 (s, 4H), 1.87 (t, 1H, J—6.3 Hz), 2.49 (d, 1H, J=4.3 Hz), 3.60 to 3.80 (m, 2H); 4.03 to 4.16 (m, 3H), 4.40 (q, 2H, J=7.1 Hz), 7.07 (d, 1H, J=8.4 Hz), 7.29 (d, 1H, J=1.8 Hz), 7.38 (d, 1H, J=8.1 Hz), 7.48 (d, 1H, J=1.8 Hz), 7.54 to 7.60 (m, 2H), 7.65 (d, 2H, J=8.4 Hz), 8.10 (d, 2H, J=8.5 Hz).

(d) 4'-(2,3-Dihydroxypropoxy)-3'-(5,5,8,8-tetramethyl-5,6,7,8-tetrahydro-2-naphthyl)biphenyl-4-carboxylic acid (racemic)

In a manner similar to Example 1(e), starting with 1.16 g (2.3 mmol) of the ethyl ester obtained in Example 10(c), 897 mg (82%) of 4'-(2,3-dihydroxypropoxy)-3'-(5,5,8,8-tetramethyl-5,6,7,8-tetrahydro-2-naphthyl)biphenyl-4-carboxylic acid are obtained in the form of a white crystalline solid with a melting point of 258° C.

¹H NMR (CDCl₃+2 drops of DMSO-d₆) δ 1.12 (s, 12H), 1.52 (s, 4H), 3.38 to 3.53 (m, 2H), 3.79 to 3.94 (m, 3H), 6.91 (d, 1H, J=8.4 Hz), 7.10 to 7.17 (m, 2H), 7.34 to 7.39 (m, 3H), 7.45 (d, 2H, J=8.4 Hz), 7.88 (d, 2H, J=8.4 Hz).

Example 11

4'-(2,2-Dimethyl)-[1,3]dioxolan-4-ylmethoxy)-3'-(5,5,8,8-tetramethyl-5,6,7,8-tetrahydro-2-naphthyl)-biphenyl-4-carboxylic acid (racemic)

In a manner similar to that of Example 1(e), starting with 1.00 g (1.8 mmol) of the ester obtained in Example 10(b), 805 mg (85%) of 4'-(2,2-dimethyl)-[1,3]dioxolan-4-ylmethoxy)-3'-(5,5,8,8-tetramethyl-5,6,7,8-tetrahydro-2-naphthyl)biphenyl-4-carboxylic acid are obtained in the form of a white crystalline solid with a melting point of 206° C.

¹H NMR (CDCl₃) δ 1.33 (s, 12H), 1.36 (s, 6H), 1.73 (s, 4H), 3.84 (dd, 1H, J=8.4/6.0 Hz), 3.96 to 4.09 (m, 2H), 4.15 (dd, 1H, J=9.5/4.9 Hz), 4.42 (q, 1H, J=5.1 Hz), 7.08 (d, 1H, J=8.6 Hz), 7.29 (dd, 1H, J=8.1/1.7 Hz), 7.36 (d, 1H, J=8.2 Hz), 7.54 (d, 1H, J=1.6 Hz), 7.57 (dd, 1H, J=8.5/2.3 Hz), 7.63 (d, 1H, J=2.3 Hz), 7.69 (d, 2H, J=8.4 Hz), 8.17 (d, 2H, J=8.4 Hz).

Example 12

4'-(2-Morpholin-4-ylethoxy)-3'-(5,5,8,8-tetramethyl-5,6,7,8-tetrahydro-2-naphthyl)biphenyl-4-carboxylic acid (a) Ethyl 4'-(2-morpholin-4-ylethoxy)-3'-(5,5,8,8-tetramethyl-5,6,7,8-tetrahydro-2-naphthyl)biphenyl-4-carboxylate In a manner similar to that of Example 2(a), by reaction of 1.08 g (2.5 mmol) of the ethyl ester obtained in Example 1(d) with 1.39 g (7.5 mmol) of 4-(2-chloroethyl)morpholine hydrochloride, 500 mg (37%) of the expected product are obtained in the form of a colourless oil.

¹H NMR (CDCl₃) δ 1.32 (s, 12H), 1.41 (t, 3H, J=7.1 Hz), 1.72 (s, 4H), 2.45 (t, 2H, J=4.6 Hz), 2.77 (t, 2H, J=5.8 Hz), 3.64 (t, 2H, J=4.7 Hz), 4.16 (t, 2H, J=5.8 Hz), 4.40 (q, 2H, J=7.2 Hz), 7.05 (d, 1H, J=8.5 Hz), 7.34 (s, 2H), 7.52 (s, 1H), 7.56 (dd, 1H, J=8.4/2.4 Hz), 7.61 (d, 1H, J=2.3 Hz), 7.65 (d, 2H, J=8.4 Hz), 8.09 (d, 2H, J=8.4 Hz).

(b) 4'-(2-Morpholin-4-ylethoxy)-3'-(5,5,8,8-tetramethyl-5,6,7,8-tetrahydro-2-naphthyl)biphenyl-4-carboxylic acid In a manner similar to that of Example 1(e), starting with 500 mg (0.92 mmol) of the ethyl ester obtained in Example 12(a), 320 mg (70%) of 4'-(2-morpholin-4-ylethoxy)-3'-(5,5,8,8-tetramethyl-5,6,7,8-tetrahydro-2-naphthyl)biphenyl-4-carboxylic acid are obtained in the form of a white crystalline solid with a melting point of 270–272° C.

¹H NMR (CDCl₃+2 drops of DMSO-d₆) δ 1.31 (s, 12H), 1.73 (s, 4H), 2.58 to 2.61 (m, 2H), 3.23 (d, 2H, J=11.9 Hz), 3.38 (br s, 2H), 3.67 (d, 2H, J=12.6 Hz), 4.02 (t, 2H, J=11.9 Hz), 4.61 (br s, 2H), 7.08 (d, 1H, J=8.3 Hz), 7.22 (dd, 1H, J=8.1/1.6 Hz), 7.35 (d, 1H, J=8.1 Hz), 7.47 (s, 1H), 7.55 (s, 1H), 7.61 (dd, 1H, J=8.1/2.4 Hz), 7.64 (d, 2H, J=8.4 Hz), 8.09 (d, 2H, J=8.3 Hz).

Example 13

Methyl 2'-(5,5,8,8-tetramethyl-5,6,7,8-tetrahydro-2-naphthyl)-[1,1';4',1"]terphenyl-4"-carboxylate (a) Methyl 3'-(5,5,8,8-tetramethyl-5,6,7,8-tetrahydro-2-naphthyl)-4'-trifluoromethanesulphonyloxy-biphenyl-4-carboxylate 1.66 g (4.0 mmol) of the methyl ester obtained in Example 1(d), 1.56 g (12.8 mmol) of 4-dimethylaminopyridine and 40 ml of dichloromethane are introduced into a three-necked flask under a stream of nitrogen. The mixture is cooled to 0° C., 701 μl (4.2 mmol) of trifluoromethanesulphonic anhydride are added dropwise and this mixture is stirred at room temperature for one hour. The reaction medium is poured into a mixture of hydrochloric acid (1N) and dichloromethane, and the organic phase is separated out after settling has taken place, dried over magnesium sulphate and evaporated. The residue obtained is purified by chromatography on a column of silica eluted with a mixture of dichloromethane and hexane (40/60). 1.90 g (87%) of the expected product are collected in the form of a colourless oil.

¹H NMR (CDCl₃) δ 1.31 (s, 6H), 1.32 (s, 6H), 1.73 (s, 4H), 3.95 (s, 3H), 7.23 (dd, 1H, J=8.2/1.8 Hz), 7.39 to 7.48 (m, 3H), 7.60 to 7.70 (m, 2H), 7.72 (d, 2H, J=8.5 Hz), 8.13 (d, 2H, J=8.3 Hz).

(b) Methyl 2'-(5,5,8,8-tetramethyl-5,6,7,8-tetrahydro-2-naphthyl)-[1,1';4',1"]terphenyl-4"-carboxylate 469 mg (3.8 mmol) of phenylboronic acid, 1.91 g (3.5 mmol) of methyl 4-[4-trifluoromethanesulphonate-3-(5,6,7,8-tetrahydro-5,5,8,8-tetramethyl-2-naphthyl)-phenyl]benzoate, 4.54 ml (9.1 mmol) of sodium carbonate solution (2M), 296 mg of lithium chloride and 30 ml of DMF are introduced into a three-necked flask. The reaction medium is degassed by bubbling nitrogen through, 129 mg (0.11 mmol) of tetrakistriphenylphosphinepalladium(0) are added and this mixture is heated at 90° C. for twenty hours. The reaction medium is evaporated to dryness and the residue is taken up in water and ethyl ether and acidified. The organic phase is separated out after settling has taken place, dried over magnesium sulphate and evaporated. The residue obtained is purified by chromatography on a column of silica eluted with a mixture of ethyl ether and heptane (5/95). 480 mg (30%) of the expected product are collected in the form of a yellow oil.

$^1$H NMR (CDCl$_3$) δ 0.90 (s, 6H), 1.26 (s, 6H), 1.55 to 1.63 (m, 4H), 3.90 (s, 3H), 6.90 (d, 1H, J=1.7 Hz), 7.14 to 7.28 (m, 7H), 7.49 (d, 1H, J=8.0 Hz), 7.62 (dd, 1H, J=8.0/1.9 Hz), 7.70 to 7.73 (m, 1H), 7.71 (d, 2H, J=8.4 Hz), 8.11 (d, 2H, J=8.4 Hz).

Example 14

2'-(5,5,8,8-Tetramethyl-5,6,7,8-tetrahydro-2-naphthyl)-[1,1';4',1"]terphenyl-4"-carboxylic acid In a manner similar to that of Example 1(e), starting with 950 mg (2.0 mmol) of the methyl ester obtained in Example 13(b), 820 mg (89%) of 2'-(5,5,8,8-tetramethyl-5,6,7,8-tetrahydro-2-naphthyl)-[1,1';4',1"]terphenyl-4"-carboxylic acid are collected in the form of a white powder with a melting point of 287–288° C.

$^1$H NMR (CDCl$_3$) δ 0.91 (s, 6H), 1.27 (s, 6H), 1.56 to 1.64 (m, 4H), 6.89 (d, 1H, J=1.8 Hz), 7.14 to 7.33 (m, 7H), 7.52 (d, 1H, J=7.9 Hz), 7.67 (dd, 1H, J=8.0/1.9 Hz), 7.72 to 7.73 (m, 1H), 7.75 (d, 2H, J=8.6 Hz), 8.15 (d, 2H, J=8.4 Hz).

Example 15

4-(Methoxymethoxy-2'-(5,5,8,8-tetramethyl-5,6,7,8-tetraydro-2-naphthyl)-[1,1';4',1"]terphenyl-4"-carboxylic acid

(a) 4-Methoxymethoxybromobenzene

In a manner similar to that of Example 7(a), by reaction of 48.84 g (282.3 mmol) of 4-bromophenol with 25.0 ml (310.5 mmol) of chloromethyl methyl ether, 63.85 g (100%) of the expected product are obtained in the form of a beige-coloured oil.

$^1$H NMR (CDCl$_3$) δ 3.46 (s, 3H), 5.14 (s, 2H), 6.92 (d, 2H, J=9.0 Hz), 7.38 (d, 2H, J=9.0 Hz).

(b) 4-Methoxymethoxyphenylboronic acid

In a manner similar to that of Example 1(a), starting with 63.81 g (293.0 mmol) of 4-methoxymethoxybromobenzene, 35.42 g (80%) of the expected product are obtained in the form of a white solid with a melting point of 122° C.

$^1$H NMR (CDCl$_3$) δ 3.52 (s, 3H), 5.27 (s, 2H), 7.15 (d, 2H, J=8.6 Hz), 8.16 (d, 2H, J=8.6 Hz).

(c) Ethyl 4-methoxymethoxy-2'-(5,5,8,8-tetramethyl-5,6,7,8-tetrahydro-2-naphthyl)-[1,1';4',1"]terphenyl-4"-carboxylate In a manner similar to that of Example 13 (b), by reaction of 357 mg (2.0 mmol) of the compound obtained in Example 15(b) with 1.00 g (1.8 mmol) of the analogue (ethyl ester) of the compound obtained in Example 13(a), 880 mg (13%) of the expected product are obtained in the form of a colourless oil.

$^1$H NMR (CDCl$_3$) δ 0.94 (s, 6H), 1.28 (s, 6H), 1.42 (t, 3H, J=7.1 Hz), 1.58 to 1.63 (m, 4H), 3.46 (s, 3H), 4.41 (q, 2H, J=7.1 Hz), 5.14 (s, 2H), 6.90 (d, 1H, J=1.8 Hz), 6.91 (d, 2H, J=8.7 Hz), 7.08 (d, 2H, J=8.7 Hz), 7.17 (dd, 1H, J=8.1/1.9 Hz), 7.29 (d, 1H, J=8.1 Hz), 7.50 (d, 1H, J=7.9 Hz), 7.64 (dd, 1H, J=8.0/2.0 Hz), 7.72 (d, 1H, J=1.9 Hz), 7.74 (d, 2H, J=8.4 Hz), 8.13 (d, 2H, J=8.4 Hz).

(d) 4-Methoxymethoxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 870 mg (1.6 mmol) of the ethyl ester obtained in Example 15(c), 750 mg (91%) of 4-methoxymethoxy-2'-(5,5,8,8-tetramethyl-5,6,7,8-tetrahydro-2-naphthyl)-[1,1';4',1"]terphenyl-4"-carboxylic acid are collected in the form of a white powder with a melting point of 249–251° C.

$^1$H NMR (CDCl$_3$+2 drops of DMSO-d$_6$) δ 0.94 (s, 6H), 1.28 (s, 6H), 1.54 to 1.66 (m, 4H), 3.45 (s, 3H), 5.14 (s, 2H), 6.89 (d, 1H, J=1.9 Hz), 6.91 (d, 2H, J=8.6 Hz), 7.08 (d, 2H, J=8.6 Hz), 7.17 (dd, 1H, J=8.1/1.7 Hz), 7.31 (d, 1H, J=8.1 Hz), 7.28 (d, 1H, J=8.1 Hz), 7.50 (d, 1H, J=7.9 Hz), 7.65 (dd, H, J=8.0/1.8 Hz), 7.71 (d, 1H, J=1.9 Hz), 7.74 (d, 2H, J=8.3 Hz), 8.14 (d, 2H, J=8.3 Hz).

Example 16

4-Hydroxy-2'-(5,5,8,8-tetramethyl-5, 6,7,8-tetrahydro-2-naphthyl)-[1,1';4',1"]terphenyl-4"-carboxylic acid

(a) Ethyl 4-hydroxy-2'-(5,5,8,8-tetramethyl-5,6,7,8-tetrahydro-2-naphthyl)-[1,1';4',1"]terphenyl-4"-carboxylate 3.81 g (5.5 mmol) of the compound obtained in Example 15(c), 100 ml of ethanol and 50 ml of THF are introduced into a 250 ml three-necked flask under a stream of nitrogen. 3.5 ml of concentrated sulphuric acid are added dropwise. The reaction medium is heated for fifteen minutes at 60° C., water is then added, the mixture is extracted with ethyl ether and the organic phase is washed with water to neutral pH, dried over magnesium sulphate and filtered, and the solvents are evaporated off. The residue obtained is purified by chromatography on a column of silica eluted with heptane and then with a mixture composed of 20% ethyl acetate and 80% heptane. After evaporation of the solvents, 2.60 g (74%) of the expected compound are collected in the form of a white powder with a melting point of 177–179° C.

$^1$H NMR (CDCl$_3$) δ 0.98 (s, 6H), 1.27 (s, 6H), 1.42 (t, 3H, J=7.1 Hz), 1.58 to 1.65 (m, 4H), 4.41 (q, 2H, J=7.1 Hz), 4.91 (s, 1H), 6.71 (d, 2H, J=8.6 Hz), 6.94 (d, 1H, J=1.8 Hz), 7.03 (d, 2H, J=8.6 Hz), 7.13 (dd, 1H, J=8.1/1.9 Hz), 7.27 (d, 2H, J=7.4 Hz), 7.49 (d, 1H, J=8.0 Hz), 7.64 (dd, 1H, J=8.0/1.9 Hz), 7.71 (d, 1H, J=1.9 Hz), 7.73 (d, 2H, J=8.5 Hz), 8.13 (d, 2H, J=8.4 Hz).

(b) 4-Hydroxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 980 mg (1.9 mmol) of the ethyl ester obtained in Example 16(a), 790 mg (80%) of 4-hydroxy-2'-(5,5,8,8-tetramethyl-5,6,7,8-tetrahydro-2-naphthyl)-[1,1';4',1"]terphenyl-41-carboxylic acid are collected in the form of a white powder with a melting point of 262–266° C.
¹H NMR (CDCl₃) δ 0.99 (s, 6H), 1.27-(s, 6H), 1.55 to 1.67 (m, 4H), 6.72 (d, 2H, J=8.5 Hz), 6.97 (d, 1H, J=1.7 Hz), 6.98 (d, 2H, J=8.5 Hz), 7.12 (dd, 1H, J=8.0/1.6 Hz), 7.25 (d, 1H, J=8.1 Hz), 7.49 (d, 1H, J=7.9 Hz), 7.64 (dd, 1H, J=8.0/1.6 Hz), 7.69 (d, 1H, J=1.7 Hz), 7.73 (d, 2H, J=8.3 Hz), 8.13 (d, 2H, J=8.3 Hz).

Example 17

4-Methoxy-2'-(5,5,8,8-tetramethyl-5,6,7,8-tetrahydro-2-naphthyl)-[1,1';4',1"]terphenyl-4"-carboxylic acid

(a) Ethyl 4-methoxy-2'-(5,5,8,8-tetramethyl-5,6,7,8-tetrahydro-2-naphthyl)-[1,1';4',1"]terphenyl-4"-carboxylate In a manner similar to that of Example 7(a), by reaction of 1.40 g (2.8 mmol) of the compound obtained in Example 16(a) with 250 μl (4.2 mmol) of methyl iodide, 1.35 g (96%) of the expected product are obtained in the form of a yellow solid with a melting point of 112–115° C.
¹H NMR (CDCl₃) δ 1.27 (s, 12H), 1.42 (t, 3H, J=7.1 Hz), 1.58 to 1.65 (m, 4H), 3.78 (s, 3H); 4.41 (q, 2H, J=7.1 Hz), 6.78 (d, 2H, J=8.7 Hz), 6.93 (d, 1H, J=1.9 Hz), 7.08 (d, 2H, J=8.7 Hz), 7.14 (dd, 1H, J=8.1/1.9 Hz), 7.27 (d, 1H, J=7.0 Hz), 7.50 (d, 1H, J=7.9 Hz), 7.64 (dd, 1H, J=8.0/4.0 Hz), 7.71 (d, 1H, J=1.9 Hz), 7.74 (d, 2H, J=8.5 Hz), 8.12 (d, 2H, J=8.4 Hz).

(b) 4-Methoxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 1.30 g (2.7 mmol) of the ethyl ester obtained in Example 17(a), 960 mg (74%) of 4-methoxy-2'-(5,5,8,8-tetramethyl-5,6,7,8-tetrahydro-2-naphthyl)-[1,1';4',1"]terphenyl-41-carboxylic acid are collected in the form of a white powder with a melting point of 262–266° C.
¹H NMR (CDCl₃) δ 0.96 (s, 6H), 1.27 (s, 6H), 1.55 to 1.67 (m, 4H), 3.78 (s, 3H), 6.78 (d, 2H, J=8.7 Hz), 6.93 (d, 1H, J=1.6 Hz), 7.08 (d, 2H, J=8.6 Hz), 7.14 (dd, 1H, J=8.2/1.7 Hz), 7.27 (d, 1H, J=8.1 Hz), 7.50 (d, 1H, J=8.0 Hz), 7.65 (dd, 1H, J=8.0/1.8 Hz), 7.72 (d, 1H, J=1.6 Hz), 7.75 (d, 2H, J=8.4 Hz), 8.17 (d, 2H, J=8.3 Hz).

Example 18

3-Methoxymethoxy-2'-(5,5,8,8-tetramethyl-5,6,7,8-tetramethyl-5,6,7,8-tetrahydro-2-naphthyl)-[1,1';4',1"]terphenyl-4"-carboxylic acid

(a) 3-Methoxymethoxybromobenzene

In a manner similar to that of Example 7(a), by reaction of 100.00 g (577.9 mmol) of 3-bromophenol with 48.28 g (635.8 mmol) of chloromethyl methyl ether, 135.32 g (100%) of the expected product are obtained in the form of a pale beige oil.
¹H NMR (CDCl₃) δ 3.46 (s, 3H), 5.15 (s, 2H), 6.92 to 7.00 (m, 1H), 7.10 to 7.14 (m, 2H), 7.18 to 7.22 (m, 1H).

(b) 3-Methoxymethoxyphenylboronic acid

In a manner similar to that of Example 1(a), starting with 125.00 g (575.8 mmol) of 3-methoxymethoxybromobenzene, 86.00 g (100%) of the expected product are obtained in the form of a yellow oil which will be used directly for the following step.

(c) Ethyl 3-methoxymethoxy-2'-(5,5,8,8-tetramethyl-5,6,7,8-tetrahydro-2-naphthyl)-[1,1';4',1"]terphenyl-4"-carboxylate In a manner similar to that of Example 13 (b), by reaction of 3.50 g (19.3 mmol) of the compound obtained in Example 18(b) with 9.00 g (16.1 mmol) of the analogue (ethyl ester) of the compound obtained in Example 13(a), 7.70 g (87%) of the expected product are obtained in the form of a white solid with a melting point of 103–104° C.
¹H NMR (CDCl₃) δ 0.96 (s, 6H), 1.27 (s, 6H), 1.42 (t, 3H, J=7.1 Hz), 1.58 to 1.65 (m, 4H), 3.36 (s, 3H), 4.41 (q, 2H, J=7.1 Hz), 4.89 (s, 2H), 6.76 (t, 1H, J=2.1 Hz), 6.85 (dd, 1H, J=8.2/2.4 Hz), 6.91 (m, 1H) 6.93 (d, 1H, J=1.6 Hz), 7.13 to 7.30 (m, 3H), 7.54 (d, 1H, J=7.9 Hz), 7.65 (dd, 1H, J=8.0/1.9 Hz), 7.72 (s, 1H), 7.74 (d, 2H, J=8.4 Hz), 8.13 (d, 2H, J=8.4 Hz).

(d) 3-Methoxymethoxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 1.20 g (2.2 mmol) of the ethyl ester obtained in Example 18(c), 1.03 g (90%) of 3-methoxymethoxy-2'-(5,5,8,8-tetramethyl-5,6,7,8-tetrahydro-2-naphthyl)-[1,1';4',1"]terphenyl-4"-carboxylic acid are collected in the form of a white powder with a melting point of 212° C.
¹H NMR (CDCl₃) δ 0.96 (s, 6H), 1.27 (s, 6H), 1.56 to 1.66 (m, 4H), 3.37 (s, 3H), 4.90 (s, 2H), 6.77 (d, 1H, J=1.9 Hz), 6.85 (dd, 1H, J=8.2/1.9 Hz), 6.91 to 6.94 (m, 2H), 7.16 (dd, 1H, J=8.1/1.8 Hz), 7.17 to 7.23 (m, 1H), 7.29 (d, 1H, J=8.1 Hz), 7.55 (d, 1H, J=8.0 Hz), 7.68 (dd, 1H, J=8.0/1.9 Hz), 7.74 (d, 1H, J=1.8 Hz), 7.78 (d, 2H, J=8.4 Hz), 8.21 (d, 2H, J=8.4 Hz).

Example 19

3-Hydroxy-2'-(5,5,8,8-tetramethyl-5,6,7,8-tetrahydro-2-naphthyl)-[1,1';4',1"]terphenyl-4"-carboxylic acid

(a) Ethyl 3-hydroxy-2'-(5,5,8,8-tetramethyl-5,6,7,8-tetrahydro-2-naphthyl)-[1,1';4',1"]terphenyl-4-carboxylate In a manner similar to that of Example 16(a), starting with 6.26 g (11.4 mmol) of the compound obtained in Example 18(c), 5.63 g (98%) of the expected product are obtained in the form of a white solid with a melting point of less than 70° C.

¹H NMR (CDCl₃) δ 0.95 (s, 6H), 1.27 (s, 6H), 1.42 (t, 3H, J=7.1 Hz), 1.58 to 1.65 (m, 4H), 4.41 (q, 2H, J=7.1 Hz), 4.95 (s, 1H), 6.63 to 6.76 (m, 3H), 6.94 (d, 1H, J=1.8 Hz), 7.11 (t, 1H, J=7.9 Hz), 7.15 (dd, 1H, J=8.2/1.9 Hz), 7.28 (d, 1H, J=8.1 Hz), 7.49 (d, 1H, J=7.9 Hz), 7.63 (dd, 1H, J=8.2/1.9 Hz), 7.71 to 7.73 (m, 1H), 7.73 (d, 2H, J=8.4 Hz), 8.13 (d, 2H, J=8.4 Hz).

(b) 3-Hydroxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 1.05 g (2.1 mmol) of the ethyl ester obtained in Example 19(a), 820 mg (83%) of 3-hydroxy-2'-(5,5,8,8-tetramethyl-5,6,7,8-tetrahydro-2-naphthyl)-[1,1';4',1"]terphenyl-40-carboxylic acid are collected in the form of a white powder with a melting point of 260–263° C.

¹H NMR (CDCl₃) δ 0.96 (s, 6H), 1.27 (s, 6H), 1.57 to 1.64 (m, 4H), 6.58 (d, 1H, J=7.7 Hz), 6.69 (dd, 1H, J=8.0/2.0 Hz), 6.75 (d, 1H, J=2.0 Hz), 6.98 (d, 1H, J=1.7 Hz), 7.03 (t, 1H, J=7.8 Hz), 7.16 (dd, 1H, J=7.9/1.8 Hz), 7.26 (d, 1H, J=8.1 Hz), 7.49 (d, 1H, J=7.9 Hz), 7.63 (dd, 1H, J=8.0/1.9 Hz), 7.71 (d, 1H, J=1.9 Hz), 7.73 (d, 2H, J=8.4 Hz), 8.14 (d, 2H, J=8.4 Hz).

Example 20

3-Methoxy-2'-(5,5,8,8-tetramethyl-5,6,7,8-tetrahydro-2-naphthyl)-[1,1';4',1"]terphenyl-4"-carboxylic acid (a) Ethyl 3-methoxy-2'-(5,5,8,8-tetramethyl-5,6,7,8-tetrahydro-2-naphthyl)-[1,1';4',1"]terphenyl-4"-carboxylate In a manner similar to that of Example 7(a), by reaction of 1.20 g (2.4 mmol) of the compound obtained in Example 19(a) with 190 μl (3.1 mmol) of methyl iodide, 1.08 g (87%) of the expected product are obtained in the form of a white solid with a melting point of 116–118° C.

¹H NMR (CDCl₃) δ 0.96 (s, 6H), 1.27 (s, 6H), 1.42 (t, 3H, J=7.1 Hz), 1.58 to 1.66 (m, 4H), 3.49 (s, 3H), 4.41 (q, 2H, J=7.1 Hz), 6.53 (d, 1H, J=1.3 Hz), 6.74 (dd, 1H, J=7.6/2.5 Hz), 6.89 (d, 1H, J=7.6 Hz), 6.95 (d, 1H, J=1.6 Hz), 7.12 to 7.30 (m, 3H), 7.56 (d, 1H, J=8.0 Hz), 7.67 (dd, 1H, J=8.0/1.8 Hz), 7.72 to 7.74 (m, 1H), 7.74 (d, 2H, J=8.3 Hz), 8.13 (d, 2H, J=8.3 Hz).

(b) 3-Methoxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 1.07 g (2.1 mmol) of the ethyl ester obtained in Example 20(a), 930 mg (92%) of 3-methoxy-2'-(5,5,8,8-tetramethyl-5,6,7,8-tetrahydro-2-naphthyl)-[1,1';4',1"]terphenyl-4"-carboxylic acid are collected in the form of a white powder with a melting point of 258–259° C.

¹H NMR (CDCl₃) δ 0.96 (s, 6H), 1.27 (s, 6H), 1.58 to 1.65 (m, 4H), 3.49 (s, 3H), 6.54 (d, 1H, J=1.6 Hz), 6.72 (dd, 1H, J=7.6/2.1 Hz), 6.89 (d, 1H, J=7.6 Hz), 6.94 (d, 1H, J=1.7 Hz), 7.14 (d, 1H, J=7.8 Hz), 7.21 (d, 1H, J=7.9 Hz), 7.28 (d, 1H, J=8.1 Hz), 7.56 (d, 1H, J=8.0 Hz), 7.68 (dd, 1H, J=8.0/1.9 Hz), 7.68 to 7.70 (m, 1H), 7.74 (d, 2H, J=8.3 Hz), 8.14 (d, 2H, J=8.3 Hz).

Example 21

2-Methoxymethoxy-2'-(5,5,8,8-tetramethyl-5,6,7,8-tetrahydro-2-naphthyl)-[1,1';4',1"]terphenyl-4"-carboxylic acid (a) 2-Methoxymethoxybromobenzene In a manner similar to that of Example 7(a), by reaction of 15.00 g (86.7 mmol) of 2-bromophenol with 8.40 g (104.0 mmol) of chloromethyl methyl ether, 18.80 g (100%) of the expected product are obtained in the form of a beige-coloured oil.

¹H NMR (CDCl₃) δ 3.53 (s, 3H), 5.25 (s, 2H), 6.89 (dt, 1H, J=7.5/1.6 Hz), 7.15 (dd, 1H, J=8.3/1.6 Hz), 7.25 (dt, 1H, J=7.3/1.6 Hz), 7.54 (dd, 1H, J=7.9/1.6 Hz).

(b) 2-Methoxymethoxyphenylboronic acid

In a manner similar to that of Example 1(a), starting with 19.00 g (8.7 mmol) of 2-methoxymethoxybromobenzene, 11.00 g (70%) of the expected product are obtained in the form of a white solid with a melting point of 63–66° C.

¹H NMR (CDCl₃) δ 3.51 (s, 3H), 5.31 (s, 2H), 6.21 (s, 2H), 7.07 (d, 1H, J=7.3 Hz), 7.14 (d, 1H, J=8.8 Hz), 7.43 (dt, 1H, J=8.6/1.9 Hz), 7.87 (dd, 1H, J=7.3/1.8 Hz).

(c) Ethyl 2-methoxymethoxy-2'-(5,5,8,8-tetramethyl-5,6,7,8-tetrahydro-2-naphthyl)-[1,1';4',1"]terphenyl-4"-carboxylate In a manner similar to that of Example 13(b), by reaction of 2.73 g (15.0 mmol) of the compound obtained in Example 21(b) with 7.00 g (12.5 mmol) of the analogue (ethyl ester) of the compound obtained in Example 13(a), 1.50 g (22%) of the expected product are obtained in the form of a white solid with a melting point of 132–135° C.

¹H NMR (CDCl₃) δ 0.91 (br s, 6H), 1.24 (s, 6H), 1.42 (t, 3H, J=7.1 Hz), 1.54 to 1.63 (m, 4H), 3.10 (s, 3H), 4.41 (q, 2H, J=7.1 Hz), 4.40 to 4.80 (br s, 2H), 6.96 (d, 1H, J=1.8 Hz), 7.02 to 7.29 (m, 7H), 7.47 (d, 1H, J=8.7 Hz), 7.65 (dd, 1H, J=7.9/1.9 Hz), 7.74 (s, 1H), 7.76 (d, 2H, J=8.4 Hz), 8.13 (d, 2H, J=8.4 Hz).

(d) 2-Methoxymethoxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 470 mg (0.86 mmol) of the ethyl ester obtained in Example 21(c), 360 mg (81%) of 2-methoxymethoxy-2'-(5,5,8,8-tetramethyl-5,6,7,8-tetrahydro-2-naphthyl)-[1,1';4',1"]terphenyl-4"-carboxylic acid are collected in the form of a white powder with a melting point of 218–221° C.

¹H NMR (CDCl₃) δ 0.91 (br s, 6H), 1.24 (s, 6H), 1.52 to 1.64 (m, 4H), 3.10 (s, 3H), 4.40 to 4.80 (br s, 2H), 6.97 (d, 1H, J=1.8 Hz), 7.02 to 7.28 (m, 6H), 7.47 (d, 1H, J=7.9 Hz), 7.67 (dd, 1H, J=7.9/1.9 Hz), 7.75 (d, 1H, J=1.8 Hz), 7.80 (d, 2H, J=8.4 Hz), 8.21 (d, 2H, J=8.3 Hz).

Example 22

2-hydroxy-2'-(5,5,8,8-tetramethyl-5,6,7,8-tetrahydro-2-naphthyl)-[1,1';4',1"]terphenyl-4"-carboxylic acid (a) Ethyl 2-hydroxy-2'-(5,5,8,8-tetramethyl-5,6,7,8-tetrahydro-2-naphthyl)-[1,1';4',1"]terphenyl-4"-carboxylate In a manner similar to that of Example 16(a), starting with 1.10 g (2.0 mmol) of the compound obtained in Example 21(c), 1.00 g (99%) of the expected product are obtained in the form of a white solid with a melting point of 161–163° C.

$^1$H NMR (CDCl$_3$) δ 0.93 (s, 6H), 1.25 (s, 6H), 1.43 (t, 3H, J=7.2 Hz), 1.55 to 1.65 (m, 4H), 4.41 (q, 2H, J=7.1 Hz), 6.81 (d, 1H, J=8.1 Hz), 6.90 (t; 1H, J=7.5 Hz), 6.99 (d, 1H, J=1.9 Hz), 7.10 to 7.20 (m, 3H), 7.28 (d, 1H, J=8.7 Hz), 7.50 (d, 1H, J=7.9 Hz), 7.69 (dd, 1H, J=7.9/1.9 Hz), 7.75 (d, 2H, J=8.5 Hz), 7.78 (d, 1H, J=1.9 Hz), 8.15 (d, 2H, J=8.4 Hz).

(b) 2-Hydroxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 390 mg (0.77 mmol) of the ethyl ester obtained in Example 22(a), 315 mg (86%) of 2-hydroxy-2'-(5,5,8,8-tetramethyl-5,6,7,8-tetrahydro-2-naphthyl)-[1,1';4',1"]terphenyl-4"-carboxylic acid are collected in the form of a white powder with a melting point of 265–269° C.

$^1$H NMR (CDCl$_3$+2 drops of DMSO-d$_6$) δ 0.93 (s, 6H), 1.25 (s, 6H), 1.55 to 1.62 (m, 4H), 6.77 to 6.85 (m, 2H), 7.02 to 7.13 (m, 3H), 7.18 to 7.27 (m, 2H), 7.51 (d, 1H, J=7.9 Hz), 7.66 (dd, 1H, J=7.9/1.9 Hz), 7.73 (d, 1H, J=7.9 Hz), 7.74 (d, 2H, J=8.3 Hz), 8.14 (d, 2H, J=8.3 Hz).

Example 23

2-Methoxy-2'-(5,5,8,8-tetramethyl-5,6,7,8-tetrahydro-2-naphthyl)-[1,1';4',1"]terphenyl-4"-carboxylic acid (a) Ethyl 2-methoxy-2'-(5,5,8,8-tetramethyl-5,6,7,8-tetrahydro-2-naphthyl)-[1,1';4',1"]terphenyl-4"-carboxylate In a manner similar to that of Example 7(a), by reaction of 580 mg (1.2 mmol) of the compound obtained in Example 22(a) with 110 μl (1.5 mmol) of methyl iodide, 530 mg (89%) of the expected product are obtained in the form of a white solid with a melting point of 133–136° C.

$^1$H NMR (CDCl$_3$) δ 0.93 (br s, 6H), 1.24 (s, 6H), 1.42 (t, 3H J=7.1 Hz), 1.56 to 1.63 (m, 4H), 3.27 (s, 3H), 4.40 (q, 2H, J=7.1 Hz), 6.71 (d, 1H, J=8.0 Hz), 6.94 (d, 1H, J=1.8 Hz), 6.98 (d, 1H, J=7.3 Hz), 7.12 (dd, 1H, J=8.1/1.9 Hz), 7.19 to 7.26 (m, 3H), 7.47 (d, 1H, J=7.9 Hz), 7.64 (dd, 1H, J=7.9/1.9 Hz), 7.71 (d, 1H, J=1.9 Hz), 7.75 (d, 2H, J=8.6 Hz), 8.12 (d, 2H, J=8.4 Hz).

(b) 2-Methoxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 530 mg (1.0 mmol) of the ethyl ester obtained in Example 23(a), 435 mg (87%) of 2-methoxy-2'-(5,5,8,8-tetramethyl-5,6,7,8-tetrahydro-2-naphthyl)-[1,1';4',1"]terphenyl-4"-carboxylic acid are collected in the form of a white powder with a melting point of 239–243° C.

$^1$H NMR (CDCl$_3$) δ 0.93 (s, 6H), 1.25 (s, 6H), 1.54 to 1.63 (m, 4H), 3.28 (s, 3H), 6.71 (d, 1H, J=8.1 Hz), 6.95 to 7.01 (m, 2H), 7.14 (d, 1H, J=8.1 Hz), 7.20 to 7.25 (m, 3H), 7.49 (d, 1H, J=7.9 Hz), 7.67 (d, 1H, J=7.9 Hz), 7.74 (d, 1H, J=1.8 Hz), 7.79 (d, 2H, J=8.2 Hz), 8.21 (d, 2H, J=8.2 Hz).

Example 24

2'-Methoxymethoxy-5'-(5,5,8,8-tetramethyl-5,6,7,8-tetrahydro-2-naphthyl)biphenyl-4-carboxylic acid (a) 4-(5,5,8,8-Tetramethyl-5,6,7,8-tetrahydro-2-naphthyl)phenol.

In a manner similar to that of Example 1(d), by reaction of 53.00 g (230.3 mmol) of the boronic acid obtained in Example 1(a) with 23.10 g (133.6 mmol) of 4-bromophenol, 60.00 g (70%) of the expected compound are obtained in the form of a white solid with a melting point of 137–140° C.

$^1$H NMR (CDCl$_3$) δ 1.31 (s, 6H), 1.33 (s, 6H), 1.71 (s, 4H), 4.77 (s, 1H), 6.89 (d, 2H, J=8.6 Hz), 7.30 (dd, 1H, J=8.2/1.9 Hz), 7.36 (d, 1H, J=8.1 Hz), 7.45 (d, 1H, J=1.9 Hz), 7.46 (d, 2H, J=8.6 Hz).

(b) 2-Bromo-4-(5,5,8,8-tetramethyl-5,6,7,8-tetrahydro-2-naphthyl)-phenol 39.00 g (139.0 mmol) of the compound obtained in Example 24(a) and 350 ml of dichloromethane are introduced into a round-bottomed flask. 23.40 g (146.0 mmol) of bromine dissolved in 50 ml of dichloromethane are added dropwise and the mixture is stirred for thirty minutes at room temperature. The reaction medium is evaporated to dryness, the residue is taken up in water and ethyl acetate and the organic phase is separated out after settling has taken place, washed with aqueous sodium metabisulphite solution, dried over magnesium sulphate, filtered and evaporated. 40.60 g (80%) of the expected product are collected in the form of a yellow oil.

$^1$H NMR (CDCl$_3$) δ 1.31 (s, 6H), 1.34 (s, 6H), 1.71 (s, 4H), 5.49 (s, 1H), 7.07 (d, 1H, J=8.4 Hz), 7.27 (dd, 1H, J=7.7/2.0 Hz), 7.36 (d, 1H, J=8.2 Hz), 7.43 (dd, 1H, J=7.8/2.0 Hz), 7.51 (d, 1H, J=2.1 Hz), 7.65 (d, 1H, J=2.1 Hz)

(c) 6-(3-Bromo-4-methoxymethoxyphenyl)-1,1,4,4-tetramethyl-1,2,3,4-tetrahydronaphthalene In a manner similar to that of Example 7(a), by reaction of 40.60 g (113.1 mmol) of the compound obtained in Example 24(b) with 10.65 ml (135.0 mmol) of chloromethyl methyl ether, 45.00 g (98%) of the expected product are obtained in the form of a brown oil.

$^1$H NMR (CDCl$_3$) δ 1.31 (s, 6H), 1.33 (s, 6H), 1.71 (s, 4H), 3.55 (s, 3H), 5.28 (s, 2H), 7.20 (d, 1H, J=8.5 Hz), 7.27 (dd, 1H, J=8.2/1.9 Hz), 7.36 (d, 1H, J=8.2 Hz), 7.43 (dd, 1H, J=7.8/2.0 Hz), 7.51 (d, 1H, J=2.1 Hz), 7.75 (d, 1H, J=2.2 Hz).

(d) 2-Methoxymethoxy-5-(5,5,8,8-tetramethyl-5,6,7,8-tetrahydro-2-naphthyl)phenylboronic acid In a manner similar to that of Example 1(a), starting with 45.00 g (112.0 mmol) of the compound obtained in Example 24(c), 41.50 g (100%) of the expected product are obtained in the form of a brown oil which is used directly for the following step.

(e) Ethyl 2'-methoxymethoxy-5'-(5,5,8,8-tetramethyl-5,6,7,8-tetrahydro-2-naphthyl)biphenyl-4-carboxylate In a manner similar to that of Example 1(d), by reaction of 41.20 g (112.0 mmol) of the compound obtained in Example 24(d) with 30.90 g (112.0 mmol) of ethyl 4-iodobenzoate, 18.00 g (34%) of the expected product are obtained in the form of a yellow oil.

$^1$H NMR (CDCl$_3$) δ 1.31 (s, 6H), 1.33 (s, 6H), 1.41 (t, 3H, J=7.1 Hz), 1.72 (s, 4H), 3.40 (s, 3H), 4.40 (q, 2H, J=7.1 Hz), 5.15 (s, 2H), 7.23 to 7.39 (m, 3H), 7.44 to 7.59 (m, 3H), 7.65 (d, 2H, J=8.1 Hz), 8.12 (d, 2H, J=8.2 Hz).

(f) 2'-Methoxymethoxy-5'-(5,5,8,8-tetramethyl-5,6,7,8-tetrahydro-2-naphthyl)biphenyl-4-carboxylic acid In a manner similar to that of Example 1(e), starting with 1.00 g (2.1 mmol) of the ester obtained in Example 24(e), 660 mg (70%) of 2'-methoxymethoxy-5'-(5,5,8,8-tetramethyl-5,6,7,8-tetrahydro-2-naphthyl)biphenyl-4-carboxylic acid are obtained in the form of beige-coloured crystals with a melting point of 183–185° C.

$^1$H NMR (CDCl$_3$) δ 1.32 (s, 6H), 1.34 (s, 6H), 1.72 (s, 4H), 3.42 (s, 3H), 5.18 (s, 2H), 7.28 to 7.40 (m, 3H), 7.49 to 7.56 (m, 3H), 7.70 (d, 2H, J=8.2 Hz), 8.19 (d, 2H, J=8.2 Hz).

Example 25

2'-Methoxy-5'-(5,5,8,8-tetramethyl-5,6,7,8-tetrahydro-2-naphthyl)biphenyl-4-carboxylic acid

(a) Ethyl 2'-hydroxy-5'-(5,5,8,8-tetramethyl-5,6,7,8-tetrahydro-2-naphthyl) biphenyl-4-carboxylate In a manner similar to that of Example 16(a), starting with 17.00 g (36.0 mmol) of the compound obtained in Example 24(e), 15.10 g (98%) of the expected product are obtained in the form of a beige-coloured solid with a melting point of 148–152° C.

$^1$H NMR (CDCl$_3$) δ 1.31 (s, 6H), 1.33 (s, 6H), 1.42 (t, 3H, J=7.1 Hz), 1.72 (s, 4H), 4.41 (q, 2H, J=7.2 Hz), 5.29 (br s, 1H), 7.04 (d, 1H, J=8.1 Hz), 7.31 to 7.39 (m, 2H), 7.46 to 7.52 (m, 3H), 7.63 (d, 2H, J=8.3 Hz), 8.17 (d, 2H, J=8.3 Hz).

(b) Ethyl 2'-methoxy-5'-(5,5,8,8-tetramethyl-5,6,7,8-tetramethyl-5,6,7,8-tetrahydro-2-naphthyl)biphenyl-4-carboxylate In a manner similar to that of Example 7(a), by reaction of 1.53 g (3.6 mmol) of the compound obtained in Example 25(a) with 330 μl (5.4 mmol) of methyl iodide, 1.40 g (88%) of the expected product are obtained in the form of a brown oil.

$^1$H NMR (CDCl$_3$) δ 1.31 (s, 6H), 1.33 (s, 6H), 1.42 (t, 3H, J=7.1 Hz), 3.86 (s, 3H), 1.72 (s, 4H), 4.41 (q, 2H, J=7.2 Hz), 7.04 (d, 1H, J=8.1 Hz), 7.31 to 7.39 (m, 2H), 7.46 to 7.52 (m, 3H), 7.63 (d, 2H, J=8.3 Hz), 8.17 (d, 2H, J=8.3 Hz).

(c) 2'-Methoxy-5'-(5,5,8,8-tetramethyl-5,6,7,8-tetrahydro-2-naphthyl)biphenyl-4-carboxylic acid In a manner similar to that of Example 1(e), starting with 1.40 g (3.6 mmol) of the ester obtained in Example 25(b), 1.07 g (72%) of 2'-methoxy-5'-(5,5,8,8-tetramethyl-5,6,7,8-tetrahydro-2-naphthyl)-biphenyl-4-carboxylic acid are obtained in the form of a white crystalline solid with a melting point of 233–235° C.

$^1$H NMR (CDCl$_3$) δ 1.32 (s, 6H), 1.34 (s, 6H), 1.72 (s, 4H), 3.86 (s, 3H), 7.07 (d, 1H, J=8.4 Hz), 7.32 to 7.39 (m, 2H), 7.49 to 7.58 (m, 3H), 7.65 (d, 2H, J=8.3 Hz), 8.11 (dd, 1H, J=8.3 Hz).

Example 26

2'-Propyloxy-5'-(5,5,8,8-tetramethyl-5,6,7,8-tetrahydro-2-naphthyl)biphenyl-4-carboxylic acid

(a) Ethyl 2'-propyloxy-5'-(5,5,8,8-tetramethyl-5,6,7,8-tetrahydro-2-naphthyl)biphenyl-4-carboxylate In a manner similar to that of Example 7(a), by reaction of 1.34 g (3.1 mmol) of the compound obtained in Example 25(a) with 460 μl (4.7 mmol) of propyl iodide, 1.30 g (88%) of the expected product are obtained in the form of a colourless oil.

$^1$H NMR (CDCl$_3$) δ 0.98 (t, 3H, J=7.3 Hz), 1.32 (s, 6H), 1.33 (s, 6H), 1.42 (t, 3H, J=7.1 Hz), 1.72 to 1.77 (m, 2H), 1.72 (s, 4H), 3.98 (t, 2H, J=6.4 Hz), 4.41 (q, 2H, J=7.1 Hz), 7.04 (d, 1H, J=9.1 Hz), 7.31 to 7.39 (m, 2H), 7.49 to 7.54 (m, 3H), 7.67 (d, 2H, J=8.4 Hz), 8.09 (d, 2H, J=8.4 Hz).

(b) 2'-Propyloxy-5'-(5,5,8,8-tetramethyl-5,6,7,8-tetrahydro-2-naphthyl)biphenyl-4-carboxylic acid In a manner similar to that of Example 1(e), starting with 1.30 g (3.1 mmol) of the ester obtained in Example 26(a), 850 mg (61%) of 2'-propyloxy-5'-(5,5,8,8-tetramethyl-5,6,7,8-tetrahydro-2-naphthyl)-biphenyl-4-carboxylic acid are obtained in the form of a white crystalline solid with a melting point of 199–204° C.

$^1$H NMR (CDCl$_3$) δ 0.98 (t, 3H, J=7.3 Hz), 1.71 to 1.81 (m, 2H), 1.72 (s, 4H), 3.99 (t, 2H, J=6.4 Hz), 7.05 (d, 1H, J=9.2 Hz), 7.35 to 7.40 (m, 2H), 7.49 to 7.56 (m, 3H), 7.72 (d, 2H, J=8.4 Hz), 8.17 (d, 2H, J=8.4 Hz).

Example 27

2'-Hydroxy-5'-(5,5,8,8-tetramethyl-5,6,7,8-tetrahydro-2-naphthyl)biphenyl-4-carboxylic acid In a manner similar to that of Example 1(e), starting with 1.00 g (2.3 mmol) of the ester obtained in Example 25(a), 800 mg (86%) of 2'-hydroxy-5'-(5,5,8,8-tetramethyl-5,6,7,8-tetrahydro-2-naphthyl)-biphenyl-4-carboxylic acid are obtained in the form of a white crystalline solid with a melting point of 264–267° C.

$^1$H NMR (CDCl$_3$) δ 1.31 (s, 6H), 1.33 (s, 6H), 1.71 (s, 4H), 7.07 (d, 1H, J=8.3 Hz), 7.34 to 7.37 (m, 2H), 7.41 (dd, 1H, J=8.4/2.3 Hz), 7.47 to 7.49 (m, 2H), 7.72 (d, 2H, J=8.3 Hz), 8.11 (d, 2H, J=8.4 Hz).

Example 28

4'-(5,5,8,8-Tetramethyl-5,6,7,8-tetrahydro-2-naphthyl)-[1,1';2',1"]terphenyl-4"-carboxylic acid (a) Ethyl 5'-(5,5,8,8-tetramethyl-5,6,7,8-tetrahydro-2-naphthyl)-2'-trifluoromethanesulphonyloxy-biphenyl-4-carboxylate 2.00 g (4.7 mmol) of the ethyl ester obtained in Example 25(a), 1.30 g (4.9 mmol) of 4-nitrophenyl triflate, 1.30 g (9.3 mmol) of potassium carbonate and 30 ml of N,N-dimethylformamide are introduced into a three-necked flask under a stream of nitrogen. The reaction medium is stirred at room temperature for sixteen hours, poured into a water/ethyl ether mixture, washed with water, dried over magnesium sulphate and evaporated. 2.60 g (100%) of the expected product are collected in the form of yellow crystals with a melting point of 110–113° C.

$^1$H NMR (CDCl$_3$) δ 1.32 (s, 6H), 1.34 (s, 6H), 1.43 (t, 3H, J=7.1 Hz), 1.73 (s, 4H), 4.42 (t, 2H, J=7.2 Hz), 7.34 (dd, 1H, J=8.2/1.9 Hz), 7.39 to 7.50 (m, 3H), 7.59 (d, 2H, J=8.4 Hz), 7.60 to 7.65 (m, 2H), 8.17 (d, 2H, J=8.4 Hz).

(b) Ethyl 4'-(5,5,8,8-tetramethyl-5,6,7,8-tetrahydro-2-naphthyl)-[1,1';2',1"]terphenyl-4"-carboxylate In a manner similar to that of Example 13(b), by reaction of 2.60 g (4.6 mmol) of the compound obtained in Example 28(a) with 626 mg (5.1 mmol) of phenylboronic acid, 1.10 g (47%) of the expected product are obtained in the form of yellow crystals with a melting point of 233–235° C.

$^1$H NMR (CDCl$_3$) δ 1.21 (t, 3H, J=7.1 Hz), 1.32 (s, 6H), 1.35 (s, 6H), 1.68 (s, 4H), 4.29 (q, 2H, J=7.0 Hz), 7.25 to 7.32 (m, 5H), 7.44 (d, 2H, J=8.2 Hz), 7.54 to 7.70 (m, 3H), 7.89 to 7.91 (m, 3H), 8.06 (d, 2H, J=8.2 Hz).

(c) 4'-(5,5,8,8-Tetramethyl-5,6,7,8-tetrahydro-2-naphthyl)-[1,1';2',1"]terphenyl-4"-carboxylic acid In a manner similar to that of Example 1(e), starting with 1.00 g (2.0 mmol) of the ester obtained in Example 28(b), 700 mg (77%) of 4'-(5,5,8,8-tetramethyl-5,6,7,8-tetrahydro-2-naphthyl)-[1,1';2',1"]terphenyl-4"-carboxylic acid are obtained in the form of beige-coloured crystals with a melting point of 258–262° C.

$^1$H NMR (DMSO-d$_6$) δ 1.28 (s, 6H), 1.32 (s, 6H), 1.68 (s, 4H), 7.11 to 7.15 (m, 2H), 7.25 to 7.28 (m, 3H), 7.32 (d, 2H, J=8.2 Hz), 7.43 (d, 1H, J=8.2 Hz), 7.46 (d, 1H, J=1.8 Hz), 7.51 (d, 1H, J=8.0 Hz), 7.62 to 7.64 (m, 2H), 7.74 (dd, 1H, J=8.0/1.8 Hz), 7.81 (d, 2H, J=8.3 Hz).

Example 29

2'-Methoxymethoxy-3'-(5,5,8,8-tetramethyl-5,6,7,8-tetrahydro-2-naphthyl)biphenyl-4-carboxylic acid (a) 1,3-Dibromo-2-methoxymethoxybenzene In a manner similar to that of Example 7(a), by reaction of 19.16 g (76.1 mmol) of 2,6-dibromophenol with 7.35 g (91.3 mmol) of chloromethyl methyl ether, 22.50 g (100%) of the expected product are obtained in the form of a colourless oil.

$^1$H NMR (CDCl$_3$) δ 3.73 (s, 3H), 5.18 (s, 2H), 6.88 (t, 1H, J=8.1 Hz), 7.52 (d, 2H, J=8.0 Hz).

(b) 6-(3-Bromo-2-methoxymethoxyphenyl)-1,1,4,4-tetramethyl-1,2,3,4-tetrahydronaphthalene In a manner similar to that of Example 1(d), by reaction of 21.72 g (73.4 mmol) of the compound obtained in Example 29(a) with 18.74 g (80.7 mmol) of the boronic acid obtained in Example 1(a), 4.04 g (14%) of the expected product are obtained in the form of a white solid with a melting point of 74° C.

$^1$H NMR (CDCl$_3$) δ 1.30 (s, 12H), 1.71 (s, 4H), 3.11 (s, 3H), 4.73 (s, 2H), 7.04 (t, 1H, J=7.8 Hz), 7.23 (dd, 1H, J=8.1/1.8 Hz), 7.28 (dd, 1H, J=7.9/1.6 Hz), 7.34 (d, 1H, J=8.1 Hz), 7.45 (d, 1H, J=1.8 Hz), 7.53 (dd, 1H, J=7.9/1.6 Hz).

(c) 2-Methoxymethoxy-3-(5,5,8,8-tetramethyl-5,6,7,8-tetrahydro-2-naphthyl)phenylboronic acid In a manner similar to that of Example 1(a), starting with 4.04 g (10.0 mmol) of the compound obtained in Example 29(b), 3.82 g (100%) of the expected product are obtained in the form of a colourless oil.

$^1$H NMR (CDCl$_3$) δ 1.30 (s, 6H), 1.32 (s, 6H), 1.72 (s, 4H), 3.26 (s, 3H), 4.58 (s, 2H), 6.13 (s, 2H), 7.21 to 7.27 (m, 3H), 7.31 to 7.40 (m, 1H), 7.44 to 7.52 (m, 1H), 7.80 (dd, 1H, J=7.3/1.8 Hz).

(d) Ethyl 2'-methoxymethoxy-3'-(5,5,8,8-tetramethyl-5,6,7,8-tetrahydro-2-naphthyl)biphenyl-4-carboxylate In a manner similar to that of Example 1(d), by reaction of 3.82 g (10.4 mmol) of the compound obtained in Example 29(c) with 2.20 g (8.0 mmol) of ethyl 4-iodobenzoate, 3.28 g (87%) of the expected product are obtained in the form of a white crystalline solid with a melting point of 75° C.

$^1$H NMR (CDCl$_3$) δ 1.32 (s, 6H), 1.33 (s, 6H), 1.42 (t, 3H, J=7.1 Hz), 1.72 (s, 4H), 2.60 (s, 3H), 4.33 (s, 2H), 4.41 (q, 2H, J=7.2 Hz), 7.29 to 7.53 (m, 6H), 7.70 (d, 2H, J=8.4 Hz), 8.11 (d, 2H, J=8.4 Hz).

(e) 2'-Methoxymethoxy-3'-(5,5,8,8-tetramethyl-5,6,7,8-tetrahydro-2-naphthyl)biphenyl-4-carboxylic acid In a manner similar to that of Example 1(e), starting with 1.00 g (2.1 mmol) of the ester obtained in Example 29(d), 500 mg (53%) of 2'-methoxymethoxy-3'-(5,5,8,8-tetramethyl-5,6,7,8-tetrahydro-2-naphthyl)biphenyl-4-carboxylic acid are obtained in the form of a white crystalline solid with a melting point of 176° C.

$^1$H NMR (CDCl$_3$) δ 1.31 (s, 6H), 1.33 (s, 6H), 1.72 (s, 4H), 2.61 (s, 3H), 4.35 (s, 2H), 7.24 to 7.35 (m, 4H), 7.41 (dd, 1H, J=7.3/2.3 Hz), 7.54 (s, 1H), 7.75 (d, 2H, J=8.4 Hz), 8.19 (d, 2H, J=8.4 Hz).

Example 30

2'-Hydroxy-3'-(5,5,8, 8-tetramethyl-5,6,7,8-tetrahydro-2-naphthyl)biphenyl)-4-carboxylic acid (a) Ethyl 2'-hydroxy-3'-(5,5,8,8-tetramethyl-5,6,7,8-tetrahydro-2-naphthyl)biphenyl-4-carboxylate In a manner similar to that of Example 16(a), starting with 2.28 g (4.82 mmol) of the compound obtained in Example 29(d), 1.59 g (77%) of the expected product are obtained in the form of a white solid with a melting point of 121° C.

$^1$H NMR (CDCl$_3$) δ 1.31 (s, 6H), 1.33 (s, 6H), 1.41 (t, 3H, J=7.1 Hz), 1.73 (s, 4H), 4.40 (q, 2H, J=7.1 Hz), 5.53 (s, 1H), 7.07 (t, 1H, J=7.6 Hz), 7.74 to 7.32 (m, 3H), 7.42 to 7.45 (m, 2H), 7.69 (d, 2H, J=8.4 Hz), 8.12 (d, 2H, J=8.4 Hz).

(b) 2'-Hydroxy-3'-(5,5,8,8-tetramethyl-5,6,7,8-tetrahydro-2-naphthyl)biphenyl-4-carboxylic acid In a manner similar to that of Example 1(e), starting with 700 mg (1.6 mmol) of the ester obtained in Example 30(a), 526 mg (81%) of 2'-hydroxy-3'-(5,5,8,8-tetramethyl-5,6,7,8-tetrahydro-2-naphthyl)biphenyl-4-carboxylic acid are obtained in the form of a white crystalline solid with a melting point of 232° C.

$^1$H NMR (CDCl$_3$) δ 1.31 (s, 6H), 1.33 (s, 6H), 1.73 (s, 4H), 5.58 (br s, 1H), 7.08 (t, 1H, J=7.6 Hz), 7.24 to 7.35 (m, 3H), 7.43 to 7.46 (m, 2H), 7.74 (d, 2H, J=8.4 Hz), 8.20 (d, 2H, J=8.3 Hz).

Example 31

2'-Methoxy-3'-(5,5,8,8-tetramethyl-5,6,7,8-tetrahydro-2-naphthyl)biphenyl-4-carboxylic acid

(a) Ethyl 2'-methoxy-3'-(5,5,8,8-tetramethyl-5,6,7,8-tetrahydro-2-naphthyl)biphenyl-4-carboxylate In a manner similar to that of Example 7(a), by reaction of 890 mg (2.1 mmol) of the compound obtained in Example 30(a) with 190 μl (3.1 mmol) of methyl iodide, 800 mg (87%) of the expected product are obtained in the form of a colourless oil.

$^1$H NMR (CDCl$_3$) δ 1.32 (s, 12H), 1.42 (t, 3H, J=7.1 Hz), 1.72 (s, 4H), 3.20 (s, 3H), 4.41 (q, 2H, J=7.1 Hz), 7.23 to 7.35 (m, 4H), 7.39 (dd, 1H, J=7.3/2.1 Hz), 7.56 (d, 1H, J=1.4 Hz), 7.69 (d, 2H, J=8.3 Hz), 8.11 (d, 2H, J=8.3 Hz).

(b) 2'-Methoxy-3'-(5,5,8,8-tetramethyl-5,6,7,8-tetrahydro-2-naphthyl)biphenyl-4-carboxylic acid In a manner similar to that of Example 1(e), starting with 800 mg (1.8 mmol) of the ester obtained in Example 31(a), 502 mg (67%) of 2'-methoxy-3'-(5,5,8,8-tetramethyl-5,6,7,8-tetrahydro-2-naphthyl)biphenyl-4-carboxylic acid are obtained in the form of a white crystalline solid with a melting point of 205° C., $^1$H NMR (CDCl$_3$) δ 1.33 (s, 12H), 1.73 (s, 4H), 7.25 to 7.36 (m, 4H), 7.41 (dd, 1H, J=7.4/2.0 Hz), 7.57 (d, 1H, J=1.2 Hz), 7.74 (d, 2H, J=8.4 Hz), 8.20 (d, 2H, J=8.4 Hz).

Example 32

3'-Methoxymethoxymethyl-5'-(5,5,8,8-tetramethyl-5,6,7,8-tetrahydro-2-naphthyl)biphenyl-4-carboxylic acid

(a) Methyl 3-bromo-5-(5,5,8,8-tetramethyl-5,6,7,8-tetrahydro-2-naphthyl)benzoate.

In a manner similar to that of Example 1(d), by reaction of 7.35 g (21.6 mmol) of methyl 3-bromo-5-iodobenzoate with 7.44 g (32.4 mmol) of the boronic acid obtained in Example 1(a), 5.12 g (59%) of the expected product are obtained in the form of a white powder with a melting point of 88° C.

$^1$H NMR (CDCl$_3$) δ 1.32 (s, 6H), 1.35 (s, 6H), 1.72 (s, 4H), 3.95 (s, 3H), 7.34 (dd, 1H, J=8.2/1.9 Hz), 7.40 (d, 1H, J=8.2 Hz), 7.48 (d, 1H, J=1.7 Hz), 7.87 (t, 1H, J=1.8 Hz), 8.11 (t, 1H, J=1.6 Hz), 8.16 (t, 1H, J=1.5 Hz).

(b) 3-Bromo-5-(5,5,8,8-tetramethyl-5,6,7,8-tetrahydro-2-naphthyl)benzoic acid In a manner similar to that of Example 1(e), starting with 4.92 g (12.3 mmol) of the ester obtained in Example 32(a), 3.26 g (70%) of the expected product are obtained in the form of a white powder with a melting point of 165° C.

$^1$H NMR (CDCl$_3$) δ 1.33 (s, 6H), 1.36 (s, 6H), 1.73 (s, 4H), 7.35, (dd, 1H, J=8.2/1.8 Hz), 7.39 (d, 1H, J=8.2 Hz), 7.50 (d, 1H, J=1.7 Hz), 7.94 (t, 1H, J=1.7 Hz), 8.20 (t, 1H, J=1.6 Hz), 8.24 (t, 1H, J=1.5 Hz).

(c) 3-Bromo-5-(5,5,8,8-tetramethyl-5,6,7,8-tetrahydro-2-naphthyl)benzyl alcohol 2.76 g (0.87 mmol) of the compound obtained in Example 32(b) and 60 ml of THF are introduced into a round-bottomed flask. The solution obtained is cooled to 0° C. and 13.75 ml (13.7 mmol) of a solution of borane (1 M) in THF are added dropwise and the mixture is stirred for sixteen hours at room temperature and then for two hours at 50° C. Methanol is added slowly, the mixture is taken up in water and ethyl ether and the organic phase is separated out after settling has taken place, extracted with ethyl ether, dried over magnesium sulphate, filtered and evaporated. 2.92 g (100%) of the expected product are collected in the form of a colourless oil.

$^1$H NMR (CDCl$_3$) δ 1.30 (s, 6H), 1.33 (s, 6H), 1.71 (s, 4H), 2.60 (br s, 1H), 4.68 (s, 2H), 7.28 (dd, 1H, J=8.2/1.9 Hz), 7.36 (d, 1H, J=8.2 Hz), 7.45 to 7.47 (m, 3H), 7.60 (s, 1H).

(d) 3-Methoxymethoxymethyl-5-(5,5,8,8-tetramethyl-5,6,7,8-tetrahydro-2-naphthyl)bromobenzene In a manner similar to that of Example 7(a), by reaction of 2.92 g (7.8 mmol) of the bromo alcohol obtained in Example 32(c) with 650 μl (8.6 mmol) of chloromethyl methyl ether, 2.52 g (77%) of the expected product are obtained in the form of a yellow oil.

$^1$H NMR (CDCl$_3$) δ 1.31 (s, 6H), 1.34 (s, 6H), 1.72 (s, 4H), 3.43 (s, 3H), 4.62 (s, 2H), 4.73 (s, 2H), 7.31 (dd, 1H, J=8.2/1.9 Hz), 7.38 (d, 1H, J=8.2 Hz), 7.43 to 7.48 (m, 3H), 7.62 (m, 1H, J=1.9 Hz).

(e) 3-Methoxymethoxymethyl-5-(5,5,8,8-tetramethyl-5,6,7,8-tetrahydro-2-naphthyl)phenylboronic acid In a manner similar to that of Example 1(a), starting with 2.52 g (6.0 mmol) of the compound obtained in Example 32(d), 2.60 g (100%) of the expected product are obtained in the form of a yellow oil which is used without further purification in the following step.

(f) Ethyl 3'-methoxymethoxymethyl-5'-(5,5,8,8-tetramethyl-5,6,7,8-tetrahydro-2-naphthyl)biphenyl-4-carboxylate In a manner similar to that of Example 1(d), by reaction of 2.60 g (6.8 mmol) of the compound obtained in Example 32(e) with 2.81 g (6.2 mmol) of ethyl 4-iodobenzoate, 1.48 g (45%) of the expected product are obtained in the form of a yellow oil.

$^1$H NMR (CDCl$_3$) δ 1.33 (s, 6H), 1.35 (s, 6H), 1.42, (t, 3H, J=7.1 Hz), 1.73 (s, 4H), 3.46 (s, 3H), 4.41 (q, 2H, J=7.1 Hz), 4.73 (s, 2H), 4.78 (s, 2H), 7.40 (d, 1H, J=0.8 Hz), 7.55 to 7.58 (m, 3H), 7.71 (d, 2H, J=8.4 Hz), 7.73 (s, 1H), 8.14 (d, 2H, J=8.4 Hz).

(g) 3'-Methoxymethoxymethyl-5'-(5,5,8,8-tetramethyl-5,6,7,8-tetrahydro-2-naphthyl)biphenyl-4-carboxylic acid In a manner similar to that of Example 1(e), starting with 600 mg (1.2 mmol) of the ester obtained in Example 32(f), 560 mg (99%) of 3'-methoxymethoxymethyl-5'-(5,5,8,8-tetramethyl-5,6,7,8-tetrahydro-2-naphthyl)biphenyl-4-carboxylic acid are obtained in the form of a white crystalline solid with a melting point of 165° C.

$^1$H NMR (CDCl$_3$) δ 1.33 (s, 6H), 1.36 (s, 6H), 1.74 (s, 4H), 3.47 (s, 3H), 4.75 (s, 2H), 4.79 (s, 2H), 7.41 (s, 2H), 7.56 to 7.60 (m, 3H), 7.74 to 7.78 (m, 3H), 8.22 (d, 2H, J=8.3 Hz).

Example 33

3'-Hydroxymethyl-5'-(5,5,8,8-tetramethyl-5,6,7,8-tetrahydro-2-naphthyl)biphenyl-4-carboxylic acid (a) Ethyl 3'-hydroxymethyl-5'-(5,5,8,8-tetramethyl-5,6,7,8-tetrahydro-2-naphthyl)biphenyl-4-carboxylate In a manner similar to that of Example 16(a), starting with 670 mg (1.4 mmol) of the compound obtained in Example 32(f), 380 mg (62%) of the expected product are obtained in the form of a yellow oil.

$^1$H NMR (CDCl$_3$+2 drops of DMSO-d$_6$) δ 1.33 (s, 6H), 1.36 (s, 6H), 1.73 (s, 4H), 4.79 (s, 2H), 7.40 to 7.43 (m, 3H), 7.56 (s, 1H), 7.61 (d, 1H, J=7.4 Hz), 7.69 (s, 1H), 7.73 (d, 2H, J=8.4 Hz), 8.13 (d, 2H, J=8.3 Hz).

(b) 3'-Hydroxymethyl-5'-(5,5,8,8-tetramethyl-5,6,7,8-tetrahydro-2-naphthyl)biphenyl-4-carboxylic acid In a manner similar to that of Example 1(e), starting with 380 mg (0.86 mmol) of the ester obtained in Example 33(a), 260 mg (73%) of 3'-hydroxymethyl-5'-(5,5,8,8-tetramethyl-5,6,7,8-tetrahydro-2-naphthyl)biphenyl-4-carboxylic acid are obtained in the form of a white crystalline solid with a melting point of 213° C.

$^1$H NMR (DMSO-d$_6$) δ 1.33 (s, 6H), 1.36 (s, 6H), 1.73 (s, 4H), 4.79 (s, 2H), 7.40 to 7.43 (m, 3H), 7.56 (s, 1H), 7.61 (d, 2H, J=7.3 Hz), 7.69 (s, 1H), 7.73 (d, 2H, J=8.4 Hz), 8.13 (d, 2H, J=8.3 Hz).

Example 34

2'-(4,4-Dimethylthiochroman-7-yl)-[1,1';4',1"]terphenyl-4"-carboxylic acid (a) Ethyl 3-methoxymethoxybiphenyl-4-carboxylate In a manner similar to that of Example 1(d), by reaction of 85.00 g (566.7 mmol) of the compound obtained in Example 18(b) with 104.30 g (377.8 mmol) of ethyl 4-iodobenzoate, 162.4 g (100%) of the expected product are obtained in the form of a brown oil.

$^1$H NMR (CDCl$_3$) δ 1.42 (t, 3H, J=7.2 Hz), 3.51 (s, 3H), 4.40 (q, 2H, J=7.1 Hz), 5.24 (s, 2H), 7.08 (dt, 1H, J=8.1/1.0 Hz), 7.25 to 7.42 (m, 3H), 7.65 (d, 2H, J=8.5 Hz), 8.10 (d, 2H, J=8.5 Hz).

(b) Ethyl 3'-hydroxybiphenyl-4-carboxylate

In a manner similar to that of Example 16(a), starting with 162.00 g (566.7 mmol) of the compound obtained in Example 34(a), 133.41 g (97%) of the expected product are obtained in the form of a beige-coloured powder with a melting point of 76° C.

$^1$H NMR (CDCl$_3$) δ 1.26 (s, 12H), 1.41 (t, 3H, J=7.1 Hz), 4.39 (q, 2H, J=7.1 Hz), 6.88 to 6.91 (m, 1H), 7.09 to 7.13 (m, 2H), 7.25 to 7.33 (m, 1H), 7.64 (m, 2H, J=8.3 Hz), 8.08 (d, 2H, J=8.3 Hz), 8.77 (br s, 1H).

(c) 3'-Hydroxybiphenyl-4-carboxylic acid

In a manner similar to that of Example 1(e), starting with 130.00 g (536.6 mmol) of the ester obtained in Example 34(b), 40.00 g (35%) of the expected product are obtained in the form of a pale beige powder with a melting point of 180° C.

$^1$H NMR (DMSO-d$_6$) δ 6.50 (dd, 1H, J=7.2/1.5 Hz), 6.71 to 6.74 (m, 2H), 7.22 to 7.31 (m, 1H), 7.30 (d, 2H, J=8.3 Hz), 7.71 (d, 2H, J=8.3 Hz).

(d) 4'-Iodo-3'-hydroxybiphenyl-4-carboxylic acid 40.00 g (186.7 mmol) of the compound obtained in Example 34(c), 7.47 g (186.7 mmol) of sodium hydroxide pellets, 27.98 g (186.7 mmol) of sodium iodide and 800 ml of methanol are introduced into a two-litre three-necked flask under a stream of nitrogen. The mixture is cooled to 0° C. and 111.00 g (186.7 mmol) of aqueous 12.5% sodium hypochlorite solution are added dropwise over one hour and fifty minutes. The reaction medium is stirred for five hours at 0° C., a sodium thiosulphate solution is then added, this mixture is acidified to pH 5 and extracted with ethyl ether, the organic phase is washed with water to neutral pH, dried over magnesium sulphate and filtered and the solvents are evaporated off. 54.00 g (85%) of the expected compound are collected in the form of a rust-coloured powder with a melting point of 174° C.

$^1$H NMR (DMSO-d$_6$) δ 6.83 to 6.89 (m, 1H), 7.11 to 7.24 (m, 1H), 7.38 to 7.41 (m, 1H), 7.60 to 7.76 (m, 2H), 8.06 to 8.17 (m, 2H).

(e) Methyl 4'-iodo-3'-hydroxybiphenyl-4-carboxylate

In a manner similar to that of Example 1(b), starting with 54.00 g (158.8 mmol) of the compound obtained in Example 34(d), 27.16 g (48%) of the expected product are obtained in the form of a pale beige powder with a melting point of 192° C.

$^1$H NMR (DMSO-d$_6$) δ 3.44 (s, 3H), 6.37 (dd, 1H, J=8.1/2.1 Hz), 6.70 (d, 1H, J=2.0 Hz), 7.13 (d, 2H, J=8.5 Hz), 7.26 (d, 1H, J=8.1 Hz), 7.58 (d, 2H, J=8.4 Hz), 9.45 (br s, 1H).

(f) Methyl 2'-hydroxy-[1,1';4',1"]terphenyl-4"-carboxylate

In a manner similar to that of Example 1(d), by reaction of 27.16 g (76.6 mmol) of the compound obtained in Example 34(e) with 14.03 g (115.0 mmol) of phenylboronic acid, 2.90 g (12%) of the expected product are obtained in the form of a yellow oil.

$^1$H NMR (DMSO-$d_6$) δ 3.88 (s, 3H), 7.25 to 7.45 (m, 6H), 7.61 (d, 2H, J=7.1 Hz), 7.79 (d, 2H, J=8.3 Hz), 8.06 (d, 2H, J=8.3 Hz), 9.85 (br s, 1H).

(g) Methyl 2'-trifluoromethanesulphonyloxy-[1,1';4',1"]terphenyl-4"-carboxylate In a manner similar to that of Example 13(a), starting with 2.90 g (9.5 mmol) of the compound obtained in Example 34(d), 3.62 mg (87%) of the expected product are obtained in the form of a beige-coloured powder with a melting point of 95° C.

$^1$H NMR (CDCl$_3$) δ 3.96 (s, 3H), 7.41 to 7.72 (m, 10H), 8.16 (d, 2H, J=8.5 Hz).

(h) 1-Bromo-3-(3-methylbut-2-enylsulphanyl)benzene 25.00 g (132.0 mmol) of 3-bromothiophenol, 200 ml of DMF and 18.23 g (138.0 mmol) of potassium carbonate are introduced into a three-necked flask. 18.0 ml (157.0 mmol) of 1-bromo-3-methyl-2-butene are added dropwise and the mixture is stirred at room temperature for five hours. The reaction medium is poured into water and extracted with ethyl acetate, and the organic phase is separated out after settling has taken place, washed with water, dried over magnesium sulphate and evaporated. 33.00 g (97%) of the expected compound are collected in the form of a yellow oil.

$^1$H NMR (CDCl$_3$) δ 1.62 (s, 3H), 1.73 (s, 3H), 3.54, (d, 2H, J=7.7 Hz), 5.28 (t, 1H, J=7.7 Hz), 7.09 to 7.15 (m, 1H), 7.22 to 7.31 (m, 2H), 7.45 (s, 1H).

(i) 7-Bromo-4,4-dimethylthiochroman 25.00 g (97.0 mmol) of 1-bromo-3-(3-methylbut-2-enylsulphonyl)benzene, 200 ml of toluene and 27.75 g (146.0 mmol) of para-toluenesulphonic acid are introduced into a three-necked flask. The reaction medium is refluxed for four hours and evaporated to dryness. The residue is taken up in aqueous sodium hydrogen carbonate solution and extracted with ethyl acetate, and the organic phase is separated out after settling has taken place, dried over magnesium sulphate and evaporated. The residue obtained is purified by chromatography on a column of silica eluted with heptane. 22.57 g (90%) of the expected compound are obtained in the form of a yellow oil.

$^1$H NMR (CDCl$_3$) δ 1.23 (s, 6H), 1.84 to 1.89 (m, 2H), 2.92 to 2.97 (m, 2H), 7.03 (dd, 1H, J=8.5/2.0 Hz), 7.13 (d, 1H, J=2.0 Hz).

(j) 7-Bromo-4,4-dimethylthiochromanboronic acid

In a manner similar to that of Example 1(a), starting with 5.00 g (20.4 mmol) of the compound obtained in Example 34(i), 2.63 g (61%) of the expected product are obtained in the form of a pale beige solid with a melting point of 242° C.

$^1$H NMR (CDCl$_3$) δ 1.37 (s, 6H), 1.98 to 2.02 (m, 2H), 3.05 to 3.10 (m, 2H), 7.48 (d, 1H, J=7.9 Hz), 7.82 (dd, 1H, J=7.9/1.2 Hz), 7.89 (d, 1H, J=1.0 Hz).

(k) Methyl 2'-(4,4-dimethylthiochroman-7-yl)-[1,1';4',1"]terphenyl-4"-carboxylate In a manner similar to that of Example 13(b), by reaction of 1.81 g (4.1 mmol) of the compound obtained in Example 34(g) with 1.04 g (5.0 mmol) of the boronic acid obtained in Example 34(j), 570 mg (30%) of the expected product are obtained in the form of a white solid with a melting point of 172° C.

$^1$H NMR (CDCl$_3$) δ 1.29 (s, 6H), 1.95 (t, 2H, J=5.9 Hz), 3.02 (t, 2H, J=5.9 Hz), 3.95 (s, 3H), 6.69 (dd, 1H, J=8.1/1.8 Hz), 7.04 (d, 1H, J=1.8 Hz), 7.14 (d, 1H, J=8.2 Hz), 7.19 to 7.26 (m, 5H), 7.50 (d, 1H, J=8.5 Hz), 7.65 to 7.67 (m, 2H), 7.73 (d, 2H, J=8.4 Hz), 8.12 (d, 2H, J=8.3 Hz).

(l) 2'-(4,4-Dimethylthiochroman-7-yl)-[1,1';4',1"]terphenyl-4"-carboxylic acid In a manner similar to that of Example 1(e), starting with 570 mg (1.2 mmol) of the ester obtained in Example 34(k), 500 mg (90%) of 2'-(4,4-dimethylthiochroman-7-yl)-[1,1';4',1"]terphenyl-4"-carboxylic acid are obtained in the form of a white crystalline solid with a melting point of 261° C.

$^1$H NMR (CDCl$_3$+2 drops of DMSO-$d_6$) δ 0.64 (s, 6H), 1.53 (t, 2H, J=5.9 Hz), 2.65 (5, 2H, J=6.0 Hz), 6.63 (d, 1H, J=1.6 Hz), 6.71 (d, 1H, J=8.0 Hz), 6.77 (dd, 1H, J=8.1/1.7 Hz), 6.84 to 6.97 (m, 5H), 7.19 (d, 1H, J=8.6 Hz), 7.32 to 7.36 (m, 2H), 7.42 (d, 2H, J=8.3 Hz), 7.81 (d, 2H, J=8.3 Hz)

Example 35

2'-(4,4-Dimethylthiochroman-6-yl)-[1,1';4',1"]-terphenyl-4"-carboxylic acid

(a) 1-Bromo-4-(3-methylbut-2-enylsulphanyl)benzene

In a manner similar to that of Example 34(h), by reaction of 30.00 g (159.0 mmol) of 4-bromo-thiophenol with 26.00 g (175.0 mmol) of 1-bromo-3-methyl-2-butene, 37.40 g (93%) of the expected product are obtained in the form of a yellow oil.

$^1$H NMR (CDCl$_3$) δ 1.59 (s, 3H), 1.71 (s, 3H), 3.51 (d, 2H, J=7.7 Hz), 5.27 (t, 1H, J=7.7 Hz), 7.19 (d, 2H, J=8.5 Hz), 7.38 (d, 2H, J=8.5 Hz).

(b) 6-Bromo-4,4-dimethylthiochroman

In a manner similar to that of Example 34(i), starting with 34.00 g (132.0 mmol) of the compound obtained in Example 35(a), 21.80 g (64%) of the expected product are obtained in the form of a brown solid with a melting point of 51° C.

$^1$H NMR (CDCl$_3$) δ 1.31 (s, 6H), 1.93 (t, 2H, J=6.0 Hz), 3.01 (t, 2H, J=6.1 Hz), 6.94 (d, 1H, J=8.4 Hz), 7.13 (dd, 1H, J=8.4/2.2 Hz), 7.45 (d, 1H, J=2.1 Hz).

(c) 6-Bromo-4,4-dimethylthiochromanboronic acid

In a manner similar to that of Example 1(a), starting with 5.00 g (20.4 mmol) of the compound obtained in Example 35(b), 2.28 g (53%) of the expected product are obtained in the form of a white solid with a melting point of 242° C.

$^1$H NMR (CDCl$_3$) δ 1.43 (s, 6H), 1.98 to 2.04 (m, 2H), 3.06 to 3.11 (m, 2H), 7.21 (d, 1H, J=7.8 Hz), 7.81 (dd, 1H, J=7.8/1.1 Hz), 8.20 (d, 1H, J=1.1 Hz).

(d) Methyl 2'-(4,4-dimethylthiochroman-6-yl)-[1,1'; 4',1"]terphenyl-4"-carboxylate In a manner similar to that of Example 13(b), by reaction of 1.81 g (4.1 mmol) of the compound obtained in Example 34(g) with 1.04 g (5.0 mmol) of the boronic acid obtained in Example 35(c), 680 mg (35%) of the expected product are obtained in the form of a colourless oil.

$^1$H NMR (CDCl$_3$) δ 1.27 (s, 6H), 1.83 to 1.88 (m, 2H), 2.94 to 2.99 (m, 2H), 3.94 (s, 3H), 6.96 (d, 1H, J=1.4 Hz), 7.04 to 7.25 (m, 7H), 7.51 (d, 1H, J=7.9 Hz), 7.65 (dd, 1H, J=7.9/2.0 Hz), 7.69 (d, 1H, J=1.8 Hz), 7.73 (d, 2H, J=8.5 Hz), 8.13 (d, 2H, J=8.5 Hz).

(e) 2'-(4,4-Dimethylthiochroman-6-yl)-[1,1';4',1"]-terphenyl-4"-carboxylic acid In a manner similar to that of Example 1(e), starting with 680 mg (1.5 mmol) of the ester obtained in Example 35(d), 280 mg (42%) of 2'-(4,4-dimethylthio-croman-6-yl)-[1,1';4',1"]terphenyl-4"-carboxylic acid are obtained in the form of a white crystalline solid with a melting point of 279° C.

$^1$H NMR (CDCl$_3$) δ 1.29 (s, 6H), 1.95 (t, 2H, J=5.9 Hz), 3.01 (t, 2H, J=5.9 Hz), 6.70 (dd, 1H, J=8.2/1.9 Hz), 7.01 (d, 1H, J=1.9 Hz), 7.15 (d, 1H, J=8.3 Hz), 7.17 to 7.42 (m, 5H), 7.50 (d, 1H, J=8.7 Hz), 7.65 to 7.69 (m, 2H), 7.73 (d, 2H, J=8.4 Hz), 8.13 (d, 2H, J=8.4 Hz).

Example 36

2'-(3,5,5,8,8-Pentamethyl-5,6,7,8-tetrahydro-2-naphthyl)-[1,1';4',1"]terphenyl-4"-carboxylic acid

(a) 6-Bromo-1,1,4,4,7-pentamethyl-1,2,3,4-tetrahydronaphthalene 18.31 g (100.0 mmol) of 2,5-dichloro-2,5-dimethylhexane, 17.10 g (100.0 mmol) of 2-bromotoluene and 200 ml of 1,2-dichloroethane are introduced into a three-necked flask under an argon atmosphere. 1.33 g (10.0 mmol) of aluminium chloride are added rapidly in a single portion and the reaction medium is stirred for thirty minutes at room temperature. The reaction medium is poured into water, extracted with dichloromethane and washed with water, and the organic phase is separated out after settling has taken place, dried over magnesium sulphate and evaporated. After recrystallization of the residue from methanol, 17.78 g (63%) of the expected compound are collected in the form of fine white crystals with a melting point of 73° C.

$^1$H NMR (CDCl$_3$) δ 1.25 (s, 12H), 1.65 (s, 4H), 2.33 (s, 3H), 7.14 (s, 1H), 7.42 (s, 1H).

(b) 5,6,7,8-Tetrahydro-3,5,5,8,8-pentamethyl-2-naphthylboronic acid

In a manner similar to that of Example 1(a), starting with 14.00 g (49.8 mmol) of the compound obtained in Example 36(a), 7.36 mg (60%) of the expected product are obtained in the form of a colourless oil.

$^1$H NMR (CDCl$_3$) δ 1.32 (s, 6H), 1.34 (s, 6H), 1.72 (s, 4H), 2.81 (s, 3H), 7.21 (s, 1H), 8.28 (s, 1H).

(c) Ethyl 4-[4-hydroxy-3-(5,6,7,8-tetrahydro-3,5,5,8,8-pentamethyl-2-naphthyl)phenyl]benzoate In a manner similar to that of Example 1(d), by reaction of 2.26 g (7.0 mmol) of the compound obtained in Example 1(c) with 2.08 g (8.4 mmol) of the boronic acid obtained in Example 36(b), 1.00 g (32%) of the expected product is obtained in the form of a colourless oil.

$^1$H NMR (CDCl$_3$) δ 1.27 (s, 6H), 1.33 (s, 6H), 1.41 (t, 3H, J=7.1 Hz), 1.71 (s, 4H), 2.17 (s, 3H), 4.39 (q, 2H, J=7.1 Hz), 5.05 (s, 1H), 7.09 (d, 1H, J=8.4 Hz), 7.21 (s, 1H), 7.25 (s, 1H), 7.45 (d, 1H, J=2.3 Hz), 7.56 (dd, 1H, J=8.4/2.3 Hz), 7.64 (d, 2H, J=8.4 Hz), 8.08 (d, 2H, J=8.4 Hz).

(d) Ethyl 3'-(3,5,5,8,8-pentamethyl-5,6,7,8-tetrahydro-2-naphthyl)-4'-trifluoromethanesulphonyloxy-biphenyl-4-carboxylate In a manner similar to that of Example 13(a), starting with 1.00 g (2.3 mmol) of the ester obtained in Example 36(c), 1.30 g (100%) of the expected product are obtained in the form of a yellow oil.

$^1$H NMR (CDCl$_3$) δ 1.26 (d, 6H, J=6.8 Hz), 1.31 (d, 6H, J=6.5 Hz), 1.42 (t, 3H, J=7.1 Hz), 1.71 (s, 4H), 2.15 (s, 3H), 4.40 (q, 2H, J=7.1 Hz), 7.16 (s, 1H), 7.21 (s, 1H), 7.43 to 7.47 (m, 1H), 7.64 to 7.68 (m, 2H), 7.67 (d, 2H, J=8.4 Hz), 8.13 (d, 2H, J=8.4 Hz).

(e) Ethyl 2'-(3,5,5,8,8-pentamethyl-5,6,7,8-tetrahydro-2-naphthyl)-[1,1';4',1"]terphenyl-4"-carboxylate In a manner similar to that of Example 13(b), by reaction of 1.00 g (1.7 mmol) of the compound obtained in Example 36(d) with 254 mg (2.1 mmol) of benzeneboronic acid, 770 mg (88%) of the expected product are obtained in the form of a colourless oil which is used directly in the following step.

(f) 2'-(3,5,5,8,8-Pentamethyl-5,6,7,8-tetrahydro-2-naphthyl)-[1,1';4',1"]terphenyl-4"-carboxylic acid In a manner similar to that of Example 1(e), starting with 770 mg (1.5 mmol) of the ester obtained in Example 36(e), 150 mg (21%) of 2'-(3,5,5,8,8-pentamethyl-5,6,7,8-tetrahydro-2-naphthyl)-[1,1';4',1"]terphenyl-4"-carboxylic acid are obtained in the form of a beige-coloured powder with a melting point of 217° C.

$^1$H NMR (CDCl$_3$+2 drops of DMSO-d$_6$) δ 1.20 (s, 6H), 1.26 (s, 6H), 1.63 (s, 4H), 2.11 (s, 3H), 6.28 (br s, 1H), 6.83 to 7.16 (m, 5H), 7.23 (s, 1H), 7.37 (d, 1H, J=2.2 Hz), 7.47 (dd, 1H, J=8.4/2.4 Hz), 7.57 (d, 2H, J=8.4 Hz), 8.02 (d, 2H, J=8.3 Hz).

Example 37

2'-(3-Methoxymethoxy-5,5,8,8-tetramethyl-5,6,7,8-tetrahydro-2-naphthyl)-[1,1';4',1"]terphenyl-4"-carboxylic acid

(a) 3-Bromo-5,5,8,8-tetramethyl-5,6,7,8-tetrahydro-2-naphthol

In a manner similar to that of Example 36(a), by reaction of 67.14 g (388.0 mmol) of 2-bromophenol with 71.10 g (388.0 mmol) of 2,5-dichloro-2,5-dimethylhexane, 86.13 g (78%) of the expected product are obtained in the form of a white solid with a melting point of 90–94° C.

$^1$H NMR (CDCl$_3$) δ 1.16 (s, 6H), 1.17 (s, 6H), 1.57 (s, 4H), 5.21 (s, 1H), 6.87 (s, 1H), 7.26 (s, 1H).

(b) 6-Bromo-7-methoxymethoxy-1-1-4-4-tetramethyl-1,2,3,4-tetrahydronaphthalene In a manner similar to that of Example 7(a), by reaction of 8.00 g (28.2 mmol) of the compound obtained in Example 37(a) with 2.36 ml (31.1 mmol) of chloromethyl methyl ether, 9.49 g (100%) of the expected product are obtained in the form of a beige-coloured oil.

$^1$H NMR (CDCl$_3$) δ 1.24 (s, 6H), 1.26 (s, 6H), 1.65 (s, 4H), 3.53 (s, 3H), 5.20 (s, 2H), 7.06 (s, 1H), 7.42 (s, 1H).

(c) 3-Methoxymethoxy-5,6,7,8-tetrahydro-5,5,8,8-tetramethyl-2-naphthylboronic acid In a manner similar to that of Example 1(a), starting with 9.49 g (29.0 mmol) of the compound obtained in Example 37(b), 8.21 g (97%) of the expected product are obtained in the form of a yellow oil.

$^1$H NMR (CDCl$_3$) δ 1.12 (s, 12H), 1.51 (s, 4H), 3.34 (s, 3H), 5.10 (s, 2H), 6.40 (s, 2H), 6.88 (s, 1H), 7.64 (s, 1H).

(d) Ethyl 4-[4-hydroxy-3-(3-methoxymethoxy-5,6,7,8-tetrahydro-5,5,8,8-tetramethyl-2-naphthyl)phenyl]benzoate In a manner similar to that of Example 1(d), by reaction of 8.10 g (25.2 mmol) of the compound obtained in Example 1(c) with 6.15 g (21.0 mmol) of the boronic acid obtained in Example 37(c), 5.26 g (51%) of the expected product are obtained in the form of a pale yellow oil.

$^1$H NMR (CDCl$_3$) δ 1.21 (s, 6H), 1.25 (s, 6H), 1.33 (t, 3H, J=7.1 Hz), 1.63 (s, 4H), 3.31 (s, 3H), 4.31 (q, 2H, J=7.1 Hz), 5.06 (s, 2H), 6.31 (s, 1H), 7.00 (d, H, J=8.3 Hz), 7.09 (s, 1H), 7.20 (s, 1H), 7.45 to 7.48 (dd, 1H, J=8.3/2.3 Hz), 7.51 (d, 1H, J=2.3 Hz), 7.57 (d, 2H, J=8.4 Hz), 8.01 (d, 2H, J=8.4 Hz).

(e) Ethyl 3'-(3-methoxymethoxy-5,5,8,8-tetramethyl-5,6,7,8-tetrahydro-2-naphthyl)-4'-trifluoromethane-sulphonyloxybiphenyl-4-carboxylate 4.76 g (9.7 mmol) of the ethyl ester obtained in Example 37(d), 2.64 g (9.7 mmol) of 4-nitrophenyl triflate, 2.64 g (1.9 mmol) of potassium carbonate and 100 ml of 1,2-dimethoxyethane are introduced into a three-necked flask under a stream of nitrogen. The reaction medium is stirred at room temperature for three hours and poured into a mixture of water and ethyl ether, and the organic phase is separated out after settling has taken place, extracted with ethyl ether, washed with water until the 4-nitrophenol has disappeared from the aqueous phase, dried over magnesium sulphate and evaporated. 6.05 g (100%) of the expected product are collected in the form of a beige-coloured oil.

$^1$H NMR (CDCl$_3$) δ 1.26 (t, 3H, J=7.1 Hz), 1.27 (s, 6H), 1.32 (s, 6H), 1.72 (s, 4H), 3.37 (s, 3H), 3.41 (q, 2H, J=7.1 Hz), 5.10 (s, 2H) 7.17 (s, 1H), 7.19 (s, 1H), 7.42 (d, 1H, J=8.5 Hz), 7.62 to 7.71 (m, 4H), 8.13 (d, 2H, J=8.4 Hz).

(f) Ethyl 2'-(3-methoxymethoxy-5,5,8,8-tetramethyl-5,6,7,8-tetrahydro-2-naphthyl)-[1,1';4',1"]terphenyl-4"-carboxylate In a manner similar to that of Example 13(b), by reaction of 6.59 g (10.6 mmol) of the compound obtained in Example 37(e) with 1.55 g (12.7 mmol) of benzeneboronic acid, 5.30 g (91%) of the expected product are obtained in the form of a colourless oil.

$^1$H NMR (CDCl$_3$) δ 1.26 (s, 6H), 1.27 (s, 6H), 1.30 (t, 3H, J=7.1 Hz), 1.60 to 1.64 (m, 4H), 3.22 (s, 3H), 4.41 (q, 2H, J=7.1 Hz), 4.75 (br s, 2H) 6.93 (s, 1H), 7.02 (s, 1H), 7.16 to 7.19 (m, 2H), 7.44 (d, 1H, J=8.5 Hz), 7.55 (d, 1H, J=8.0 Hz), 7.62 to 7.77 (m, 6H), 8.13 (d, 2H, J=7.6 Hz).

(g) 2'-(3-Methoxymethoxy-5,5,8,8-tetramethyl-5,6,7,8-tetrahydro-2-naphthyl)-[1,1';4',1"]terphenyl-4"-carboxylic acid In a manner similar to that of Example 1(e), starting with 1.00 g (1.8 mmol) of the ester obtained in Example 37(f), 540 mg (57%) of 2'-(3-methoxymethoxy-5,5,8,8-tetramethyl-5,6,7,8-tetrahydro-2-naphthyl)-[1,1';4',1]terphenyl-4"-carboxylic acid are obtained in the form of a white crystalline solid with a melting point of 219–222° C.

$^1$H NMR (CDCl$_3$) δ 1.03 (br s, 6H), 1.26 (s, 6H), 1.58 to 1.66 (m, 4H), 3.21 (s, 3H), 4.75 (br s, 2H), 6.93 (s, 1H), 7.01 (s, 1H), 7.16 to 7.21 (m, 5H), 7.55 (d, 1H, J=8.0 Hz), 7.68 (dd, 1H, J=8.0/1.9 Hz), 7.72 (s, 1H) 7.74 (d, 2H, J=8.4 Hz), 8.14 (d, 2H, J=8.4 Hz).

Example 38

2'-(3-Hydroxy-5,5,8,8-tetramethyl-5,6,7,8-tetrahydro-2-naphthyl)-[1,1';4',1"]terphenyl-4"-carboxylic acid

(a) Ethyl 2'-(3-hydroxy-5,5,8,8-tetramethyl-5,6,7,8-tetrahydro-2-naphthyl)-[1,1';4',1"]terphenyl-4"-carboxylate In a manner similar to that of Example 16(a), starting with 4.30 g (7.8 mmol) of the compound obtained in Example 37(f), 1.65 g (42%) of the expected product are obtained in the form of a white powder with a melting point of 145° C.

$^1$H NMR (CDCl$_3$) δ 0.98 (s, 6H), 1.24 (s, 6H), 1.42 (t, 3H, J=7.1 Hz), 1.56 to 1.64 (m, 4H), 4.41 (q, 2H, J=7.1 Hz), 4.76 (s, 1H), 6.80 (d, 2H, J=7.8 Hz), 7.13 to 7.23 (m, 5H), 7.62 (d, 1H, J=7.9 Hz), 7.72 to 7.73 (m, 1H), 7.74 (d, 2H, J=8.4 Hz), 8.13 (d, 2H, J=8.4 Hz).

(b) 2'-(3-Hydroxy-5,5,8,8-tetramethyl-5,6,7,8-tetrahydro-2-naphthyl)-[1,1';4',1"]terphenyl-4"-carboxylic acid In a manner similar to that of Example 1(e), starting with 600 mg (1.1 mmol) of the ester obtained in Example 38(a), 400 mg (70%) of 2'-(3-hydroxy-5,5,8,8-tetramethyl-5,6,7,8-tetrahydro-2-naphthyl)-[1,1';4',1"]terphenyl-4"-carboxylic acid are obtained in the form of a white crystalline solid with a melting point of 273° C.

$^1$H NMR (CDCl$_3$+2 drops of DMSO-d$_6$) δ 0.91 (s, 6H), 1.23 (s, 6H), 1.53 to 1.61 (m, 4H), 6.70 (s, 1H), 6.79 (s, 1H), 7.13 to 7.18 (m, 5H), 7.54 (d, 1H, J=8.0 Hz), 7.66 (dd, 1H, J=8.0/1.9 Hz), 7.74 (d, 2H, J=8.3 Hz), 7.82 (d, 1H, J=1.8 Hz), 8.10 (d, 2H, J=8.3 Hz), 8.18 (br s, 1H).

Example 39

2'-(3-Methoxy-5,5,8,8-tetramethyl-5,6,7,8-tetrahydro-2-naphthyl)-[(1,1';4',1"]terphenyl-4"-carboxylic acid (a) Ethyl 2'-(3-methoxy-5,5,8,8-tetramethyl-5,6,7,8-tetrahydro-2-naphthyl)-[1,1';4',1"]terphenyl-4"-carboxylate In a manner similar to that of Example 7(a), by reaction of 530 mg (1.1 mmol) of the compound obtained in Example 38(a) with 71 µl (1.1 mmol) of methyl iodide, 544 mg (100%) of the expected product are obtained in the form of a colourless oil.

$^1$H NMR (CDCl$_3$) δ 1.04 (s, 6H), 1.27 (s, 6H), 1.42 (t, 3H, J=7.1 Hz), 1.59 to 1.67 (m, 4H), 3.48 (s, 3H), 4.40 (q, 2H, J=7.1 Hz), 6.68 (s, 1H), 6.94 (s, 1H), 7.10 to 7.19 (m, 5H), 7.54 (d, 1H, J=8.0 Hz), 7.67 (dd, 1H, J=8.0/2.0 Hz), 7.73 to 7.74 (m, 1H), 7.75 (d, 2H, J=8.4 Hz), 8.12 (d, 2H, J=8.4 Hz).

(b) 2'-(3-Methoxy-5,5,8,8-tetramethyl-5,6,7,8-tetrahydro-2-naphthyl)-[1,1';4',1"]terphenyl-41"-carboxylic acid In a manner similar to that of Example 1(e), starting with 544 mg (1.0 mmol) of the ester obtained in Example 39(a), 490 mg (95%) of 2'-(3-methoxy-5,5,8,8-tetramethyl-5,6,7,8-tetrahydro-2-naphthyl)-[1,1';4',1"]terphenyl-4"-carboxylic acid are obtained in the form of a white crystalline solid with a melting point of 248° C.

$^1$H NMR (CDCl$_3$+2 drops of DMSO-d$_6$) δ 1.04 (s, 6H), 1.27 (s, 6H), 1.59 to 1.67 (m, 4H), 3.48 (s, 3H), 6.67 (s, 1H), 6.93 (s, 1H), 7.10 to 7.18 (m, 5H), 7.54 (d, 1H, J=8.0 Hz), 7.67 (dd, 1H, J=8.0/2.0 Hz), 7.73 (d, 2H, J=8.3 Hz), 7.74 (s, 1H), 8.13 (d, 2H, J=8.3 Hz).

Example 40

2'-(3-Propyloxy-5,5,8,8-tetramethyl-5,6,7,8-tetrahydro-2-naphthyl)-[1,1';4',1"]terphenyl-4"-carboxylic acid (a) Ethyl 2'-(3-propyloxy-5,5,8,8-tetramethyl-5,6,7,8-tetrahydro-2-naphthyl)-[1,1';4',1"]terphenyl-4"carboxylate In a manner similar to that of Example 7 (a), by reaction of 450 mg (8.3 mmol) of the compound obtained in Example 38(a) with 89 µl (9.2 mmol) of propyl iodide, 450 mg (92%) of the expected product are obtained in the form of a yellow solid with a melting point of 163° C., which is used directly in the following step.

(b) 2'-(3-Propyloxy-5,5,8,8-tetramethyl-5,6,7,8-tetrahydro-2-naphthyl)-[1,1';4',1"]terphenyl-4"-carboxylic acid In a manner similar to that of Example 1(e), starting with 450 mg (0.8 mmol) of the ester obtained in Example 40(a), 400 mg (94%) of 2'-(3-propyloxy-5,5,8,8-tetramethyl-5,6,7,8-tetrahydro-2-naphthyl)-[1,1';4',1"]terphenyl-4"-carboxylic acid are obtained in the form of a white crystalline solid with a melting point of 234° C.

$^1$H NMR (CDCl$_3$+2 drops of DMSO-d$_6$) δ 0.85 (t, 3H, J=7.5 Hz), 0.95 (br s, 6H), 1.27 (s, 6H), 1.54 to 1.70 (m, 6H), 3.72, (t, 2H, J=6.6 Hz), 6.73 (s, 1H), 6.82 (s, 1H), 7.11 to 7.17 (m, 5H), 7.53 (d, 1H, J=8.0 Hz), 7.66 (dd, 1H, J=8.0/1.9 Hz), 7.74 (d, 2H, J=8.4 Hz), 7.79 (d, 1H, J=1.8 Hz), 8.13 (d, 2H, J=8.3 Hz).

Example 41

3'-Methyl-2'-(5,5,8,8-tetramethyl-5,6,7,8-tetrahydro-2-naphthyl)-[1,1';4',1"]terphenyl-4"-carboxylic acid (a) 2-Bromo-4-nitrophenol 139.40 g (64.7 mmol) of 4-nitrophenol and 130 ml of dichloromethane are introduced into a three-necked flask under an argon atmosphere. The mixture is cooled to 0° C. and 3.31 ml (67.7 mmol) of bromine are added dropwise. The reaction medium is stirred for one hour at 0° C., 360 mg (6.5 mmol) of iron powder are then added and this mixture is stirred for sixteen hours at room temperature. The reaction medium is poured into water, a saturated sodium thiosulphate solution is added, this mixture is extracted with dichloromethane and washed with water, the organic phase is separated out after settling has taken place and dried over magnesium sulphate, and the solvents are evaporated off. 13.50 g (96%) of the expected compound are collected in the form of a beige-coloured powder with a melting point of 105–107° C.

$^1$H NMR (CDCl$_3$) δ 6.34 (br s, 1H), 7.13 (d, 1H, J=9.0 Hz), 8.16 (dd, 1H, J=9.1/2.7 Hz), 8.44 (d, 1H, J=2.7 Hz).

(b) 4-Nitro-2-(5,5,8,8-tetramethyl-5,6,7,8-tetrahydro-2-naphthyl)phenol

In a manner similar to that of Example 1(d), by reaction of 160.00 g (672.0 mmol) of the boronic acid obtained in Example 1(a) with 100.00 g (459.0 mmol) of the compound obtained in Example 41(a), 81.70 g (55%) of the expected compound are obtained in the form of a yellow oil.

$^1$H NMR (CDCl$_3$) δ 1.25 (s, 6H), 1.26 (s, 6H), 1.67 (s, 4H), 5.89 (br s, 1H), 7.00 (d, 1H, J=9.7 Hz), 7.13 (dd, 1H, J=8.1/1.9 Hz), 7.28 (d, 1H, J=1.9 Hz), 7.41 (d, 1H, J=8.1 Hz), 8.07 to 8.11 (m, 2H).

(c) 4-Nitro-2-(5,5,8,8-tetramethyl-5,6,7,8-tetrahydro-2-naphthyl)phenyl trifluoromethylsulphonate In a manner similar to that of Example 13(a), starting with 78.50 g (241.0 mmol) of the compound obtained in Example 41(b), 81.40 g (73%) of the expected product are obtained in the form of a grey powder with a melting point of 87–89° C.

$^1$H NMR (CDCl$_3$) δ 1.31 (s, 6H), 1.32 (s, 6H), 1.73 (s, 4H), 7.21 (dd, 1H, J=8.2/2.0 Hz), 7.39 (d, 1H, J=1.9 Hz), 7.44 (d, 1H, J=8.2 Hz), 7.56 (d, 1H, J=9.0 Hz), 8.27 (dd, 1H, J=9.0/2.9), 8.37 (d, 1H, J=2.8 Hz).

(d) 1,1,4,4-Tetramethyl-6-(4-nitrobiphenyl-2-yl)-1,2,3,4-tetrahydronaphthalene

In a manner similar to that of Example 13 (b), by reaction of 81.00 g (177.0 mmol) of the compound obtained in Example 41(c) with 32.20 g (265.0 mmol) of phenylboronic acid, 62.20 g (265.0 g) of the expected product are obtained in the form of a beige-coloured powder with a melting point of 181–183° C.

$^1$H NMR (CDCl$_3$) δ 0.90 (s, 6H), 1.26 (s, 6H), 1.56 to 1.64 (m, 4H), 6.84 (d, 1H, J=1.9 Hz), 7.09 to 7.15 (m, 3H), 7.25 to 7.30 (m, 4H), 7.56 (d, 1H, J=8.4 Hz), 8.21 (dd, 1H, J=8.5/2.4 Hz), 8.32 (d, 1H, J=2.4 Hz).

(e) 2-(5,5,8,8-Tetramethyl-5,6,7,8-tetrahydro-2-naphthyl)biphenyl-4-ylamine 62.00 g (160.0 mmol) of the compound obtained in Example 41(d) and one litre of methanol are introduced into a two-litre hydrogenator. The system is flushed with nitrogen, 1.85 g of 5% palladium on charcoal are added, the system is flushed with hydrogen and the reaction medium is stirred for six hours at 60° C. under a pressure of seven bar of hydrogen. After cooling the reaction medium and filtration through Celite®, the solvents are evaporated off and the product is purified by chromatography on a column of silica eluted with a mixture composed of 80% heptane and 20% ethyl acetate. After evaporation of the solvents, 43.00 g (75%) of the expected compound are collected in the form of an orange-coloured oil.

$^1$H NMR (CDCl$_3$) δ 1.25 (s, 12H), 1.53 to 1.63 (m, 4H), 3.74 (br s, 2H), 6.72 (dd, 1H, J=8.1/2.5 Hz), 6.79 (d, 1H, J=2.4 Hz), 6.86 (d, 1H, J=1.9 Hz), 7.04 to 7.24 (m, 8H).

(f) 6-(4-Iodobiphenyl-2-yl)-1,1,4,4-tetramethyl-1,2,3,4-tetrahydronaphthalene 40.00 g (113.0 mmol) of the compound obtained in Example 41(e) and 113 ml (113 mmol) of a 1 M solution of diiodomethane are introduced into a 500 ml round-bottomed flask under an argon atmosphere. 45.5 ml of isoamyl nitrite are added dropwise and the reaction mixture is heated at 60° C. for twenty minutes. After evaporation to dryness, the product is purified by chromatography on a column of silica eluted with a mixture composed of 90% heptane and 10% ethyl acetate. After evaporation of the solvents, 21.00 g (40%) of the expected compound are collected in the form of an off-white powder with a melting point of 120–122° C.

$^1$H NMR (CDCl$_3$) δ 0.89 (s, 6H), 1.25 (s, 6H), 1.54 to 1.62 (m, 4H), 6.80 (d, 1H, J=1.9 Hz), 7.03 to 7.24 (m, 8H), 7.70 (dd, 1H, J=8.1/1.9 Hz), 7.80 (d, 1H, J=1.8 Hz).

(g) 3-(5,5,8,8-Tetramethyl-5,6,7,8-tetrahydro-2-naphthyl)-4-phenylbenzeneboronic acid In a manner similar to that of Example 1(a), starting with 18.00 g (38.0 mmol) of the compound obtained in Example 41(f), 11.90 g (81%) of the expected product are obtained in the form of a pink-white solid with a melting point of 257–259° C.

$^1$H NMR (CDCl$_3$) δ 0.93 (s, 6H), 1.28 (s, 6H), 1.58 to 1.63 (m, 4H), 6.92 (d, 1H, J=1.7 Hz), 7.20 to 7.31 (m, 7H), 7.56 (d, 1H, J=7.6 Hz), 8.28 (dd, 1H, J=8.7/1.1 Hz), 8.34 (s, 1H).

(h) Methyl 3''-methyl-2'-(5,5,8,8-tetramethyl-5,6,7,8-tetrahydro-2-naphthyl)-[1,1';4',1'']terphenyl-4''-carboxylate In a manner similar to that of Example 1(d), by reaction of 700 mg (1.8 mmol) of the compound obtained in Example 41(g) with 380 mg (1.7 mmol) of methyl 2-methyl-4-bromobenzoate, 740 mg (91%) of the expected product are obtained in the form of a white solid with a melting point of 130–132° C.

$^1$H NMR (CDCl$_3$) δ 0.91 (s, 6H), 1.27 (s, 6H), 1.54 to 1.64 (m, 4H), 2.68 (s, 3H), 3.92 (s, 3H), 6.89 (d, 1H, J=1.7 Hz), 7.15 to 7.29 (m, 7H), 7.50 to 7.56 (m, 3H), 7.65 (dd, 1H, J=7.9/1.8 Hz), 7.72 (d, 1H, J=1.7 Hz), 8.02 (d, 1H, J=8.7 Hz).

(i) 3''-Methyl-2'-(5,5,8,8-tetramethyl-5,6,7,8-tetrahydro-2-naphthyl)-[1,1';4',1'']terphenyl-4''-carboxylic acid In a manner similar to that of Example 1(e), starting with 700 mg (1.4 mmol) of the ester obtained in Example 41(h), 537 mg (79%) of 3''-methyl-2'-(5,5,8,8-tetramethyl-5,6,7,8-tetrahydro-2-naphthyl)-[1,1';4'1'']terphenyl-4''-carboxylic acid are obtained in the form of a white crystalline solid with a melting point of 237–239° C.

$^1$H NMR (CDCl$_3$) δ 0.91 (s, 6H), 1.27 (s, 6H), 1.57 to 1.65 (m, 4H), 2.75 (s, 3H), 6.90 (d, 1H, J=1.8 Hz), 7.15 to 7.30 (m, 7H), 7.53 (d, 1H, J=7.9 Hz), 7.59 to 7.61 (m, 2H), 7.66 (dd, 1H, J=8.0/1.9 Hz), 7.74 (d, 1H, J=1.8 Hz), 8.19 (d, 1H, J=8.7 Hz).

Example 42

2''-Hydroxy-2'-(5,5,8,8-tetramethyl-5,6,7,8-tetrahydro-2-naphthyl)-[1,1';4',1'']terphenyl-4''-carboxylic acid

(a) 3-Hydroxy-4-iodobenzoic acid 25.00 g (180.0 mmol) of 3-hydroxybenzoic acid, 7.20 g (180.0 mmol) of sodium hydroxide pellets, 27.13 g (180.0 mmol) of sodium iodide and 500 ml of methanol are introduced into a one-litre three-necked flask under a stream of nitrogen. The mixture is cooled to 0° C. and 374.30 g (180.0 mmol) of an aqueous sodium hypochlorite solution are added dropwise over one hour and fifty minutes. The reaction medium is stirred for two hours at 0° C., a sodium thiosulphate solution is then added, the mixture is acidified at pH 5, extracted with ethyl ether, the organic phase is washed with water to neutral pH, dried over magnesium sulphate and filtered and the solvents are evaporated off. 43.80 g (92%) of the expected compound are collected in the form of a beige-coloured powder with a melting point of 198° C.

$^1$H NMR (CDCl$_3$) δ 7.13 (dd, 1H, J=8.1/1.9 Hz), 7.43 (d, 1H, J=1.8 Hz), 7.80 (d, 1H, J=8.1 Hz), 10.69 (br s, 1H), 12.98 (br s, 1H).

(b) Methyl 3-hydroxy-4-iodobenzoate

In a manner similar to that of Example 1(b), starting with 43.80 g (166.0 mmol) of the acid obtained in Example 42(a), 43.54 g (94%) of methyl 3-hydroxy-4-iodobenzoate are obtained in the form of a beige-coloured powder with a melting point of 153° C.

$^1$H NMR (CDCl$_3$) δ 3.89 (s, 3H), 7.25 (dd, 1H, J=8.2/1.9 Hz), 7.58 (d, 1H, J=1.9 Hz), 7.77 (d, 1H, J=8.2 Hz), 8.79 (br s, 1H).

(c) Methyl 2''-hydroxy-2'-(5,5,8,8-tetramethyl-5,6,7,8-tetrahydro-2-naphthyl)-[1,1';4',1'']terphenyl-4''-carboxylate In a manner similar to that of Example 1(d), by reaction of 2.80 g (7.3 mmol) of the boronic acid obtained in Example 41(g) with 1.84 g (6.6 mmol) of the compound obtained in Example 42(b), 2.00 g (62%) of the expected product are obtained in the form of a white solid with a melting point of 183–185° C.

$^1$H NMR (CDCl$_3$) δ 0.89 (s, 6H), 1.26 (s, 6H), 1.56 to 1.64 (m, 4H), 3.94 (s, 3H), 5.51 (s, 1H), 6.89 (d, 1H, J=1.9 Hz), 7.18 to 7.26 (m, 7H), 7.42 (d, 1H, J=8.3 Hz), 7.53 to 7.55 (m, 2H), 7.59 to 7.60 (m, 1H), 7.68 to 7.71 (m, 2H)

(d) 2"-Hydroxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 500 mg (1.0 mmol) of the ester obtained in Example 42(c), 480 mg (99%) of 2"-hydroxy-2'-(5,5,8,8-tetramethyl-5,6,7,8-tetrahydro-2-naphthyl)-[1,1';4',1"]terphenyl-4"-carboxylic acid are obtained in the form of a white crystalline solid with a melting point of 282–284° C.

$^1$H NMR (CDCl$_3$+2 drops of DMSO-d$_6$) δ 0.90 (s, 6H), 1.25 (s, 6H), 1.55 to 1.63 (m, 4H), 6.88 (d, 1H, J=1.5 Hz), 7.12 to 7.25 (m, 7H), 7.43 (d, 1H, J=8.1 Hz), 7.47 (d, 1H, J=8.7 Hz), 7.61 (s, 1H), 7.65 to 7.67 (m, 1H), 7.71 (d, 2H, J=7.6 Hz).

Example 43

2"-Methoxymethoxy-2'-(5,5,8,8-tetramethyl-5,6,7,8-tetrahydro-2-naphthyl)-[1,1';4',1"]terphenyl-4"-carboxylic acid (a) Methyl 2"-methoxymethoxy-2'-(5,5,8,8-tetramethyl-5,6,7,8-tetrahydro-2-naphthyl)-[1,1';4',1"]terphenyl-4"-carboxylate In a manner similar to that of Example 7(a), by reaction of 580 mg (1.2 mmol) of the compound obtained in Example 42(c) with 103 µl (1.3 mmol) of chloromethyl methyl ether, 630 mg (100%) of the expected product are obtained in the form of an orange-coloured oil.

$^1$H NMR (CDCl$_3$) δ 0.91 (s, 6H), 1.26 (s, 6H), 1.56 to 1.63 (m, 4H), 3.48 (s, 3H), 3.94 (s, 3H), 5.26 (s, 2H), 6.91 (d, 1H, J=1.8 Hz), 7.10 (dd, 1H, J=7.9/1.9 Hz), 7.19 to 7.25 (m, 6H), 7.46 to 7.51 (m, 2H), 7.61 (dd, 1H, J=7.8/1.7 Hz), 7.65 (d, 1H, J=1.7 Hz), 7.79 (dd, 1H, J=7.9/1.8 Hz), 7.89 (d, 1H, J=1.5 Hz).

(b) 2"-Methoxymethoxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 620 mg (1.2 mmol) of the ester obtained in Example 43(a), 556 mg (92%) of 2"-methoxymethoxy-2'-(5,5,8,8-tetramethyl-5,6,7,8-tetrahydro-2-naphthyl)-[1,1';4',1"]terphenyl-4"-carboxylic acid are obtained in the form of a white crystalline solid with a melting point of 204–206° C.

$^1$H NMR (CDCl$_3$) δ 0.92 (s, 6H), 1.26 (s, 6H), 1.56 to 1.64 (m, 4H), 3.49 (s, 3H), 5.28 (s, 2H), 6.92 (d, 1H, J=1.7 Hz), 7.12 (dd, 1H, J=7.9/1.8 Hz), 7.18 to 7.26 (m, 6H), 7.49 (d, 1H, J=7.9 Hz), 7.54 (d, 1H, J=8.0/1.8 Hz), 7.67 (d, 1H, J=1.6 Hz), 7.88 (dd, 1H, J=7.9/1.8 Hz), 7.99 (d, 1H, J=1.4 Hz).

Example 44

2"-Methoxy-2'-(5,5,8,8-tetramethyl-5,6,7,8-tetrahydro-2-naphthyl)-[1,1 ';4',1"]terphenyl-4"-carboxylic acid (a) Methyl 2"-methoxy-2'-(5,5,8,8-tetramethyl-5,6,7,8-tetrahydro-2-naphthyl)-[1,1';4',1"]terphenyl-4"-carboxylate In a manner similar to that of Example 7(a), by reaction of 500 mg (1.0 mmol) of the compound obtained in Example 42(c) with 70 µl (1.1 mmol) of methyl iodide, 510 mg (99%) of the expected product are obtained in the form of a pale beige powder with a melting point of 144–146° C.

$^1$H NMR (CDCl$_3$) δ 0.90 (s, 6H), 1.26 (s, 6H), 1.56 to 1.63 (m, 4H), 3.93 (s, 3H), 3.95 (s, 3H), 6.90 (d, 1H, J=1.8 Hz), 7.14 to 7.26 (m, 7H), 7.46 (s, 1H), 7.49 (s, 1H), 7.61 (dd, 1H, J=7.9/1.8 Hz), 7.66 (d, 1H, J=8.0 Hz), 7.67 (d, 1H, J=1.3 Hz), 7.73 (d, 1H, J=7.8 Hz).

(b) 2"-Methoxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 500 mg (1.0 mmol) of the ester obtained in Example 44(a), 420 mg (86%) of 20"-methoxy-2'-(5,5,8,8-tetramethyl-5,6,7,8-tetrahydro-2-naphthyl)-[1,1';4',1"]terphenyl-4"-carboxylic acid are obtained in the form of a white crystalline solid with a melting point of 272–274° C.

$^1$H NMR (CDCl$_3$+2 drops of DMSO-d$_6$) δ 0.91 (s, 6H), 1.26 (s, 6H), 1.55 to 1.63 (m, 4H), 3.92 (s, 3H), 6.90 (d, 1H, J=1.8 Hz), 7.13 to 7.25 (m, 7H), 7.45 (d, 1H, J=1.4 Hz), 7.49 (d, 1H, J=1.3 Hz), 7.62 (dd, 1H, J=7.9/1.8 Hz), 7.65 (d, 1H, J=1.6 Hz), 7.71 (s, 1H), 7.75 (d, 1H, J=8.1 Hz).

Example 45

2"-Propyloxy-2'-(5,5,8,8-tetramethyl-5,6,7,8-tetrahydro-2-naphthyl)-[1,1';4',1"]terphenyl-4"-carboxylic acid (a) Methyl 2"-propyloxy-2'-(5,5,8,8-tetramethyl-5,6,7,8-tetrahydro-2-naphthyl)-[1,1';4',1"]terphenyl-4"-carboxylate In a manner similar to that of Example 7 (a), by reaction of 500 mg (1.0 mmol) of the compound obtained in Example 42(c) with 110 µl (1.1 mmol) of propyl iodide, 530 mg (98%) of the expected product are obtained in the form of a brown-coloured oil.

$^1$H NMR (CDCl$_3$) δ 0.91 (s, 6H), 1.03 (t, 3H, J=7.5 Hz), 1.25 (s, 6H), 1.55 to 1.63 (m, 4H), 1.86 (sext, 2H, J=6.8 Hz), 3.94 (s, 3H), 4.06 (t, 2H, J=6.5 Hz), 6.90 (d, 1H, J=1.8 Hz), 7.12 (dd, 1H, J=8.0/1.8 Hz), 7.17 to 7.26 (m, 6H), 7.47 (d, 1H, J=7.9 Hz), 7.50 (d, 1H, J=7.9 Hz), 7.64 to 7.69 (m, 4H).

(b) 2"-Propyloxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 520 mg (1.0 mmol) of the ester obtained in Example 45(a), 385 mg (77%) of 2"-propyloxy-2'-(5,5,8,8-tetramethyl-5,6,7,8-tetrahydro-2-naphthyl)-[1,1';4',1"]terphenyl-4"-carboxylic acid are obtained in the form of a white crystalline solid with a melting point of 216–218° C.

$^1$H NMR (CDCl$_3$) δ 0.92 (s, 6H), 1.04 (t, 3H, J=7.5 Hz), 1.26 (s, 6H), 1.56 to 1.64 (m, 4H), 1.87 (sext, 2H, J=6.9 Hz), 4.08 (t, 2H, J=6.5 Hz), 6.92 (d, 1H, J=1.8 Hz), 7.14 to 7.25 (m, 7H), 7.48 (d, 1H, J=7.9 Hz), 7.55 (d, 1H, J=7.9 Hz), 7.66 to 7.74 (m, 3H), 7.82 (d, 1H, J=8.0 Hz).

Example 46

3"-Hydroxy-2'-(5,5,8,8-tetramethyl-5,6,7,8-tetrahydro-2-naphthyl)-[1,1';4',1"]terphenyl-4"-carboxylic acid

(a) Methyl 3"-hydroxy-2'-(5,5,8,8-tetramethyl-5,6,7,8-tetrahydro-2-naphthyl)-[1,1';4',1"]terphenyl-4"-carboxylate In a manner similar to that of Example 1(d), by reaction of 700 mg (1.8 mmol) of the boronic acid obtained in Example 41(g) with 420 mg (1.5 mmol) of methyl 4-iodosalicylate, 550 mg (75%) of the expected product are obtained in the form of yellow crystals with a melting point of 134–136° C.

$^1$H NMR (CDCl$_3$) δ 0.91 (s, 6H), 1.27 (s, 6H), 1.55 to 1.65 (m, 4H), 3.98 (s, 3H), 6.88 (d, 1H, J=1.9 Hz), 7.14 to 7.31 (m, 9H), 7.51 (d, 1H, J=7.9 Hz), 7.65 (dd, 1H, J=7.9/2.0 Hz), 7.72 (d, 1H, J=1.9 Hz), 7.91 (d, 1H, J=8.0 Hz), 10.82 (s, 1H).

(b) 3"-Hydroxy-2'-(5,5,8,8-tetramethyl-5,6,7,8-tetrahydro-2-naphthyl)-[1,1';4',1"]terphenyl-4"-carboxylic acid In a manner similar to that of Example 1(e), starting with 550 mg (1.1 mmol) of the ester obtained in Example 46(a), 277 mg (52%) of 3"-hydroxy-2'-(5,5,8,8-tetramethyl-5,6,7,8-tetrahydro-2-naphthyl)-[1,1';4',1"]terphenyl-4"-carboxylic acid are obtained in the form of a white crystalline solid with a melting point of 266–268° C.

$^1$H NMR (CDCl$_3$) δ 0.91 (s, 6H), 1.27 (s, 6H), 1.56 to 1.64 (m, 4H), 6.89 (d, 1H, J=1.7 Hz), 7.14 to 7.25 (m, 9H), 7.28 (d, 1H, J=2.9 Hz), 7.50 (d, 1H, J=8.0 Hz), 7.65 (dd, 1H, J=8.0/1.8 Hz), 7.72 (d, 1H, J=1.7 Hz), 7.95 (d, 1H, J=8.2 Hz).

Example 47

6-[2-(5,5,8,8-Tetramethyl-5,6,7,8-tetrahydro-2-naphthyl)biphenyl-4-yl]nicotinic acid

(a) Ethyl 6-[2-(5,5,8,8-tetramethyl-5,6,7,8-tetrahydro-2-naphthyl)biphenyl-4-yl]nicotinate In a manner similar to that of Example 1(d), by reaction of 700 mg (1.8 mmol) of the boronic acid obtained in Example 41(g) with 460 mg (1.7 mmol) of ethyl 6-iodonicotinate, 650 mg (80%) of the expected product are obtained in the form of a white solid with a melting point of 105–107° C.

$^1$H NMR (CDCl$_3$) δ 0.92 (s, 6H), 1.28 (s, 6H), 1.45 (t, 3H, J=7.1 Hz), 1.57 to 1.65 (m, 4H), 4.44 (q, 2H, J=7.1 Hz), 6.89 (d, 1H, J=1.8 Hz), 7.18 to 7.30 (m, 6H), 7.57 (d, 1H, J=7.9 Hz), 7.89 (d, 1H, J=8.3 Hz), 8.10 to 8.15 (m, 2H), 8.36 (dd, 1H, J=8.3/2.2 Hz), 9.31 (d, 1H, J=2.1 Hz).

(b) 6-[2-(5,5,8,8-Tetramethyl-5,6,7,8-tetrahydro-2-naphthyl)biphenyl-4-yl]nicotinic acid In a manner similar to that of Example 1(e), starting with 650 mg (1.3 mmol) of the ester obtained in Example 47(a), 490 mg (80%) of 6-[2-(5,5,8,8-tetramethyl-5,6,7,8-tetrahydro-2-naphthyl)biphenyl-4-yl]-nicotinic acid are obtained in the form of a white solid crystallized as fine needles, with a melting point of 319–321° C.

$^1$H NMR (CDCl$_3$) δ 1.04 (s, 6H), 1.26 (s, 6H), 1.57 to 1.63 (m, 4H), 7.21 to 7.41 (m, 7H), 7.58 (s, 1H), 7.65 (d, 1H, J=8.1 Hz), 8.15 (d, 1H, J=8.3 Hz), 8.41 (dd, 1H, J=8.1/1.9 Hz), 8.59 (d, 1H, J=1.8 Hz), 8.69 (d, 1H, J=2.2 Hz), 9.82 (d, 1H, J=1.9 Hz).

Example 48

5-[2-(5,5,8,8-Tetramethyl-5,6,7,8-tetrahydro-2-naphthyl)biphenyl-4-yl]-2-pyridinecarboxylic acid

(a) Methyl 5-[2-(5,5,8,8-tetramethyl-5,6,7,8-tetrahydro-2-naphthyl)biphenyl-4-yl]-2-pyridinecarboxylate In a manner similar to that of Example 1(d), by reaction of 700 mg (1.8 mmol) of the boronic acid obtained in Example 41(g) with 430 mg (1.7 mmol) of methyl 5-iodo-2-pyridinecarboxylate, 600 mg (77%) of the expected product are obtained in the form of a white solid with a melting point of 160–162° C.

$^1$H NMR (CDCl$_3$) δ 0.91 (s, 6H), 1.27 (s, 6H), 1.55 to 1.65 (m, 4H), 4.05 (s, 3H), 6.90 (d, 1H, J=1.8 Hz), 7.16 to 7.30 (m, 7H), 7.57 (d, 1H, J=7.9 Hz), 7.67 (dd, 1H, J=8.0/1.9 Hz), 7.72 (d, 1H, J=1.9 Hz), 8.10 (dd, 1H, J=8.2/2.2 Hz), 8.24 (d, 1H, J=8.2 Hz), 9.06 (d, 1H, J=2.1 Hz).

(b) 5-[2-(5,5,8,8-Tetramethyl-5,6,7,8-tetrahydro-2-naphthyl)biphenyl-4-yl]-2-pyridinecarboxylic acid In a manner similar to that of Example 1(e), starting with 600 mg (1.3 mmol) of the ester obtained in Example 48(a), 490 mg (84%) of 5-[2-(5,5,8,8-tetramethyl-5,6,7,8-tetrahydro-2-naphthyl)biphenyl-4-yl]-2-pyridinecarboxylic acid are obtained in the form of a beige-coloured powder with a melting point of 222–224° C.

$^1$H NMR (CDCl$_3$) δ 0.92 (s, 6H), 1.27 (s, 6H), 1.57 to 1.65 (m, 4H), 6.89 (d, 1H, J=1.6 Hz), 7.13 to 7.30 (m, 7H), 7.58 (d, 1H, J=7.9 Hz), 7.68 (dd, 1H, J=8.0/1.5 Hz), 7.73 (s, 1H).

Example 49

2'-(5,5,8,8-Tetramethyl-5,6,7,8-tetrahydro-2-naphthyl)-[1,1';4',1"]terphenyl-4"-hydroxamic acid 2.00 g (4.3 mmol) of the acid obtained in Example 14, 30 ml of ethanol and 290 mg (5.2 mmol) of powdered potassium hydroxide are successively introduced into a three-necked flask under a stream of nitrogen. The reaction medium is stirred for thirty minutes at room temperature and is then evaporated to dryness. The residue is taken up in 80 ml of dichloromethane and 673 mg (4.8 mmol) of O-(trimethylsilyl)hydroxylamine and 645 mg (4.8 mmol) of 1-hydroxybenzotriazole (HOBT) are added. After cooling the reaction medium to 0° C., 915 mg (4.8 mmol) of 1-(3-dimethylaminopropyl)-3-ethylcarbodiimide hydrochloride (EDCI) are added and the solution obtained is stirred for one hour at 0° C. and then for sixteen hours at room temperature. The reaction medium is poured into a water/dichloromethane mixture and extracted with dichloromethane, and the organic phase is washed with water to neutral pH, dried over magnesium sulphate and evaporated. The residue obtained is purified by chromatography on a column of silica eluted with a mixture composed of 20% ethyl acetate and 80% heptane. After evaporation of the solvents, 530 mg (22%) of the expected product are collected in the form of a beige-coloured solid with a melting point of 105–108° C.

¹H NMR (CDCl₃) δ 0.90 (s, 6H), 1.26 (s, 6H), 1.55 to 1.63 (m, 6H), 4.70 to 5.20 (m, 2H), 6.88 (s, 1H), 7.12 to 7.27 (m, 7H), 7.49 (d, 1H, J=7.9 Hz), 7.60 (d, 1H, J=8.0 Hz), 7.70 (d, 1H, J=1.3 Hz), 7.73 (d, 2H, J=8.2 Hz), 7.84 (d, 2H, J=8.1 Hz).

Example 50

2'-(5,5,8,8-Tetramethyl-5,6,7,8-tetrahydro-2-naphthyl)-[1,1';4',1"]terphenyl-4"-ol In a manner similar to that of Example 1(d), by reaction of 700 mg (1.8 mmol) of the boronic acid obtained in Example 41(g) with 287 mg (1.7 mmol) of 4-bromophenol, 560 mg (89%) of 2'-(5,5,8,8-tetramethyl-5,6,7,8-tetrahydro-2-naphthyl)-[1,1';4',1"]terphenyl-4"-ol are obtained in the form of a colourless oil.

¹H NMR (CDCl₃) δ 0.91 (S, 6H), 1.26 (s, 6H), 1.56 to 1.64 (m, 4H), 4.88 (s, 1H), 6.90 to 6.94 (m, 3H), 7.14 to 7.22 (m, 7H), 7.47 (d, 1H, J=7.9 Hz), 7.57 (d, 2H, J=8.0 Hz), 7.57 to 7.59 (m, 1H), 7.65 (d, 1H, J=1.9 Hz).

Example 51

[2'-(5,5,8,8-Tetramethyl-5,6,7,8-tetrahydro-2-naphthyl)-[1,1';4',1"]terphenyl-4"-yl]methanol 1.80 g (3.7 mmol) of the ester obtained in Example 13(b) and 30 ml of toluene are introduced into a two-litre three-necked flask under a stream of nitrogen. The solution obtained is cooled to −78° C. and 14.7 ml (14.7 mmol) of a solution (1 M in toluene) of diisobutylaluminium hydride is added dropwise. The reaction medium is stirred for one hour at −78° C., hydrolysed with 1 N hydrochloric acid and filtered. The organic phase is washed with water to neutral pH, dried over magnesium sulphate and filtered and the solvents are evaporated off. After evaporation of the solvents, 1.31 g (79%) of [2'-(5,5,8,8-Tetramethyl-5,6,7,8-tetrahydro-2-naphthyl)-[1,1';4',1"]terphenyl-4"-yl]methanol are collected in the form of an orange-coloured solid with a melting point of 134–136° C.

¹H NMR (CDCl₃) δ 0.91 (s, 6H), 1.27 (s, 6H), 1.57 to 1.64 (m, 4H), 1.72 (br s, 1H), 4.75 (d, 2H, J=3.4 Hz), 6.90 (d, 1H, J=1.9 Hz), 7.14 to 7.28 (m, 7H), 7.44 to 7.51 (m, 3H), 7.63 (dd, 1H, J=8.0/1.9 Hz), 7.67 to 7.71 (m, 3H).

Example 52

2'-(5,5,8,8-Tetramethyl-5,6,7,8-tetrahydro-2-naphthyl)-[1,1';4',1"]terphenyl-4"-carbaldehyde 640 mg (1.4 mmol) of the alcohol obtained in Example 51, 2.50 g (28.7 mmol) of manganese oxide and 50 ml of dichloromethane are mixed together in a 500 ml round-bottomed flask. The reaction medium is stirred for twenty hours at room temperature, the manganese oxide is then filtered off and the dichloromethane is evaporated off. The residue obtained is purified by chromatography on a column of silica eluted with a mixture composed of 80% heptane and 20% ethyl acetate. After evaporation of the solvents, 90 mg (14%) of the expected compound are collected in the form of a white powder with a melting point of 120–122° C.

¹H NMR (CDCl₃) δ 0.91 (s, 6H), 1.27 (s, 6H), 1.56 to 1.64 (m, 4H), 6.90 (d, 1H, J=1.8 Hz), 7.14 to 7.29 (m, 7H), 7.54 (d, 1H, J=8.0 Hz), 7.66 (dd, 1H, J=7.9/2.0 Hz), 7.74 (d, 1H, J=1.9 Hz), 7.84 (d, 2H, J=8.3 Hz), 7.97 (d, 2H, J=8.3 Hz), 10.07 (s, 1H).

Example 53

4'-Methoxycarbonylmethoxy-3'-(5,5,8,8-tetramethyl-5,6,7,8-tetrahydro-2-naphthyl)biphenyl-4-carboxylic acid (a) Benzyl 4-[4-hydroxy-3-(5,6,7,8-tetrahydro-5,5,8,8-tetramethyl-2-naphthyl)phenyl]benzoate 6.00 g (15.0 mmol) of the compound obtained in Example 1(e) and 140 ml of DMF are introduced into a round-bottomed flask under a stream of nitrogen. The mixture is cooled to 0° C., 502 mg (15.7 mmol) of sodium hydride (80% in oil) are added portionwise and this mixture is stirred until the evolution of gas has ceased. 1.87 ml (15.7 mmol) of benzyl bromide are then added and the mixture is stirred for one hour at 0° C. and then for sixteen hours at room temperature. The reaction medium is poured into a 2N HCl/ethyl acetate mixture and extracted with ethyl acetate, and the organic phase is separated out after settling has taken place, dried over magnesium sulphate and evaporated. The residue obtained is purified by chromatography on a column of silica eluted with a mixture composed of 20% ethyl acetate and 80% heptane. After evaporation of the solvents, 5.21 g (71%) of the expected product are collected in the form of a yellow crystalline solid with a melting point of 90–91° C.

¹H NMR (CDCl₃) δ 1.34 (s, 6H), 1.36 (s, 6H), 1.76 (s, 4H), 5.40 (s, 2H), 5.47 (s, 1H), 7.11 (d, 1H, J=8.8 Hz), 7.27 to 7.30 (m, 1H), 7.38 to 7.56 (m, 9H), 7.66 (d, 2H, J=8.4 Hz), 8.14 (d, 2H, J=8.4 Hz).

(b) Benzyl 4'-methoxycarbonylmethoxy-3'-(5,5,8,8-tetramethyl-5,6,7,8-tetrahydro-2-naphthyl)biphenyl-4-carboxylate In a manner similar to that of Example 2(a), by reaction of 1.20 g (2.44 mmol) of the compound obtained in Example 53(a) with 280 μl (2.9 mmol) of methyl bromoacetate, 950 mg (70%) of the expected product are obtained in the form of a white solid with a melting point of 104–106° C.

¹H NMR (CDCl₃) δ 1.27 (s, 6H), 1.33 (s, 6H), 1.72 (s, 4H), 3.80 (s, 3H), 4.67 (s, 2H), 5.38 (s, 2H), 6.95 (d, 1H, J=8.5 Hz), 7.37 to 7.54 (m, 8H), 7.60 to 7.62 (m, 2H), 7.64 (d, 2H, J=8.5 Hz), 8.12 (d, 2H, J=8.5 Hz).

(c) 4'-Methoxycarbonylmethoxy-3'-(5,5,8,8-tetramethyl-5,6,7,8-tetrahydro-2-naphthyl)biphenyl-4-carboxylic acid 300 mg (0.53 mmol) of the compound obtained in Example 53(b), 20 ml of methanol and 10 ml of THF are introduced into a three-necked flask under a stream of argon. The medium is degassed with argon, 60.0 mg of 15% palladium on charcoal are introduced, the system is purged with hydrogen and the reaction medium is stirred under a hydrogen atmosphere (slight excess pressure) for 22 hours. The catalyst is filtered off through Celite®, the solvents are evaporated off, the product obtained is crystallized from a mixture composed of 10% ethyl ether and 90% heptane, and 142 mg (57%) of the expected product are collected in the form of a white crystalline solid with a melting point of 234–238° C.

¹H NMR (CDCl₃) δ 1.33 (s, 12H), 1.72 (s, 4H), 3.80 (s, 3H), 4.68 (s, 2H), 6.95 (d, 1H, J=8.5 Hz), 7.33 to 7.40 (m, 2H), 7.53 (dd, 1H, J=8.5/2.3 Hz), 7.60 to 7.66 (m, 4H), 8.11 (br d, 2H, J=7.8 Hz).

Example 54

4'-Carboxymethoxy-3'-(5,5,8,8-tetramethyl-5,6,7,8-tetrahydro-2-naphthyl)biphenyl-4'-carboxylic acid In a manner similar to that of Example 1(e), starting with 650 mg (1.2 mmol) of the diester obtained in Example 53(b), 470 mg (88%) of 4'-carboxymethoxy-3'-(5,5,8,8-tetramethyl-5,6,7,8-tetrahydro-2-naphthyl)biphenyl-4'-carboxylic acid are obtained in the form of a white crystalline solid with a melting point of 279–281° C.

$^1$H NMR (CDCl$_3$+2 drops of DMSO-d$_6$) δ 1.33 (s, 12H), 1.72 (s, 4H), 4.65 (s, 2H), 6.99 (d, 1H, J=8.6 Hz), 7.38 (d, 1H, J=7.3 Hz), 7.41 (d, 1H, J=8.2 Hz), 7.53 (dd, 1H, J=8.5/2.4 Hz), 7.60 to 7.62 (m, 2H), 7.64 (d, 2H, J=8.4 Hz), 8.09 (d, 2H, J=8.4 Hz)

Example 55

4'-(5-Ethoxycarbonylpentyloxy)-3'-(5,5,8,8-tetramethyl-5,6,7,8-tetrahydro-2-naphthyl)biphenyl-4-carboxylic acid (a) Benzyl 4'-(5-ethoxycarbonylpentyloxy)-3'-(5,5,8,8-tetramethyl-5,6,7,8-tetrahydro-2-naphthyl)biphenyl-4-carboxylate In a manner similar to that of Example 2(a), by reaction of 1.20 g (2.4 mmol) of the compound obtained in Example 53(a) with 520 μl (2.9 mmol) of ethyl 6-bromohexanoate, 1.52 g (100%) of the expected product are obtained in the form of a yellow oil.

$^1$H NMR (CDCl$_3$) δ 1.24 (t, 3H, J=7.1 Hz), 1.32 (s, 6H), 1.33 (s, 6H), 1.42 to 1.49 (m, 2H), 1.64 (quint, 2H, J=8.0 Hz), 1.72 (s, 4H), 1.78 (quint, 2H, J=7.1 Hz), 2.27 (t, 2H, J=7.6 Hz), 4.02 (t, 2H, J=6.5 Hz), 4.11 (q, 2H, J=7.1 Hz), 5.38 (s, 2H), 7.03 (d, 1H, J=8.6 Hz), 7.32 to 7.57 (m, 8H), 7.57 (d, 1H, J=1.5 Hz), 7.61 (d, 1H, J=2.4 Hz), 7.65 (d, 2H, J=8.4 Hz), 8.12 (d, 2H, J=8.5 Hz).

(b) 4'-(5-Ethoxycarbonylpentyloxy)-3"-(5,5,8,8-tetramethyl-5,6,7,8-tetrahydro-2-naphthyl)biphenyl-4-carboxylic acid In a manner similar to that of Example 53(c), starting with 620 mg (1.0 mmol) of the diester obtained in Example 55(a), 420 mg (80%) of 4'-(5-ethoxycarbonylpentyloxy)-3'-(5,5,8,8-tetramethyl-5,6,7,8-tetrahydro-2-naphthyl)biphenyl-4-carboxylic acid are obtained in the form of a white crystalline solid with a melting point of 177° C.

$^1$H NMR (CDCl$_3$) δ 1.25 (t, 3H, J=7.2 Hz), 1.32 (s, 6H), 1.33 (s, 6H), 1.41 to 1.49 (m, 2H), 1.59 to 1.68 (m, 2H), 1.73 (s, 4H), 1.78 to 1.83 (m, 2H), 2.27 (t, 2H, J=7.6 Hz), 4.03 (t, 2H, J=6.5 Hz), 4.12 (q, 2H, J=7.1 Hz), 7.04 (d, 1H, J=8.6 Hz), 7.30 to 7.38 (m, 2H), 7.53 (d, 1H, J=2.1 Hz), 7.58 (d, 1H, J=1.4 Hz), 7.63 (d, 1H, J=2.3 Hz), 7.69 (d, 2H, J=7.9 Hz), 8.16 (br d, 2H, J=6.7 Hz).

Example 56

4'-(5-Carboxypentyloxy)-3'-(5,5,8,8-tetramethyl-5,6,7,8-tetrahydro-2-naphthyl)biphenyl-4-carboxylic acid In a manner similar to that of Example 1(e), starting with 750 mg (1.2 mmol) of the diester obtained in Example 55(a), 610 mg (100%) of 4'-(5-carboxypentyloxy)-3'-(5,5,8,8-tetramethyl-5,6,7,8-tetrahydro-2-naphthyl)biphenyl-4-carboxylic acid are obtained in the form of a white crystalline solid with a melting point of 245° C.

$^1$H NMR (DMSO-d$_6$) δ 1.28 (s, 12H), 1.36 to 1.44 (m, 2H), 1.46 to 1.55 (m, 2H), 1.68 (s, 4H), 1.69 to 1.73 (m, 2H), 2.18 (t, 2H, J=7.0 Hz), 4.04 (t, 2H, J=6.0 Hz), 7.20 (d, 1H, J=8.6 Hz), 7.30 (dd, 1H, J=8.0/1.2 Hz), 7.37 (d, 1H, J=8.2 Hz), 7.56 (d, 1H, J=1.1 Hz), 7.61 (d, 1H, J=2.2 Hz), 7.66 (dd, 1H, J=8.6/2.1 Hz), 7.81 (d, 2H, J=8.4 Hz), 7.99 (d, 2H, J=8.3 Hz).

Example 57

2'-(5,5,8,8-Tetramethyl-5,6,7,8-tetrahydro-2-naphthyl)-[1,1';4',1"]terphenyl-4"-carboxamide (a) 2'-(5,5,8,8-Tetramethyl-5,6,7,8-tetrahydro-2-naphthyl)-[1,1';4',1"]terphenyl-4"-carbonyl chloride.

6.00 g (12.9 mmol) of the acid obtained in Example 14 and 240 ml of dichloromethane are introduced into a three-necked flask under a stream of nitrogen. 2.63 ml (13.5 mmol) of dicyclohexylamine are added dropwise and the solution obtained is stirred for ten minutes at room temperature. 984 μl (13.5 mmol) of thionyl chloride are added dropwise and the solution obtained is stirred for fifteen minutes at room temperature. The reaction medium is evaporated to dryness, the residue is taken up in ethyl ether and filtered and the filtrate is evaporated to dryness. The acid chloride thus obtained is used directly in the following step.

(b) 2'-(5,5,8,8-Tetramethyl-5,6,7,8-tetrahydro-2-naphthyl)-[1,1';4',1"]terphenyl-4"-carboxamide 1.03 g (2.1 mmol) of the acid chloride obtained in the above step are dissolved in 100 ml of THF. The solution thus obtained is added dropwise to a solution composed of 2.6 ml (43.0 mmol) of aqueous 32% ammonia solution and 20 ml of THF. The reaction medium is stirred for one hour at room temperature, poured into water and extracted with ethyl ether. The organic phase is washed with water to neutral pH, dried over magnesium sulphate and filtered and the solvents are evaporated off. The residue obtained is triturated from heptane, filtered and dried. 940 mg (95%) of 2'-(5,5,8,8-tetramethyl-5,6,7,8-tetrahydro-2-naphthyl)-[1,1';4',1"]terphenyl-4"-carboxamide are collected in the form of a beige-coloured powder with a melting point of 220° C.

$^1$H NMR (CDCl$_3$) δ 0.91 (s, 6H), 1.26 (s, 6H), 1.56 to 1.64 (m, 4H), 6.20 (br s, 2H), 6.89 (d, 1H, J=1.3 Hz), 7.14 to 7.29 (m, 7H), 7.51 (d, 1H, J=7.9 Hz), 7.64 (dd, 1H, J=7.9/1.5 Hz), 7.72 (s, 1H), 7.74 (d, 2H, J=8.2 Hz), 7.91 (d, 2H, J=8.2 Hz).

Example 58

N-Ethyl-2'-(5,5,8,8-tetramethyl-5,6,7,8-tetrahydro-2-naphthyl)-[1,1';4',1"]terphenyl-4"-carboxamide In a manner similar to that of Example 57 (b), starting with 1.30 g (2.7 mmol) of the acid chloride obtained in Example 57(a) and 4.4 ml (54.3 mmol) of aqueous 70% ethylamine solution, 1.20 g (91%) of N-ethyl-2'-(5,5,8,8-tetramethyl-5,6,7,8-tetrahydro-2-naphthyl)-[1,1';4',1"]terphenyl-4"-carboxamide are obtained in the form of a beige-coloured powder with a melting point of 183° C.

$^1$H NMR (CDCl$_3$) δ 0.91 (s, 6H), 1.27 (s, 6H), 1.28 (t, 3H, J=5.7 Hz), 1.56 to 1.63 (m, 4H), 3.53 (q, 2H, J=5.3 Hz), 6.18 (br s, 1H), 6.89 (d, 1H, J=1.9 Hz), 7.14 to 7.29 (m, 7H), 7.51 (d, 2H, J=7.9 Hz), 7.64 (dd, 1H, J=7.9/1.9 Hz), 7.71 (s, 1H), 7.73 (d, 2H, J=8.4 Hz), 7.86 (d, 2H, J=8.4 Hz).

Example 59

N,N-Diethyl-2'-(5,5,8,8-tetramethyl-5,6,7,8-tetrahydro-2-naphthyl)-[1,1';4',1"]terphenyl-4"-carboxamide In a manner similar to that of Example 57(b), starting with 1.30 g (2.7 mmol) of the acid chloride obtained in Example 57(a) and 5.6 ml (54.0 mmol) of diethylamine, 930 mg (67%) of N,N-diethyl-2'-(5,5,8,8-tetramethyl-5,6,7,8-tetrahydro-2-naphthyl)-[1,1';4',1"]terphenyl-4"-carboxamide are obtained in the form of a beige-coloured powder with a melting point of 113° C.
$^1$H NMR (CDCl$_3$) δ 0.85 (s, 6H), 1.25 (m, 6H), 1.27 (s, 6H), 1.56 to 1.64 (m, 4H), 3.35 (br s, 2H), 3.56 (br s, 2H), 6.90 (s, 1H), 7.14 to 7.28 (m, 7H), 7.47 (d, 2H, J=8.2 Hz), 7.52 (s, 1H), 7.63 (dd, 1H, J=8.0/1.4 Hz), 7.68 to 7.71 (m, 3H).

Example 60

Morpholin-4-yl-[2'-(5,5,8,8-tetramethyl-5,6,7,8-tetrahydro-2-naphthyl)-[1,1';4',1"]terphenyl-4"-yl]methanone.

In a manner similar to that of Example 57 (b), starting with 1.03 g (2.1 mmol) of the acid chloride obtained in Example 57(a) and 945 μl (43.0 mmol) of morpholine, 900 mg (80%) of morpholin-4-yl-[2'-(5,5,8,8-tetramethyl-5,6,7,8-tetrahydro-2-naphthyl)-[1,1';4',1"]terphenyl-4"-yl]methanone are obtained in the form of a white powder with a melting point of 223° C.
$^1$H NMR (CDCl$_3$) δ 0.91 (s, 6H), 1.27 (s, 6H), 1.56 to 1.64 (m, 4H), 3.60 to 4.00 (m, 8H), 6.90 (d, 1H, J=1.7 Hz), 7.13 to 7.26 (m, 9H), 7.49 (s, 1H), 7.50 (d, 2H, J=8.4 Hz), 7.63 (dd, 1H, J=7.9/1.8 Hz), 7.72 (d, 2H, J=8.4 Hz).

Example 61

(4-Hydroxyphenyl)-2'-(5,5,8,8-tetramethyl-5,6,7,8-tetrahydro-2-naphthyl)-[1,1';4',1"]terphenyl-4"-carboxamide In a manner similar to that of Example 57(b), starting with 1.04 g (2.2 mmol) of the acid chloride obtained in Example 57(a), 260 mg (23.9 mmol) of 4-aminophenol and 362 μl (2.7 mmol) of triethylamine, 1.15 g (95%) of (4-hydroxyphenyl)-2'-(5,5,8,8-tetramethyl-5,6,7,8-tetrahydro-2-naphthyl)-[1,1';4',1"]terphenyl-4"-carboxamide are obtained in the form of a grey powder with a melting point of 231° C.
$^1$H NMR (CDCl$_3$) δ 0.91 (s, 6H), 1.26 (s, 6H), 1.56 to 1.64 (m, 4H), 6.84 (d, 2H, J=8.5 Hz), 6.89 (d, 1H, J=1.2 Hz), 7.14 to 7.28 (m, 7H), 7.41 to 7.44 (m, 3H), 7.51 (d, 1H, J=7.8 Hz), 7.64 (d, 1H, J=7.8 Hz), 7.72 (s, 1H), 7.75 (d, 2H, J=8.0 Hz), 7.95 (d, 2H, J=8.0 Hz), 8.06 (s, 1H)

Example 62

3-(5,5,8,8-Tetramethyl-5,6,7,8-tetrahydro-2-naphthyl) biphenyl-4-carboxymethyl-4'-carboxylic acid

(a) Benzyl 2'-(5,5,8,8-tetramethyl-5,6,7,8-tetrahydro-2-naphthyl)-4-trifluoromethanesulphonyloxy-[1,1';4',1"]terphenyl-4"-carboxylate In a manner similar to that of Example 13(a), starting with 2.00 g (4.1 mmol) of the compound obtained in Example 53(a), 2.33 g (90%) of the expected product are obtained in the form of a yellow oil.
$^1$H NMR (CDCl$_3$) δ 1.31 (s, 6H), 1.32 (s, 6H), 1.73 (s, 4H), 5.39 (s, 2H), 7.24 to 7.26 (m, 2H), 7.37 to 7.48 (m, 6H), 7.60 to 7.69 (m, 2H), 7.66 (d, 2H, J=8.3 Hz), 8.16 (d, 2H, J=8.3 Hz).

(b) Benzyl 3-(5,5,8,8-tetramethyl-5,6,7,8-tetrahydro-2-naphthyl)biphenyl-4-carboxymethyl-4'-carboxylate 1.80 g (2.9 mmol) of the triflate obtained in Example 62(a), 120 mg (0.29 mmol) of 1,3-bis(diphenylphosphino)propane (DPPP), 32 mg (0.14 mmol) of palladium acetate, 50 ml of methanol, 800 μl (5.8 mmol) of triethylamine and 5 ml of THF are successively introduced into a hydrogenation bomb. The reaction medium is confined under a pressure of six bar of carbon monoxide and heated with stirring at 70° C. for seven hours. The mixture is cooled and evaporated to the maximum, the residue is taken up in saturated sodium chloride solution and extracted with ethyl acetate, the extracts are washed with dilute hydrochloric acid solution and then with water, and the organic phase is dried over magnesium sulphate and evaporated. The residue obtained is purified by chromatography on a column of silica eluted with heptane. After evaporation of the solvents, 1.36 g (88%) of the expected compound are collected in the form of a yellow oil.
$^1$H NMR (CDCl$_3$) δ 1.21 (s, 6H), 1.25 (s, 6H), 1.64 (s, 4H), 3.58 (s, 3H), 5.32 (s, 2H), 7.09 (dd, 1H, J=8.1/2.0 Hz), 7.18 (d, 1H, J=2.2 Hz), 7.27 to 7.38 (m, 6H), 7.53 to 7.56 (m, 2H), 7.62 (d, 2H, J=8.5 Hz), 7.79 (d, 1H, J=7.6 Hz), 8.08 (d, 2H, J=8.5 Hz)

(c) 3-(5,5,8,8-Tetramethyl-5,6,7,8-tetrahydro-2-naphthyl)biphenyl-4-carboxymethyl-4'-carboxylic acid In a manner similar to that of Example 53(c), starting with 450 mg (0.84 mmol) of the benzyl ester obtained in Example 62(b), 330 mg (89%) of 3-(5,5,8,8-tetramethyl-5,6,7,8-tetrahydro-2-naphthyl)biphenyl-4-carboxymethyl-4'-carboxylic acid are collected in the form of a white powder with a melting point of 258–261° C.
$^1$H NMR (DMSO-d$_6$) δ 1.25 (s, 6H), 1.29 (s, 6H), 1.67 (s, 4H), 3.64 (s, 3H), 7.23 (dd, 1H, J=8.0/1.8 Hz), 7.25 (s, 1H), 7.74 (s, 1H), 7.80 (s, 1H), 7.92 (d, 2H, J=8.4 Hz), 8.05 (d, 2H, J=8.4 Hz).

Example 63

3-(5,5,8,8-Tetramethyl-5,6,7,8-tetrahydro-2-naphthyl)biphenyl-4,4'-dicarboxylic acid In a manner similar to that of Example 1(e), starting with 850 mg (1.6 mmol) of the diester obtained in Example 62(b), 600 mg (88%) of 3-(5,5,8,8-tetramethyl -5,6,7,8-tetrahydro-2-naphthyl)biphenyl-4,4'-dicarboxylic acid are obtained in the form of a white crystalline solid with a melting point of 343° C.
$^1$H NMR (DMSO-d$_6$) δ 1.27 (s, 6H), 1.28 (s, 6H), 1.67 (s, 4H), 7.25 (dd, 1H, J=7.9/1.9 Hz), 7.31 (s, 1H), 7.69 (s, 1H), 7.78 (s, 1H), 7.91 (d, 2H, J=8.4 Hz), 8.04 (d, 2H, J=8.4 Hz).

Formulation Examples

The examples which follow illustrate various pharmaceutical and cosmetic formulations based on the compounds according to the invention.

A—Oral Route

(a) 0.2 g tablet

| | |
|---|---|
| Compound prepared in Example 2 | 10.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

In this example, the compound according to Example 2 can be replaced with the same amount of one of the compounds of Examples 4, 8, 14, 17, 29 and 34.

(b) Drinkable suspension in 5 ml vials

| | |
|---|---|
| Compound prepared in Example 1 | 20.001 g |
| Glycerol | 0.500 g |
| 70% sorbitol | 0.500 g |
| Sodium saccharinate | 0.010 g |
| Methyl p-hydroxybenzoate | 0.040 g |
| Flavouring, qs | |
| Purified water qs | 5 ml |

(c) 0.8 g tablet

| | |
|---|---|
| Compound of Example 4 | 0.500 g |
| Pregelatinized starch | 0.100 g |
| Microcrystalline cellulose | 0.115 g |
| Lactose | 0.075 g |
| Magnesium stearate | 0.010 g |

In this example, the compound according to Example 4 can be replaced with the same amount of one of the compounds of Examples 11, 18, 21, 24, 39 and 48.

(d) Drinkabl suspension in 10 ml vials

| | |
|---|---|
| Compound of Example 5 | 0.200 g |
| Glycerol | 1.000 g |
| 70% sorbitol | 1.000 g |
| Sodium saccharinate | 0.010 g |
| Methyl p-hydroxybenzoate | 0.080 g |
| Flavouring, qs | |
| Purified water qs | 10 ml |

B—Topical Route

(a) Ointment

| | |
|---|---|
| Compound of Example 3 | 20.020 g |
| Isopropyl myristate | 81.700 g |
| Fluid liquid vaseline | 9.100 g |
| Silica ("Aerosil 200" sold by Degussa) | 9.180 g |

In this example, the compound according to Example 3 can be replaced with the same amount of one of the compounds of Examples 7, 14, 27, 36 and 53.

(b) Ointment

| | |
|---|---|
| Compound of Example 6 | 0.300 g |
| White petroleum jelly codex | 100 g |

(c) Nonionic water-in-oil cream

| | |
|---|---|
| Compound of Example 2 | 0.100 g |
| Mixture of emulsifying lanolin alcohols, waxes and oils ("anhydrous eucerin" sold by BDF) | 39.900 g |
| Methyl p-hydroxybenzoate | 0.075 g |
| Propyl p-hydroxybenzoate | 0.075 g |
| Sterile demineralized water qs | 100 g |

(d) Lotion

| | |
|---|---|
| Compound of Example 3 | 0.100 g |
| Polyethylene glycol (PEG-400) | 69.900 g |
| 95% ethanol | 30.000 g |

In this example, the compound of Example 3 can be replaced with the same amount of one of the compounds of Examples 8, 18, 24, 32, 35, 43 and 46.

(e) Hydrophobic ointment

| | |
|---|---|
| Compound of Example 1 | 0.300 g |
| Isopropyl myristate | 36.400 g |
| Silicone oil ("Rhodorsil 47V300" sold by Rhône-Poulenc) | 36.400 g |
| Beeswax | 13.600 g |
| Silicone oil ("Abil 300.000 cst" sold by Goldschmidt) | 100 g |

(f) Nonionic oil-in-water cream

| | |
|---|---|
| Compound of Example 5 | 1.000 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl p-hydroxybenzoate | 0.075 g |
| Propyl p-hydroxybenzoate | 0.075 g |
| Sterile demineralized water | 100 g |

In this example, the compound according to Example 5 can be replaced with the same amount of one of the compounds of Examples 29, 49, 51, 52, 58 and 62.

TABLE A
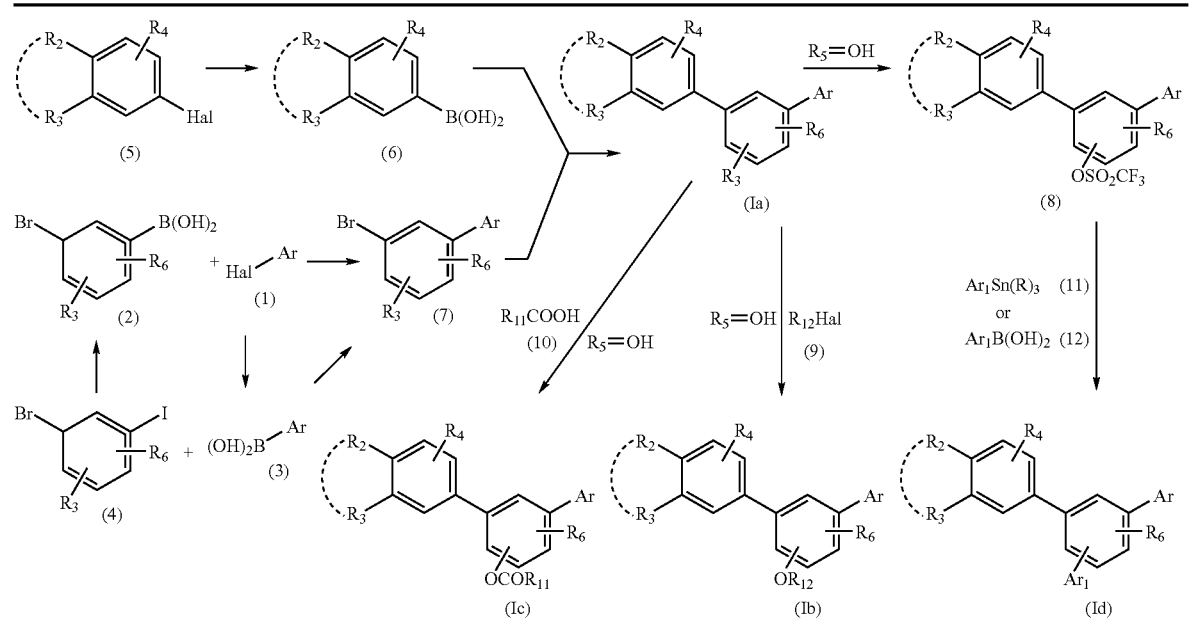
Ar₁ = optionally substituted aryl or heteroaryl
Hal = Br or I
TABLE B
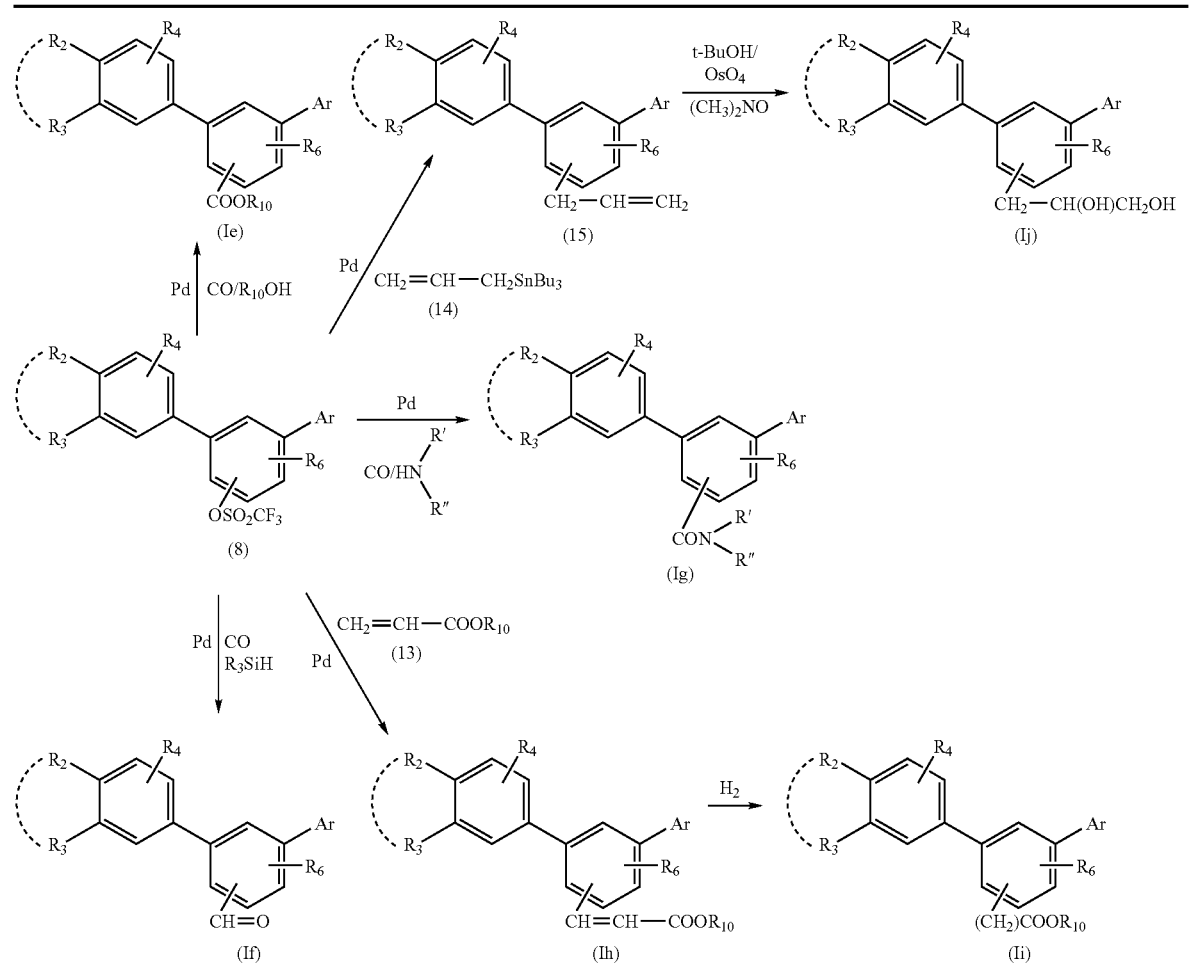

What is claimed is:

1. A biphenyl compound substituted with an aromatic or heteroaromatic radical, characterized in that they correspond to the general formula (I) below:

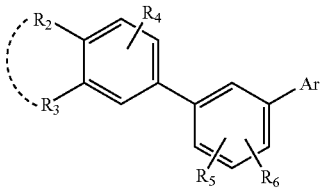
(I)

in which:

Ar represents an aromatic or heteroaromatic radical chosen from:

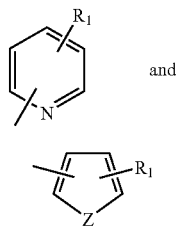

Z being O or S, $R_1$ represents —$COR_9$, $R_2$ and $R_3$, taken together, form a 5- or 6-membered ring, optionally substituted with at least one methyl, $R_4$ represents H, a halogen atom, linear or branched $C_1$–$C_{20}$ alkyl, —$OR_{10}$, —$OCOR_{11}$ or a polyether radical, $R_5$ represents H, a halogen atom, linear or branched $C_1$–$C_{20}$ alkyl, —$OCOR_{11}$, —$OR_{12}$, mono- or polyhydroxyalkl, —$NO_2$,

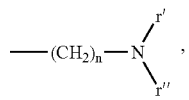

—$(CH_2)_n$—$NHCOCH_3$, —CH=CH—$COR_{13}$, —$(CH_2)_nCOR_{13}$, n being 0 to 6, —O—$(CH_2)_m COR_{13}$, —O—$(CH_2)_mOH$, m being 1 to 12, optionally substituted aryl, optionally substituted aralkyl, optionally substituted heteroaryl, a polyether radical or a —$CH_2$— polyether radical, $R_6$ represents H, lower alkyl or —$OR_{10}$, $R_9$ represents —$OR_{14}$, H or lower alkyl, $R_{10}$ represents H or lower alkyl, $R_{11}$ represents lower alkyl, $R_{12}$ represents H, linear or branched $C_1$–$C_{20}$ alkyl, mono- or polyhydroxyalkyl, or optionally substituted aryl or aralkyl, $R_{13}$ represents H, lower alkyl, —$OR_{10}$, aryl or

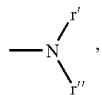

$R_{14}$ represents H, r' and r", which may be identical or different, represent H, OH, lower alkyl, mono- or polyhydroxyalkyl, optionally substituted aryl, an amino acid residue or a peptide residue, or r' and r", taken together, form a heterocycle, or a salt of the compound of formula (I), or an optical or geometrical isomer of the compound of formula (I).

2. A compound according to claim 1, characterized in that they are in the form of a salt of an alkali metal or alkaline-earth metal, or alternatively of zinc or of an organic amine.

3. A compound according to claim 1, characterized in that the lower alkyl radical is chosen from the group consisting of the methyl, ethyl, isopropyl, butyl, tert-butyl and hexyl radicals.

4. A compound according to claim 1, characterized in that the linear or branched $C_1$–$C_{20}$ alkyl is chosen from the group consisting of the methyl, ethyl, propyl, 2-ethylhexyl, octyl, hexadecyl and octadecyl radicals.

5. A compound according to claim 1, characterized in that the monohydoxyalkyl radical is chosen from the group consisting of the hydromethyl, 2-hydroxyethyl, 2-hydropropyl and 3-hydroxypropyl radicals.

6. A compound according to claim 1, characterized in that the polyhydroxyalkyl radical is chosen from the group consisting of the 2,3-dihydroxypropyl, 2,3,4-trihydroxybutyl and 2,3,4,5-tetrahydroxypentyl radicals and the pentaerythritol residue.

7. A compound according to claim 1, characterized in that the polyether radical is chosen from the group consisting of the methoxymethoxy, methoxyethoxy and methoxyethoxymethoxy radicals.

8. A compound according to claim 1, characterized in that the —$CH_2$-polyether radical is chosen from the group consisting of the methoxymethoxymethyl, ethoxymethoxymethyl and methoxyethoxymethoxymethyl radicals.

9. A compound according to claim 1, characterized in that the aryl radical is a phenyl radical optionally substituted with at least one halogen, a hydroxyl, a nitro function, a polyether radical or an amino function optionally protected with an acetyl group or optionally substituted with at least one $C_1$–$C_6$ lower alkyl or alkoxy.

10. A compound according to claim 1, characterized in that the aralkyl radical is chosen from the group consisting of benzyl and phenethyl radicals optionally substituted with at least one halogen atom, a hydroxyl, a nitro function, a polyether radical or an amino function optionally protected with an acetyl group or optionally substituted with at least one $C_1$–$C_6$ lower alkyl or alkoxy.

11. A compound according to claim 1, characterized in that the heteroaryl radical is chosen from the group consisting of pyridyl, furyl and thienyl radicals, optionally substituted with at least one halogen, a lower alkyl, a hydroxyl, a $C_1$–$C_3$ alkoxy, a nitro function, a polyether radical or an amino function optionally protected with an acetyl group or optionally substituted with at least one $C_1$–$C_6$ lower alkyl or alkoxy.

12. A compound according to claim 1, characterized in that the amino acid residue is chosen from the group consisting of residues derived from lysine, from glycine and from aspartic acid.

13. A compound according to claim 1, characterized in that the peptide residue is chosen from the group consisting of dipeptide and tripeptide residues.

14. A compound according to claim 1, characterized in that when r' and r" form a heterocycle, this is chosen from the group consisting of piperidino, morpholino, pyrrolidino and piperazino radicals, optionally substituted in position 4 with a $C_1$–$C_6$ alkyl or a mono- or polyhydroxyalkyl.

15. A compound according to claim 1, characterized in that the halogen atom is chosen from the group consisting of fluorine, chlorine and bromine.

16. A compound according to claim 1, characterized in that they correspond to the general formulae (II) below:

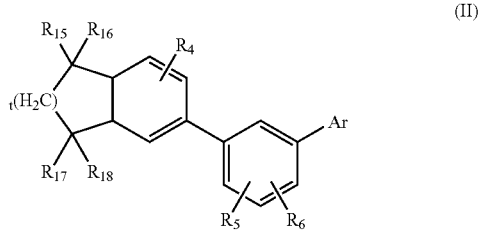

in which:

Ar represents a radical of formula (b) below:

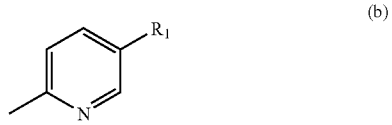

$R_1$, $R_4$, $R_5$, $R_6$, and $R_7$ having the same meanings as those given in claim 1, $R_{15}$, $R_{16}$, $R_{17}$ and $R_{18}$, which may be identical or different, represent H or —$CH_3$, and t is 1 or 2.

17. A compound according to claim 1, characterized in that they are taken from the group consisting of:
  6-[2-(5,5,8,8-tetramethyl-5,6,7,8-tetrahydro-2-naphthyl)biphenyl-4-yl]nicotinic acid,
  5-[2-(5,5,8,8-tetramethyl-5,6,7,8-tetrahydro-2-naphthyl)biphenyl-4-yl]2-pyridinecarboxylic acid, and
  2-[2-(5,5,8,8-tetramethyl-5,6,7,8-tetrahydro-2-naphthyl)biphenyl-4-yl]-4-thiophenecarboxylic acid.

18. A compound according to claim 1, for use as a medicinal product.

19. A pharmaceutical composition, characterized in that it comprises, in a pharmaceutically acceptable support, at least one compound as defined according to claim 1.

20. A pharmaceutical composition according to claim 19, characterized in that the concentration of said at least one compound is between 0.001% and 5% by weight relative to the total weight of the composition.

21. A cosmetic composition, characterized in that it contains, in a cosmetically acceptable support, at least one compound as defined according to claim 1.

22. A cosmetic composition according to claim 21, characterized in that the concentration of said at least one compound is between 0.001 and 3% by weight relative to the total weight of the composition.

23. A dermatological, immunoallergic, cardiovascular and/or opthalmological treatment method comprising administering a composition comprising a compound according to claim 1 to a person in need of said treatment.

24. A cosmetic treatment method for repairing or combating aging of the skin comprising applying to the part of the skin to be treated a composition comprising a compound according to claim 1 to a person in need of said cosmetic treatment.

25. A dermatological, immunoallergic, cardiovascular or ophthalmological treatment method comprising administering a composition comprising a compound according to claim 1, to a person in need of said treatment.

26. The method of claim 25, for treating dermatological complaints associated with keratinization disorders.

27. The method of claim 25, for treating acne.

28. The method of claim 25, for treating ichthyosis, Darier's diseases, palmoplantar keratoderma, leucophasia and cutaneous or mucous lichen.

29. The method of claim 25, for treating psoriasis, cutaneous atopy, respiratory atopy or gingival hypertrophy.

30. The method of claim 29, for treating eczema.

31. The method of claim 25, for treating dermal or epiderman proliferations.

32. The method of claim 31, for treating warts, papillomatoses and uv-induced proliferations.

33. The method of claim 25, for treating bullosis or collagen diseases.

34. The method of claim 25, for treating corneopathies.

35. The method of claim 25, for treating cutaneous atrophy.

36. The method of claim 25, for combating cicatrization disorders or stretch marks.

37. The method of claim 25, for combating seborrhoea.

38. The method of claim 25, for combating arthritis.

39. The method of claim 25, for combating alopecia.

40. The method of claim 25, for combating arteriosclerosis.

* * * * *